(12) United States Patent
Preiss-Bloom et al.

(10) Patent No.: US 12,239,766 B2
(45) Date of Patent: Mar. 4, 2025

(54) CONTINUOUS-FIBER REINFORCED BIOCOMPOSITE MEDICAL IMPLANTS

(71) Applicant: OSSIO, LTD, Caesarea (IL)

(72) Inventors: Orahn Preiss-Bloom, Zichron Yakov (IL); Taly Pnina Lindner, Savyon (IL); Eyal Epstein, Tel Aviv (IL); Danielle Poreh, Herzliyya (IL)

(73) Assignee: OSSIO LTD., Caesarea (IL)

( * ) Notice: Subject to any disclaimer, the term of this patent is extended or adjusted under 35 U.S.C. 154(b) by 0 days.

(21) Appl. No.: 18/364,476

(22) Filed: Aug. 3, 2023

(65) Prior Publication Data

US 2024/0115775 A1 Apr. 11, 2024

Related U.S. Application Data

(63) Continuation of application No. 17/152,165, filed on Jan. 19, 2021, now Pat. No. 11,730,866, which is a
(Continued)

(51) Int. Cl.
*A61L 31/12* (2006.01)
*A61B 17/86* (2006.01)
(Continued)

(52) U.S. Cl.
CPC .......... *A61L 31/128* (2013.01); *A61B 17/864* (2013.01); *A61B 17/866* (2013.01); *A61F 2/4455* (2013.01); *A61F 2/447* (2013.01); *A61L 27/446* (2013.01); *A61L 27/58* (2013.01); *A61L 31/06* (2013.01); *A61L 31/08* (2013.01); *A61L 31/148* (2013.01); *A61F 2002/30062* (2013.01);
(Continued)

(58) Field of Classification Search
CPC ........ A61L 31/06; A61L 31/08; A61L 31/128; A61L 31/148; A61L 31/446; A61F 2002/4495
See application file for complete search history.

(56) References Cited

U.S. PATENT DOCUMENTS 4,655,777 A 4/1987 Dunn
4,750,905 A 6/1988 Koeneman
(Continued)

FOREIGN PATENT DOCUMENTS

CN 1168105 A 12/1997
CN 1214939 A 4/1999
(Continued)

OTHER PUBLICATIONS

Office Action dated Aug. 5, 2019 for U.S. Appl. No. 15/509,274 (pp. 1-19).
(Continued)

*Primary Examiner* — Matthew J Lawson
(74) *Attorney, Agent, or Firm* — GRAESER ASSOCIATES INTERNATIONAL INC; Dvorah Graeser

(57) ABSTRACT

A medical implant comprising a plurality of biocomposite layers, each layer comprising a polymer and a plurality of uni-directionally aligned continuous reinforcement fibers. The medical implant is suitable for load-bearing orthopedic implant applications and comprises one or more biocomposite materials where sustained mechanical strength and stiffness are critical for proper implant function.

24 Claims, 36 Drawing Sheets

Related U.S. Application Data continuation of application No. 15/523,389, filed as application No. PCT/IB2015/002602 on Dec. 28, 2015, now Pat. No. 10,926,004.

(60) Provisional application No. 62/096,932, filed on Dec. 26, 2014.

(51) Int. Cl.
- *A61F 2/30* (2006.01)
- *A61F 2/44* (2006.01)
- *A61L 27/44* (2006.01)
- *A61L 27/58* (2006.01)
- *A61L 31/06* (2006.01)
- *A61L 31/08* (2006.01)
- *A61L 31/14* (2006.01)

(52) U.S. Cl.
CPC ............... *A61F 2002/30593* (2013.01); *A61F 2002/4495* (2013.01)

(56) References Cited

U.S. PATENT DOCUMENTS

| | | |
|---|---|---|
| 4,911,718 A | 3/1990 | Lee |
| 5,064,439 A | 11/1991 | Chang |
| 5,181,930 A | 1/1993 | Dumbleton |
| 5,192,330 A | 3/1993 | Chang |
| 5,312,669 A | 5/1994 | Bedard |
| 5,338,772 A | 8/1994 | Bauer |
| 5,522,817 A | 6/1996 | Sander |
| 5,522,904 A * | 6/1996 | Moran ............... A61F 2/3609 623/23.34 |
| 5,674,294 A | 10/1997 | Bainville |
| 5,679,299 A | 10/1997 | Gilbert |
| 6,004,650 A | 12/1999 | Schweizer |
| 6,171,338 B1 | 1/2001 | Talja |
| 6,299,649 B1 | 10/2001 | Chang |
| 6,306,140 B1 | 10/2001 | Siddiqui |
| 6,352,667 B1 | 3/2002 | English |
| 6,471,707 B1 | 10/2002 | Miller |
| 6,511,511 B1 | 1/2003 | Slivka |
| 6,602,293 B1 | 8/2003 | Biermann |
| 6,916,321 B2 | 7/2005 | Tenhuisen |
| 7,541,049 B1 | 6/2009 | Toermaelae |
| 7,918,879 B2 | 4/2011 | Yeung |
| 7,947,069 B2 | 5/2011 | Sanders |
| 8,702,716 B1 | 4/2014 | Stein |
| 8,709,055 B2 | 4/2014 | Beyar |
| 8,735,504 B2 | 5/2014 | Clay |
| 8,992,622 B2 | 3/2015 | Ullrich, Jr. |
| 9,186,302 B2 | 11/2015 | Kilway |
| 9,456,890 B2 | 10/2016 | Day |
| 10,869,708 B2 | 12/2020 | Preiss-Bloom |
| 10,869,954 B2 | 12/2020 | Preiss-Bloom |
| 10,926,004 B2 | 2/2021 | Preiss-Bloom |
| 11,020,110 B1 | 6/2021 | Blair |
| 11,317,957 B2 | 5/2022 | Preiss-Bloom |
| 11,491,264 B2 | 11/2022 | Preiss-Bloom |
| 11,730,866 B2 | 8/2023 | Preiss-Bloom |
| 2005/0118326 A1 | 6/2005 | Anfinsen |
| 2005/0177245 A1 | 8/2005 | Leatherbury |
| 2005/0216016 A1 | 9/2005 | Contiliano |
| 2005/0226904 A1 * | 10/2005 | Choi ............... A61L 27/18 424/443 |
| 2005/0228500 A1 | 10/2005 | Kim |
| 2006/0020266 A1 | 1/2006 | Cooper |
| 2006/0095134 A1 | 5/2006 | Trieu |
| 2006/0154206 A1 | 7/2006 | Petersson |
| 2006/0178748 A1 | 8/2006 | Dinger, III |
| 2007/0150059 A1 | 6/2007 | Ruberte |
| 2007/0185568 A1 | 8/2007 | Schwartz |
| 2007/0270969 A1 | 11/2007 | Schmid |
| 2007/0282455 A1 | 12/2007 | Luginbuehl |
| 2008/0255561 A1 | 10/2008 | Tormala |
| 2009/0112317 A1 | 4/2009 | Li |
| 2009/0216233 A1 | 8/2009 | Wiedrich |
| 2009/0240337 A1 | 9/2009 | Myung |
| 2009/0258965 A1 | 10/2009 | Lassila |
| 2009/0304761 A1 | 12/2009 | Rabiei |
| 2010/0119564 A1 | 5/2010 | Kasuga |
| 2010/0121463 A1 | 5/2010 | Toermaelae |
| 2010/0168798 A1 | 7/2010 | Clineff |
| 2011/0098826 A1 | 4/2011 | Mauck |
| 2011/0166659 A1 | 7/2011 | Luginbuehl |
| 2011/0282395 A1 | 11/2011 | Beyar |
| 2012/0000893 A1 | 1/2012 | Broude |
| 2012/0016373 A1 | 1/2012 | Impellizzeri |
| 2012/0040002 A1 | 2/2012 | Lehtonen |
| 2012/0040015 A1 | 2/2012 | Lehtonen |
| 2012/0040137 A1 | 2/2012 | Palasis |
| 2012/0191214 A1 | 7/2012 | Nies |
| 2012/0265206 A1 | 10/2012 | Jang |
| 2013/0144400 A1 * | 6/2013 | Day ............... A61L 27/446 623/23.72 |
| 2013/0204368 A1 | 8/2013 | Prevost |
| 2013/0218291 A1 | 8/2013 | Giorno |
| 2013/0296500 A1 | 11/2013 | Clay |
| 2013/0317555 A1 | 11/2013 | Schaller |
| 2014/0018809 A1 | 1/2014 | Allen |
| 2015/0238655 A1 | 8/2015 | Jongpaiboonkit |
| 2015/0289979 A1 | 10/2015 | Gabele |
| 2016/0011369 A1 | 1/2016 | Doyle |
| 2016/0113695 A1 | 4/2016 | Globerman |
| 2016/0278789 A1 | 9/2016 | Garvey |
| 2017/0181785 A1 | 6/2017 | Beyar |
| 2017/0246355 A1 | 8/2017 | Preiss-Bloom |
| 2017/0246356 A1 | 8/2017 | Preiss-Bloom |
| 2019/0099522 A1 | 4/2019 | Preiss-Bloom |
| 2019/0261974 A1 | 8/2019 | Arai |
| 2019/0282736 A1 | 9/2019 | Preiss-Bloom |
| 2020/0016846 A1 | 1/2020 | Davidson |
| 2020/0345895 A1 | 11/2020 | Preiss-Bloom |
| 2021/0022725 A1 | 1/2021 | Burkhart |
| 2021/0128137 A1 | 5/2021 | Rogers |
| 2021/0137576 A1 | 5/2021 | Preiss-Bloom |
| 2021/0161571 A1 | 6/2021 | Haziza |
| 2021/0205505 A1 | 7/2021 | Preiss-Bloom |
| 2021/0299332 A1 | 9/2021 | Dias |
| 2021/0369314 A1 | 12/2021 | Preiss-Bloom |
| 2022/0001081 A1 | 1/2022 | Preiss-Bloom |
| 2022/0008615 A1 | 1/2022 | Cige |

FOREIGN PATENT DOCUMENTS

| | | |
|---|---|---|
| CN | 1371664 A | 10/2002 |
| CN | 1565396 A | 1/2005 |
| CN | 1593356 A | 3/2005 |
| CN | 1668255 A | 9/2005 |
| CN | 1953719 A | 4/2007 |
| CN | 101106957 A | 1/2008 |
| CN | 101420991 A | 4/2009 |
| CN | 101437467 A | 5/2009 |
| CN | 101790559 B | 7/2010 |
| CN | 101942709 A | 1/2011 |
| CN | 102281907 A | 12/2011 |
| CN | 102395329 A | 3/2012 |
| CN | 102421463 A | 4/2012 |
| CN | 102421716 A | 4/2012 |
| CN | 103747813 A | 4/2014 |
| CN | 104188706 A | 12/2014 |
| CN | 106687077 | 3/2016 |
| CN | 106392332 A | 2/2017 |
| CN | 107106210 | 8/2017 |
| EP | 0373294 A2 | 6/1990 |
| EP | 1716874 A2 | 11/2006 |
| EP | 2243500 A1 | 10/2010 |
| EP | 2243749 A1 | 10/2010 |
| EP | 2292166 A1 | 3/2011 |
| EP | 17819487 | 6/2017 |
| EP | 3236866 | 11/2017 |
| EP | 3320877 A1 | 5/2018 |
| EP | 3678566 | 7/2020 |
| EP | 3689259 | 8/2020 |

(56) References Cited

FOREIGN PATENT DOCUMENTS

| | | |
|---|---|---|
| JP | 6415040 | 1/1989 |
| JP | H02121652 | 5/1990 |
| JP | 2002501418 A | 1/2002 |
| JP | 2004160157 | 6/2004 |
| JP | 2005512702 | 5/2005 |
| JP | 2005533551 | 11/2005 |
| JP | 2008200510 | 9/2008 |
| JP | 2009541568 | 11/2009 |
| JP | 2010526200 | 7/2010 |
| JP | 2012524569 | 10/2012 |
| WO | 9609014 A1 | 3/1996 |
| WO | 1996009014 | 3/1996 |
| WO | 9819616 | 5/1998 |
| WO | 1998019617 A1 | 5/1998 |
| WO | 9853768 A1 | 12/1998 |
| WO | 0132072 | 5/2001 |
| WO | 2005077039 A2 | 8/2005 |
| WO | 2005077039 A3 | 8/2005 |
| WO | 2008095046 A2 | 8/2008 |
| WO | 2010122019 A1 | 10/2010 |
| WO | 2010122098 A2 | 10/2010 |
| WO | 2013116624 A1 | 8/2013 |
| WO | 2016035088 A1 | 3/2016 |
| WO | 2016035089 | 3/2016 |
| WO | 2016103049 A1 | 6/2016 |
| WO | 2017155956 A1 | 9/2017 |
| WO | 2018002917 | 1/2018 |
| WO | 2019049062 | 3/2019 |
| WO | 2019123462 | 6/2019 |
| WO | 2020044327 | 3/2020 |
| WO | 2023002471 | 1/2023 |

OTHER PUBLICATIONS

Office Action dated Dec. 26, 2019 for U.S. Appl. No. 15/509,274, 18 pages.
Office Action dated Feb. 10, 2020, for U.S. Appl. No. 16/081,605 (pp. 1-17).
Office Action dated Jan. 13, 2020 for U.S. Appl. No. 15/523,389 (pp. 1-11).
Office Action dated Jul. 13, 2020 for U.S. Appl. No. 15/523,389 (pp. 1-12).
Office Action dated Nov. 18, 2019 for U.S. Appl. No. 16/081,605 (pp. 1-19).
Office Action dated Nov. 19, 2020 for U.S. Appl. No. 16/311,784 (pp. 1-14).
Office Action dated Nov. 7, 2019 for U.S. Appl. No. 15/523,389 (pp. 1-11).
Office Action dated Sep. 23, 2021 for U.S. Appl. No. 16/311,784 (pp. 1-11).
P. Amuthakkannan, V. Manikandan, J.T. Winowlin Jappes, M. Uthayakumar Effect of Fibre Length and Fibre Content On Mechanical Properties of Short Basalt Fibre Reinforced Polymer Matrix Composites Materials Physics and Mechanics 16 (2013) 107-117.
Polymer-Matrix Composites: Structure and Processing Deborah D.L. Chung, in Carbon Composites (Second Edition), 2017 3.3.4 Fiber Fragmentation Testing, 13 pages.
Rodricks CW, Greenfeld I, Fiedler B, Wagner HD. Fragmentation of Beaded Fibres in a Composite. Materials (Basel). Jan. 24, 2022;15(3):890, 22 pages.
Scholz et al., "The use of composite materials in modern orthopaedic medicine and prosthetic devices: A review", Composites Science and Technology, Elsevier, Amsterdam, NL, www.elsevier.com/locate/compscitech, vol. 71, No. 16 (2011) pp. 1791-1803.
Search report for parent PCT application No. PCT/IL2015/050903, mailed on Jan. 7, 2016 (13 pages).
Shia, David & Hui, Chung Yuen & Phoenix, S.. (2000). Statistics of fragmentation in a single-fiber composite under matrix yielding and debonding with application to the strength of multi-fiber composites. Composites Science and Technology. 60. 2107-2128. 10.1016/S0266-3538(00)00115-9. (Abstract) 7 pages.
Shiqiang Deng, Lin Ye, Yiu-Wing Mai, Hong-Yuan Liu, Evaluation of fibre tensile strength and fibre/matrix adhesion using single fibre fragmentation tests, Composites Part A: Applied Science and Manufacturing, vol. 29, Issue 4, 1998, pp. 423-434 (Abstract).
Supplementary European Search Report for EP15837823 dated Mar. 28, 2018, 6 pgs.
Wang et al., "Promising Poly(E-caprolactone) composite reinforced with weft-knitted polyester for small-diameter vascular graft application", Advances in Materials Science and Engineering, 2014, vol. 2014, p. 273891, 11 pages.
Website downloaded Aug. 23, 2022 (https://www.orthobullets.com/basic-science/9062/material-properties) 11 pages.
Wegener et al., "Microstructure, cytotoxicity and corrosion of powder-metallurgical iron alloys for biodegradable bone ematerials", Materials Science & Engineering. B. Advanced Functional Solid-State Materials, 2011, vol. 176, No. 20, p. 1789-1796.
WOISA from PCT/IL2022/051252 dated Feb. 9, 2023, 8 pages.
WOSA from PCT/IL2022/050711 dated Oct. 19, 2022, 6 pages.
Extended European Search Report for App. No. EP18853365.7, dated May 4, 2021, 7 pages.
Extended European Search Report for App. No. EP18890927.9, dated Jul. 27, 2021, 7 pages.
Extended European Search Report for Application No. EP17819487.4, dated Feb. 4, 2020, 7 pages.
Extended European Search Report for Application No. EP19200585.8, dated Feb. 28, 2020, 8 pages.
Extended European Search Report issued in App. No. EP22185127, dated Dec. 15, 2022, 9 pages.
Feih, S., Wonsyld, K., Minzari, D., Westermann, P., & Lilholt, H. (2004). Testing Procedure for the Single Fiber Fragmentation Test. Risø National Laboratory. Denmark. Forskningscenter Risoe. Risoe-R No. 1483(EN) 31 pages.
Ferri JM et al., "The effect of beta-tricalcium phosphate on mechanical and thermal performances of poly(lactic acid)", J Composite Materials 2016; 0(0): 1-10.
Hyon et al., "Effects of Residual Monomer on the Degradation of DL-Lactide Polymer" Polymer International 46 (1998) 196-202.
Indian Examination Report for App. No. IN201827049363, dated Nov. 18, 2021, 5 pages.
Indian Examination Report issued in App. No. IN202027011276, dated Apr. 27, 2022, 7 pages.
International Search Report issued in PCT/IL2019/050843, dated Nov. 6, 2019, 3 pages.
IP Office of Singapore Written Opinion for Application No. SG11201610671P, dated Aug. 14, 2019, 5 pages.
ISR from PCT/IL2022/050711 dated Oct. 19, 2022, 5 pages.
ISR from PCT/IL2022/051252 dated Feb. 9, 2023, 5 pages.
Israel Office Action issued in IL Patent Application No. 280837 dated Dec. 7, 2023.
Japanese Appeal Hearing (including English translation) for App. No. JP2018-567587, dated Dec. 5, 2023, 3 pages.
Japanese Office Action (includig English translation) issued in App. No. JP2020-511984, dated Aug. 2, 2022, 13 pages.
Japanese Office Action (including English translation) for App. No. JP2018-567587, dated Dec. 5, 2023, 28 pages.
Japanese Office Action (including English translation) for App. No. JP2018-567587, dated Jan. 5, 2022, 5 pages.
Japanese Office Action (including English translation) issued in App. No. JP2021-507819, dated May 30, 2023, 10 pages.
Japanese Office Action (with English language translation) for Application No. 2017-504425, dated May 28, 2019, 7 pages.
Japanese Office Action (with English language translation) for Application No. JP2017-504425, dated Jan. 7, 2020, 6 pages.
Japanese Office Action (with English language translation) for Application No. JP2017-527796, mailing date Nov. 5, 2019, 6 pages.
Japanese Office Action issued in App. No. JP2021-507819, dated Nov. 21, 2023, 4 pages.
Juan David Vanegas-Jaramillo, Ivan David Patiño-Arcilaa, Fragmentation model for the tensile response of unidirectional composites based on the critical number of fiber breaks and the correction of the fiber-matrix interfacial strength Latin American Journal of Solids and Structures, 2019, 16(7), e217, 27 pages.

(56) References Cited

OTHER PUBLICATIONS

Jurij Štalc, Luke D. Cicchinelli, Stuart Miller, Carolyn M. Sofka, Martinus Richter Fiber-reinforced fixation implant for proximal interphalangeal joint arthrodesis shows advanced implant biointegration at 2-year follow-up Foot Ankle Surg. Jun. 23, 2022:S1268-7731(22)00117-5, 7 pages.
Korean Office Action (including English translation) for App. No. KR10-2019-7001863, dated Jan. 20, 2022, 13 pages.
Korean Office Action issued in App. No. KR10-2017-7018042, dated Aug. 17, 2022, 7 pages.
Kulkova J. et al., "Hydroxyapatite and bioactive glass surfaces for fiber reinforced composite implants via surface ablation by Excimer laser", Journal of the Mechanical Behavior of Biomedical Materials, vol. 75, doi: 10.1016/j.jmbbm.2017.07.005, (20170000), pp. 89-96, (Jul. 4, 2017), XP055696388.
Li Sijiao, "Modern Chromatographic Analysis", p. 118, National Defense Industry Press, Jun. 2014 (3 pages).
Miwa, M., Horiba, N. Effects of fiber length on tensile strength of carbon/glass fiber hybrid composites. Journal of Materials Science 29, 973-977 (1994).
Miwa, M., Ohsawa, T., and Tahara, K. (1980), Effects of fiber length on the tensile strength of epoxy/glass fiber and polyester/glass fiber composites. J. Appl. Polym. Sci., 25: 795-807 (Abstract).
Notice of Allowance dated Aug. 20, 2020 for U.S. Appl. No. 15/509,301 (pp. 1-9).
Notice of Allowance dated Aug. 28, 2020 for U.S. Appl. No. 16/081,605 (pp. 1-14).
Notice of Allowance dated Oct. 22, 2020 for U.S. Appl. No. 15/523,389 (pp. 1-6).
Office Action (Final Rejection) dated Feb. 22, 2023 for U.S. Appl. No. 17/152,165 (pp. 1-15).
Office Action (Final Rejection) dated Jun. 6, 2023 for U.S. Appl. No. 16/770,091 (pp. 1-23).
Office Action (Final Rejection) dated Oct. 28, 2022 for U.S. Appl. No. 16/951,109 (pp. 1-7).
Office Action (Non-Final Rejection) dated Jul. 21, 2022 for U.S. Appl. No. 16/951,109 (pp. 1-8).
Office Action (Non-Final Rejection) dated Sep. 29, 2023 for U.S. Appl. No. 17/268,449 (pp. 1-15).
Office Action (Non-Final Rejection) dated Nov. 7, 2022 for U.S. Appl. No. 17/152,165 (pp. 1-15).
Office Action (Non-Final Rejection) dated Nov. 25, 2022 for U.S. Appl. No. 16/770,091 (pp. 1-22).
Office Action (Notice of Allowance and Fees Due (PTOL-85)) dated Jan. 18, 2022 for U.S. Appl. No. 16/637,363 (pp. 1-9).
Office Action (Notice of Allowance and Fees Due (PTOL-85)) dated Feb. 8, 2022 for U.S. Appl. No. 16/311,784 (pp. 1-6).
Office Action (Notice of Allowance and Fees Due (PTOL-85)) dated Feb. 15, 2023 for U.S. Appl. No. 16/951,109 (pp. 1-8).
Office Action (Notice of Allowance and Fees Due (PTOL-85)) dated Feb. 22, 2022 for U.S. Appl. No. 16/311,784 (pp. 1-3).
Office Action (Notice of Allowance and Fees Due (PTOL-85)) dated Mar. 29, 2022 for U.S. Appl. No. 16/637,363 (pp. 1-6).
Office Action (Notice of Allowance and Fees Due (PTOL-85)) dated May 26, 2023 for U.S. Appl. No. 17/152,165 (pp. 1-6).
Office Action (Notice of Allowance and Fees Due (PTOL-85)) dated Jun. 12, 2023 for U.S. Appl. No. 17/152,165 (pp. 1-3).
Office Action dated Apr. 7, 2021 for U.S. Appl. No. 16/311,784 (pp. 1-11).
Arthrex Inc., "BioComposite Interference Screws—A Stronger turn in ACL/PCL Reconstruction", Scientific Research and Development, (20100000), URL: http://www.arthrex.com/knee/biocomposite-interference-screws. (6 pages).
Australian Examination Report No. 1 for App. No. AU2017287968, dated Aug. 31, 2021, 3 pages.
Australian Examination Report No. 1 for App. No. AU2017287968, dated Feb. 12, 2021, 4 pages.
Australian Examination Report No. 1 for Application No. 2015310510, dated Aug. 10, 2019, 6 pages.
Australian Examination Report No. 1 for Application No. AU2015370600, dated Oct. 2, 2019, 3 pages.
Australian Examination Report No. 1 issued in App. No. AU2018327272, dated Aug. 18, 2023, 4 pages.
Australian Examination Report No. 2 for Application No. AU2015310510, dated Dec. 1, 2019, 3 pages.
Australian Examination Report No. 2 for Application No. AU2015370600, dated Jan. 29, 2020, 2 pages.
Brazilian Office Action (including English translation) issued in App. No. BR112021001791, dated Apr. 5, 2023, 8 pages.
Brazilian Search Report (with English language translation) for App No. BR112017001049-6, dated Apr. 8, 2020, 8 pages.
Brazilian Technical Report (with English language translation) for App No. BR112017012508-0, dated Apr. 8, 2020, 7 pages.
C. Capelaa, S. E. Oliveiraa, J. Pestanaa, J.A.M. Ferreira, "Effect of fiber length on the mechanical properties of high dosage carbon reinforced", Procedia Structural Integrity 5 (2017) 539-546.
Canadian Office Action for App. No. CA2,955,392, dated Sep. 27, 2021, 15 pages.
Canadian Office Action issued in App. No. CA2,955,392, dated May 31, 2022, 4 pages.
Canadian Office Action issued in App. No. CA3,028,635, dated Aug. 9, 2023, 7 pages.
Chinese Office Action (including English translation) for App. No. CN201780025291.1, dated Aug. 10, 2021, 12 pages.
Chinese Office Action (including English translation) for App. No. CN201780025291.1, dated Jan. 28, 2021, 12 pages.
Chinese Office Action (including English translation) for App. No. CN201980053932.3, dated Jan. 13, 2022, 10 pages.
Chinese Office Action (including English translation) issued in App. No. CN201880057783.3, dated Aug. 2, 2022, 16 pages.
Chinese Office Action (including English translation) issued in App. No. CN20188086979, dated Jul. 28, 2023, 14 pages.
Chinese Office Action (with English language translation) for App No. CN201580070362.0, datetd May 20, 2020, 9 pages.
Chinese Office Action (with English language translation) for Application No. 201580036606.3, dated Mar. 12, 2019, 13 pages.
Chinese Office Action (with English language translation) for Application No. CN201580036606.3, dated Oct. 25, 2019, 9 pages.
Chinese Office Action (with English language translation) for Application No. CN201580037255.8, dated Aug. 26, 2019, 16 pages.
Chinese Office Action (with English language translation) for Application No. CN201580070362.0, dated Aug. 29, 2019, 10 pages.
Chinese Office Action (with English translation) for App. No. CN201780053086.6, dated May 7, 2022, 21 pages.
Chinese Office Action (with English translation) for App. No. CN201780053086.6, dated Oct. 19, 2021, 15 pages.
Chinese Office Action dated Jul. 13, 2018 for corresponding CN Patent Application No. 201580037255.8, 9 pages.
Chinese Office Action for App. No. CN201780053086.6, dated Feb. 18, 2021, 23 pages.
Chinese Office Action for App. No. CN201880057783.3, dated Dec. 2, 2021, 15 pages.
Chinese Office Action for Appl. No. 201580037255.8, dated Mar. 26, 2019, 7 pages.
Chinese Third Office Action (with English translation) for App. No. CN201780053086.6, dated Feb. 16, 2022, 13 pages.
Composites Encyclopedia, Wo Dingzhu et al., pp. 519-520, Beijing: Chemical Industry Press, Jan. 2001, (pp. 7-12).
Corrected Notice of Allowability dated Dec. 23, 2020 for U.S. Appl. No. 15/523,389 (pp. 1-3).
Corrected Notice of Allowability dated Oct. 19, 2020 for U.S. Appl. No. 16/081,605 (pp. 1-9).
Corrected Notice of Allowability dated Oct. 7, 2020 for U.S. Appl. No. 15/509,301 (pp. 1-6).
English translation of Chinese Office Action issued in App. No. CN201780025291.1, dated Apr. 9, 2022, 6 pages.
English translation of Chinese Office Action issued in App. No. CN201880057783.3, dated Dec. 2, 2021, 11 pages.
English translation of Chinese Office Action issued in App. No. CN20188086979, dated Mar. 24, 2023, 5 pages.

(56) References Cited

OTHER PUBLICATIONS

English translation of Japanese Office Action for App. No. JP2018-567587, dated Mar. 23, 2021, 4 pages.
English translation of Japanese Office Action issued in App. No. JP2018-567587, dated Jul. 5, 2022, 4 pages.
English translation of Japanese Office Action issued in App. No. JP2020-534895, dated Oct. 4, 2022, 3 pages.
European Patent Office Communication pursuant to Article 94(3) EPC for App. No. EP17763876.4, dated Aug. 19, 2020, 9 pages.
European Patent Office Communication pursuant to Article 94(3) EPC for App. No. EP17763876.4, dated Jan. 4, 2022, 8 pages.
European Patent Office Communication pursuant to Article 94(3) EPC for App. No. EP17763876.4, dated Jul. 25, 2023, 6 pages.
European Patent Office Communication pursuant to Article 94(3) EPC for App. No. EP17819487.4, dated Jun. 21, 2021, 5 pages.
European Patent Office Communication pursuant to Article 94(3) EPC issued in App. No. EP18853365, dated Feb. 1, 2023, 7 pages.
European Search Report and Written Opinion dated Jun. 12, 2018 for EP Application No. 158720441, 5 pages.
European Search Report dated Oct. 16, 2019 for EP Application No. 17763876.4, 11 pages.
European Search Report for EP15838477.6 dated Mar. 5, 2018, 5 pages.
International Search Report and Written Opinion issued in App. No. PCT/IL2023/051093, dated Dec. 21, 2023, 15 pages.
Korean Office Action issued in App. No. KR10-2020-7019407, dated May 17, 2024, 9 pages.
Korean Office Action issued in App. No. KR10-2020-7019407, dated May 17, 2024, 9 pages English computer translation.
Office Action (Final Rejection) dated Mar. 21, 2024 for U.S. Appl. No. 17/268,449 (pp. 1-13).
Office Action (Non-Final Rejection) dated Apr. 11, 2024 for U.S. Appl. No. 16/770,091 (pp. 1-20).
Office Action issued in App. No. IL275329, dated May 22, 2024, 5 pages.
EPO Communication pursuant to Article 94(3) issued in App. No. EP18890927.9, dated Sep. 19, 2024, 5 pages.
Korean Office Action issued in App. No. KR20217003264, dated Sep. 29, 2024, 8 pages.
Korean Office Action issued in App. No. KR20217003264, dated Sep. 29, 2024, 8 pages Google Translate English translation.

* cited by examiner

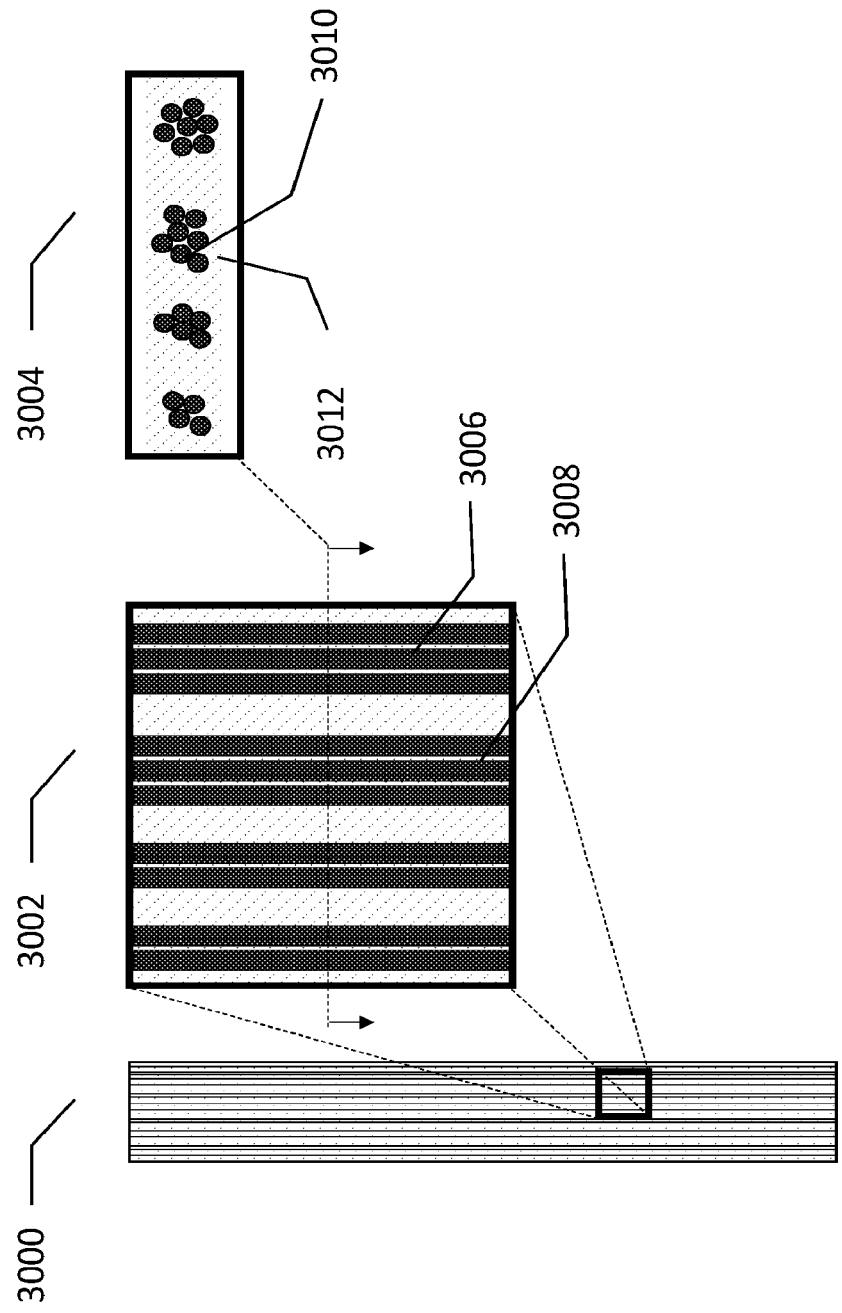
Figure 30. Continuous fiber reinforced composite tape

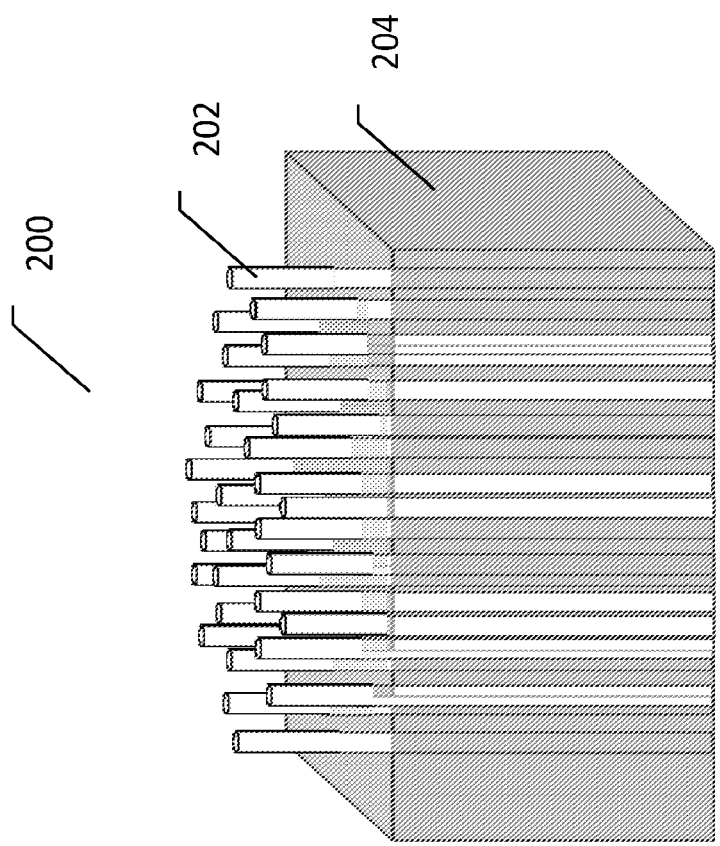
Figure 31. Cut-away, three-dimensional view of continuous fiber reinforced composite tape

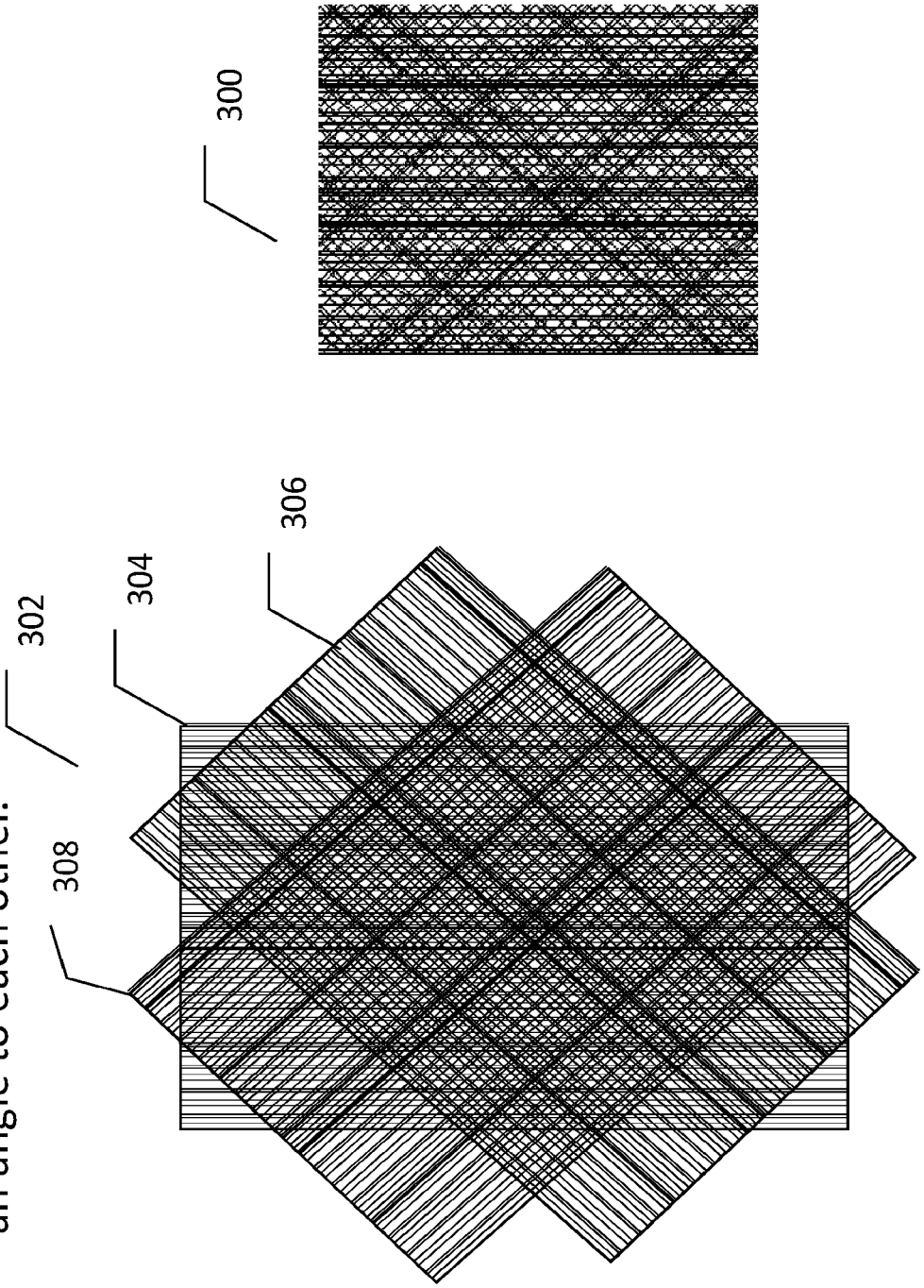
Figure 32a. Continuous-fiber reinforced sheet structure wherein sheet is comprised of multiple layers, each aligned at an angle to each other.

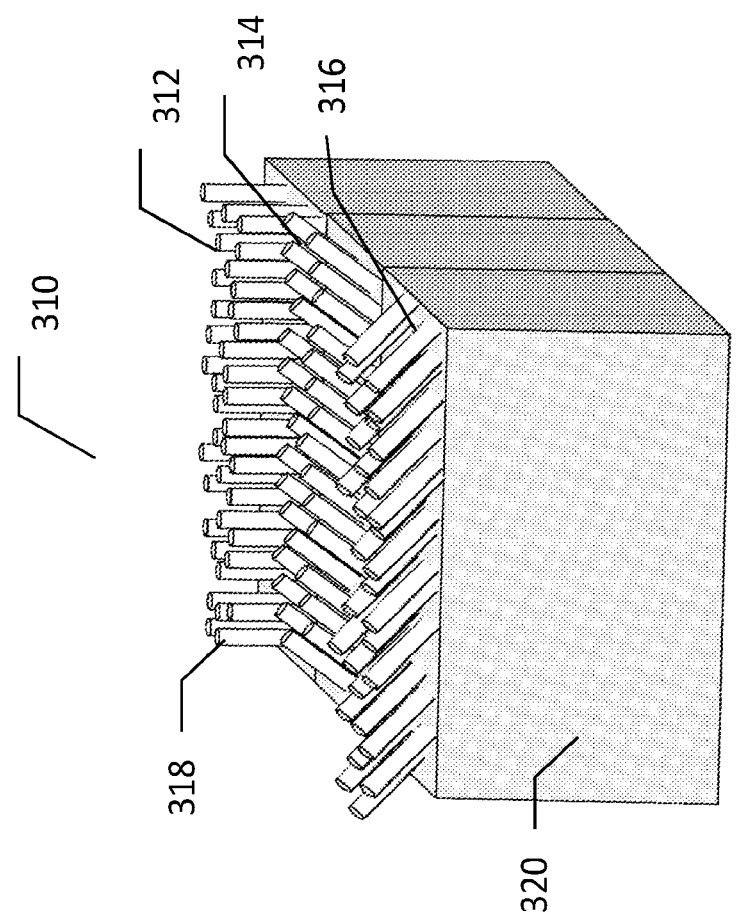
Figure 32b. Cut-away view of continuous-fiber reinforced sheet structure wherein sheet is comprised of multiple layers, each aligned at an angle to each other.

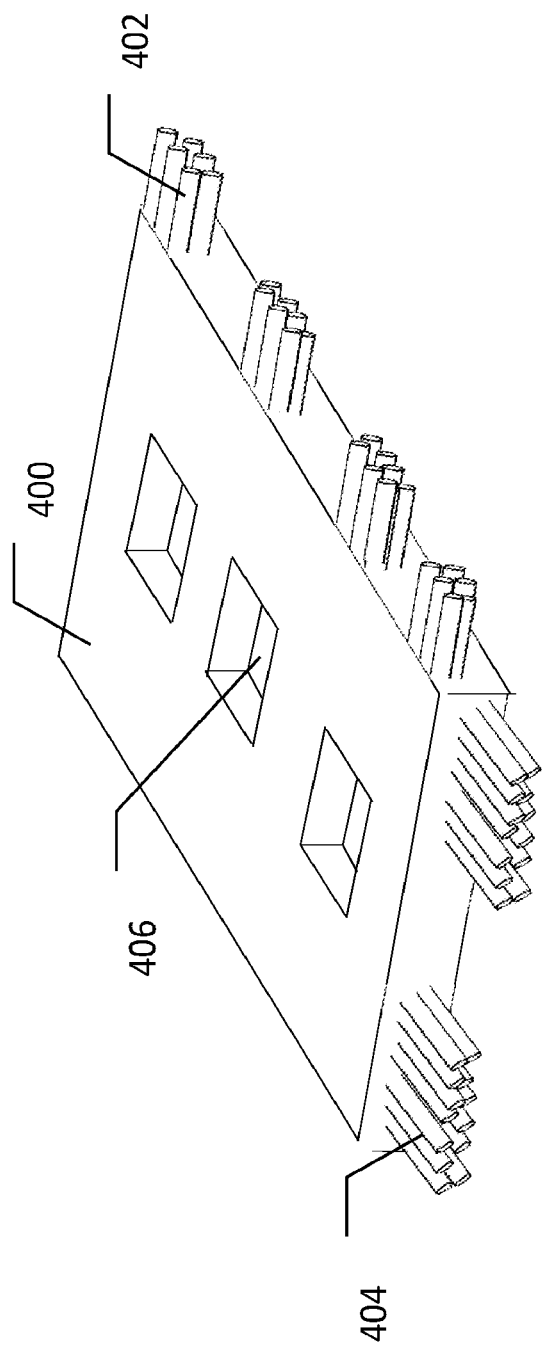
Figure 33. Continuous fiber reinforced medical implant wall with perforations to allow for tissue penetration

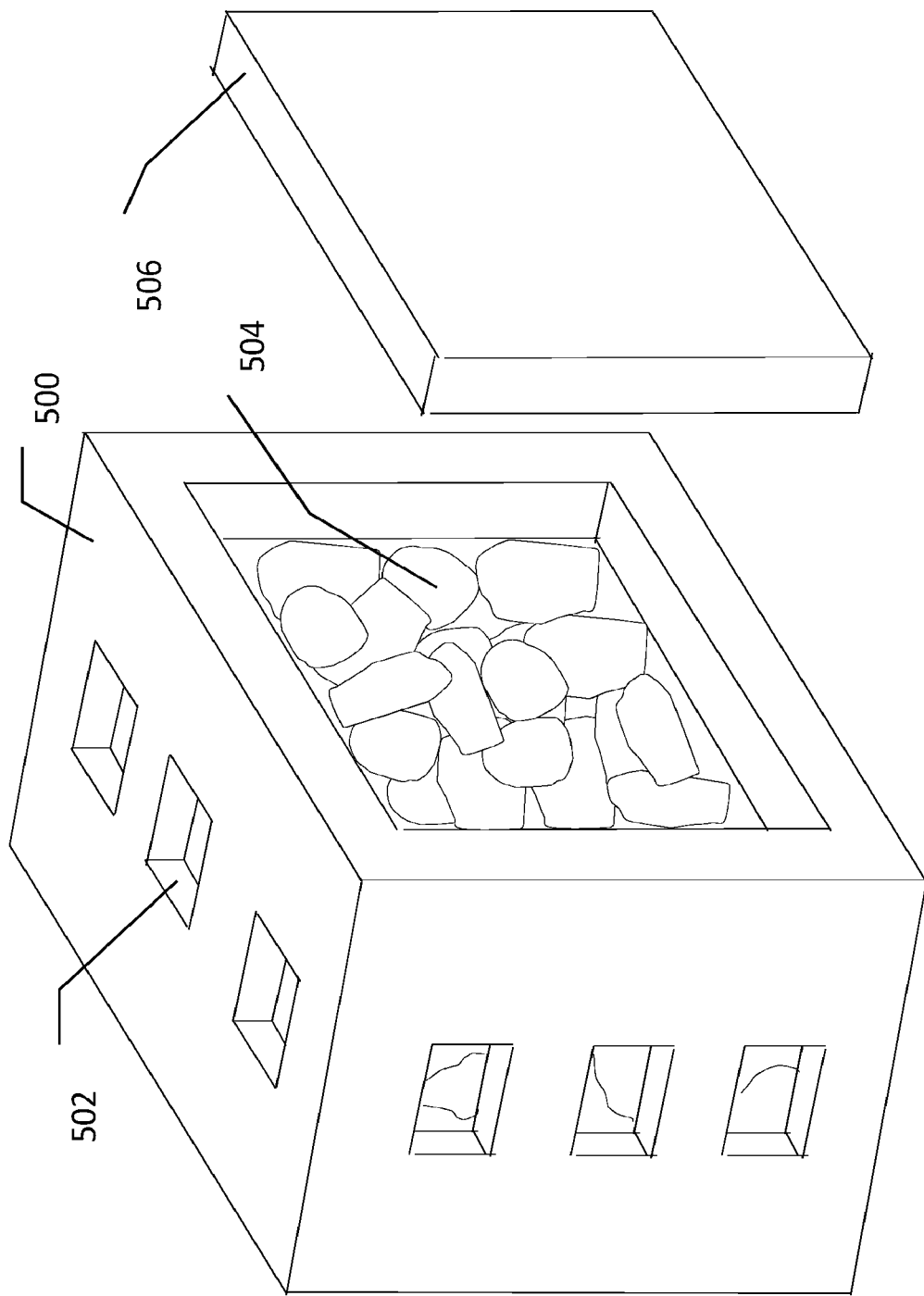
Figure 34. Bone filler cage

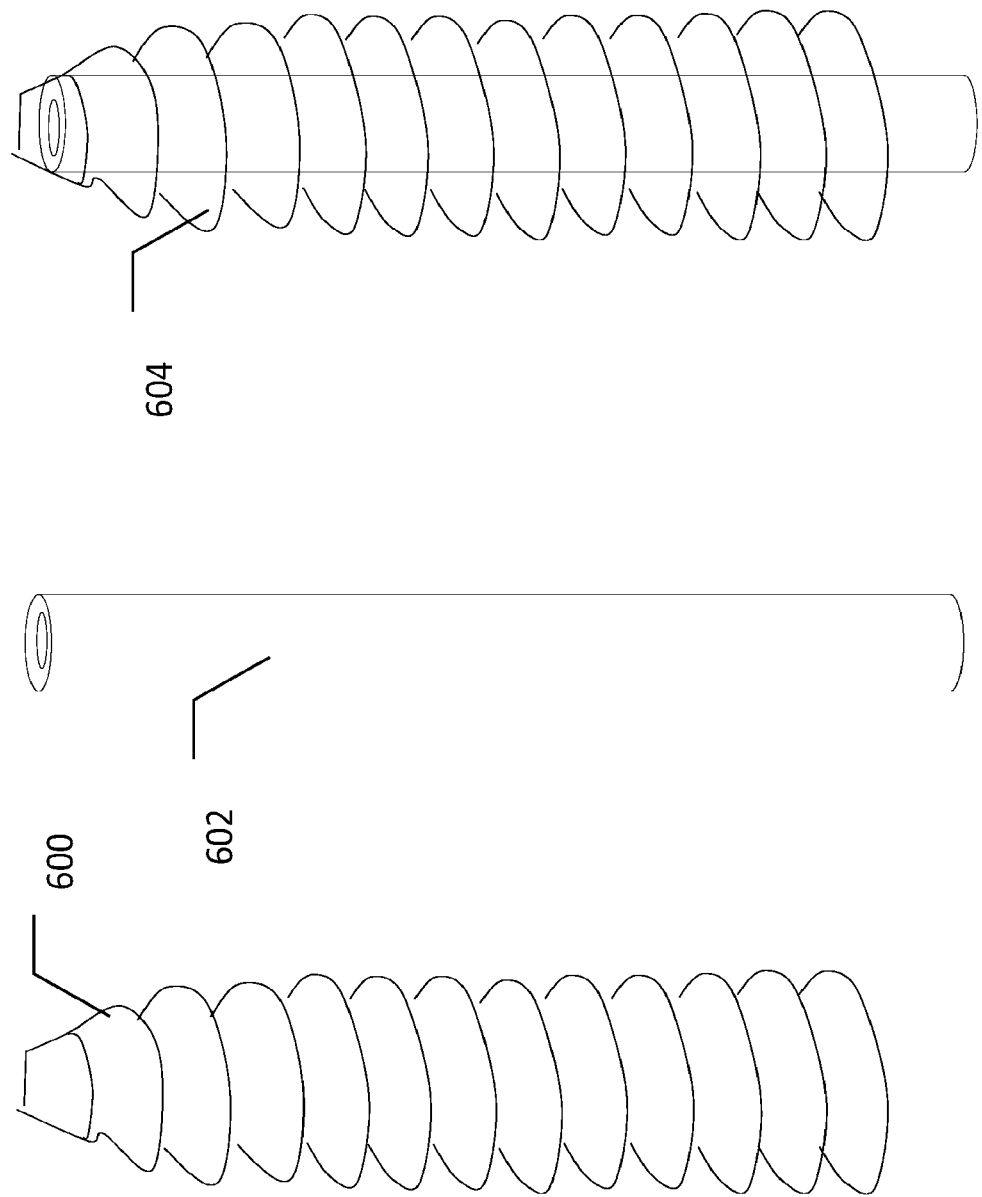
Figure 35. Continuous-fiber reinforced frame / backbone with non-reinforced polymer molded or printed on top

CONTINUOUS-FIBER REINFORCED BIOCOMPOSITE MEDICAL IMPLANTS

BACKGROUND

Permanent Orthopedic Implant Materials

Medical implants can be manufactured from metals, alloys, ceramics or both degradable and stable composites. In load-bearing, orthopedic applications that require high strength, usually stainless steel or titanium alloys are used. Metal implants have a long history of successful use in orthopedic surgery but also carry many risks for complications. Although these materials are inert, they are also used in situations in which the need for the implant is only temporary, like in fracture fixation. In the case of metal rods and plates for fracture fixation, a second surgery for device removal may be recommended about one year after confirmation of osseous union. Implant removal causes additional risk and added morbidity for the patient, occupies the availability of clinics, and increases the overall procedure costs. If the device is not removed, it may cause remodeling of the bone. Such remodeling may in turn weaken the bone due to stress shielding or inflammation of the host tissue. The stress shielding can occur due to the high stiffness (modulus) and strength of the metals compared to the stiffness and strength of the cortical bone, so that the metal stresses the bone, which can result in periprosthetic fractures or loss of bone strength.

Examples of load-bearing medical implants that have traditionally been constructed of metal alloys include bone plates, rods, screws, tacks, nails, clamps, and pins for the fixation of bone fractures and/or osteotomies to immobilize the bone fragments for healing. Other examples include cervical wedges, lumbar cages and plates and screws for vertebral fusion and other operations in spinal surgery.

Biostable polymers and their composites e.g. based on polymethacrylate (PMMA), ultra high molecular weight polyethylene (UHMWPE), polytetrafluoroethylene (PTFE), polyetheretherketone (PEEK), polysiloxane and acrylic polymers have also been used to manufacture medical implants. These materials are not biodegradable or bioresorbable and therefore face many of the same limitations as the metals when used for medical implant applications, for example they may require a second surgery for replacing or removing the implant at some point of the lifetime of the implant. Furthermore, these materials are weaker (less strong and stiff) than metal such that they are more susceptible to mechanical failure, particularly after repeated dynamic loading (i.e. through material fatigue or creep).

Existing Degradable Polymer Medical Implants

Resorbable polymers have been used to develop resorbable implants, which can also be referred to as absorbable, bioabsorbable, or biodegradable implants. The advantage of using biocompatible, resorbable polymers is that the polymers, and thus the implant, resorb in the body and release non-toxic degradation products that are metabolized by the metabolic system. Polymers, including polylactic and polyglycolic acids and polydioxanone, are resorbable biocompatible materials that are currently used as orthopedic plates, rods, anchors, pins or screws for non-load bearing medical implant applications, such as craniofacial applications. These medical implant materials offer the advantage of eventual resorption, eliminating the need for later removal, while allowing stress transfer to the remodeling fracture. However, current bioabsorbable materials and implants do not have mechanical properties to match metallic implants. The mechanical strength and modulus (approximately 3-5 GPa) of non-reinforced resorbable polymers, is insufficient to support fractured cortical bone, which has an elastic modulus in the range of approximately 15-20 GPa (Snyder S M, et al. measured the bending modulus of human tibial bone to be about 17.5 GPa Snyder S M Schneider E, *Journal of Orthopedic Research*, Vol. 9, 1991, pp. 422-431). Therefore, the indications of existing medical implants constructed from resorbable polymers are limited and their fixation usually requires protection from motion or significant loading. These devices are only a consideration when fixation of low stress areas is needed (i.e. non-load bearing applications) such as in pediatric patients or in medial malleolar fractures, syndesmotic fixation, maxillofacial, or osteochondral fractures in adults.

Reinforced Degradable Polymer Materials

Recently, reinforced polymer materials with improved strength and stiffness (modulus) have been introduced. These biodegradable composites comprise polymers reinforced by fillers, usually in fiber form. In composite materials, usually a relatively flexible matrix (i.e. a polymer) is combined with a stiff and strong reinforcement material to enhance the mechanical properties of the composite matrix. For example, biodegradable glass or mineral material can be used to improve the stiffness and strength of a biodegradable polymer matrix. In the prior art, several attempts to produce such a composite were reported where bioactive glass particles, hydroxyapatite powder, or short glass fibers were used to enhance the properties of a biodegradable polymer. In most cases, the strength and stiffness of these composites is lower than cortical bone or becomes lower than cortical bone following rapid degradation in a physiological environment. Therefore, the majority of these composite materials are not appropriate for use in load-bearing medical implant applications. However, biodegradable composites with strength and stiffness equivalent to or greater than cortical bone have recently been reported, for example a biodegradable composite comprising a biodegradable polymer and 20-70 vol % glass fibers (WO2010128039 A1). Other composite material implants, for example formed of polymer reinforced with fibers, are disclosed in U.S. Pat. Nos. 4,750,905, 5,181,930, 5,397,358, 5,009,664, 5,064,439, 4,978,360, 7,419,714, the disclosures of which are incorporated herein by reference Degradation Mechanism of Reinforced Degradable Polymer Materials When biodegradable composites are used for load-bearing medical implant applications, such as to fixate bone fractures, the mechanical properties of the medical implant must be retained for an extended period. Degradation of the composite will result in premature loss of implant strength or stiffness and can lead to implant function failure, such as insufficient fixation of bone segments resulting in improper bone healing.

Unfortunately, biodegradable composites will begin to hydrolytically degrade once they come into contact with body fluid. This degradation can be a result of degradation of the biodegradable polymer, reinforcing filler, or both. Such degradation in an aqueous environment, such as the physiological environment, can particularly result in a sharp drop-off of mechanical strength and stiffness in certain reinforced polymer materials that are reinforced by inorganic compounds. Where the absorbable polymer matrix is organic material, and the fillers are inorganic compounds, the adhesion between the absorbable polymer matrix and the filler may be reduced by degradation of either the polymer or filler in the aqueous environment and become rapidly reduced such that the initial mechanical properties of the reinforced polymer drop-off rapidly and become less than desirable for adequate load-bearing performance. Aside from the degradation of the polymer and filler separately, poor polymer to reinforcement interface interaction and adhesion can result in early failure at the interface in a aqueous environment, thereby resulting in sharp mechanical property drop off as the reinforcement detaches from the polymer and the reinforcing effect of the filler is lost.

Törmälä et al. (WO 2006/114483) described a composite material containing two reinforcing fibers, one polymeric and one ceramic, in a polymer matrix and reported good initial mechanical results (bending strength of 420+/−39 MPa and bending modulus of 21.5 GPa) equivalent to the properties of cortical bone. However, the prior art teaches that bioabsorbable composites reinforced with absorbable glass fibers, have a high initial bending modulus but that they rapidly lose their strength and modulus in vitro.

While improved interfacial bonding (such as covalent bonding) between the polymer and reinforcement can significantly prolong reinforced bioabsorbable polymer mechanical property retention in an aqueous environment (WO2010128039 A1), continued hydrolysis of the polymer, reinforcement, or interface between the two will result in loss of mechanical properties over time. Since osseous union may take several months or longer, even the prolonged mechanical property degradation profile in covalently bonded reinforced bioabsorbable polymers may be insufficient for optimal function of medical implants used for load-bearing orthopedic applications.

An example of strength loss in a reinforced degradable polymer implant is described with regard to self-reinforced poly-L-lactic acid (Majola A et al., *Journal of Materials Science Materials in Medicine*, Vol. 3, 1992, pp. 43-47). There, the strength and strength retention of self-reinforced poly-L-lactic acid (SR-PLLA) composite rods were evaluated after intramedullary and subcutaneous implantation in rabbits. The initial bending strength of the SR-PLLA rods was 250-271 MPa. After intramedullary and subcutaneous implantation of 12 weeks the bending strength of the SR-PLLA implants was 100 MPa.

Co- and terpolyesters of PLA, PGA and PCL are of interest in the tailoring of the optimal polymer for resorbable composite material for medical devices. The choice of monomer ratio and molecular weight significantly affects the strength elasticity, modulus, thermal properties, degradation rate and melt viscosity of resorbable composite materials and all of these polymers are known to be degradable in aqueous conditions, both in vitro and in vivo. Two stages have been identified in the degradation process: First, degradation proceeds by random hydrolytic chain scission of the ester linkages which decreases the molecular weight of the polymers. In the second stage measurable weight loss in addition to chain scission is observed. The mechanical properties are mainly lost or at least a remarkable drop will be seen in them at the point where weight loss starts. Degradation rate of these polymers is different depending on the polymer structure: crystallinity, molecular weight, glass transition temperature, block length, racemization and chain architecture. (Middleton J C, Tipton A J, *Biomaterials* 21, 2000, 2335-2346)

SUMMARY OF THE INVENTION

There is a great need for a reinforced bioabsorbable polymer material exhibiting improved mechanical properties for use in load-bearing medical implant applications, such as structural fixation for load-bearing purposes, where the high strength and stiffness of the implant are retained at a level equivalent to or exceeding cortical bone for a period at least as long as the maximum bone healing time.

The construction of biocomposite fiber-reinforced materials with the requisite high strength and stiffness is known in the art to be a difficult problem, which so far has not been provided with an adequate solution.

Specifically within such fiber-reinforced composites, achieving the high strengths and stiffness required for many medical implant applications can require the use of continuous-fiber reinforcement rather than short or long fiber reinforcement. This creates a significant difference from the implant structures, architectures, designs, and production techniques that have been previously used with medical implants produced from polymers or composites comprising short or long fiber reinforced polymers. Those implants are most commonly produced using injection molding, or occasionally 3-D printing, production techniques. The production of these implants generally involves homogeneity of the material throughout the implant and the finished implant is then comprised of predominantly isotropic material. However, with continuous fiber-reinforcement, the fibers must be carefully aligned such that each fiber or bundle of fibers runs along a path within the composite material such that they will provide reinforcement along specific axes within the implant to provide stress resistance where it is most needed.

Unlike with bulk materials, the properties of parts made from composite materials are highly dependent on the internal structure of the part. This is a well-established principle in the design of parts from composite materials where the mechanical properties of fiber-reinforced composite materials are known to be dependent on the angles and orientations of the fibers within the composite parts.

The vast majority of prior composite material part design focused exclusively on the mechanical properties of the parts. However, these parts were permanent parts and not degradable or absorbable. Therefore, no attention had to be given to the mechanisms of degradation or absorption of the composite materials within the part. Even previous orthopedic implants comprised of composite materials have largely adhered to these same classical composite material design principles.

However, the herein invention relates to medical implants comprised of a new class of composite materials that are biocompatible and in many cases are bioabsorbable. The design challenges in creating medical implants with these materials involve consideration of many more aspects and parameters than just the mechanical properties that have previously been considered with composite material parts.

Furthermore, with regard to bioabsorbable continuous fiber-reinforced composite implants, the degradation profile of the composite material within the implant must also be taken into consideration in ensuring that the continuous fibers will provide strength and stiffness reinforcement both initially at the initial time of device implantation and also over the course of its functional period within the body.

Mechanical properties that are critical to the performance of medical implants in the herein invention include: flexural, tensional, shear, compressional, and torsional strength and stiffness (modulus). In these bioabsorbable medical implants, these properties are critical both at time zero (i.e. in the implant following production) and following a period of implantation in the body. As with previously described parts made from fiber-reinforced composite material, the mechanical properties at time zero are dependent on the alignment and orientation of fibers within the part. However, retaining a large percentage of the mechanical properties following implantation in the body (or simulated implantation) requires additional and different considerations.

As will be described in more detail below, such considerations for the medical implant design can include the following parameters: compositions, component ratios, fiber diameters, fiber distribution, fiber length, fiber alignments and orientations, etc.

These parameters can impact several additional aspects and properties of the herein described medical implant performance:
1. Material degradation rate (degradation products, local pH and ion levels during degradation)
2. Surface properties that affect interface of implant with surrounding local tissue
3. Biological effects such as anti-microbial or osteoconductive properties
4. Response to sterilization processes (such as ethylene oxide gas, gamma or E-beam radiation)

The present invention provides a solution to these problems by providing, in at least some embodiments, implant compositions from continuous-fiber reinforced biocompatible composite materials that are a significant step forward from previous implants in that they can achieve sustainably high, load bearing strengths and stiffness. Additionally, many embodiments of the present invention additionally facilitate these high strength levels with efficient implants of low volume. Furthermore, the biocomposite materials described herein are also optionally and preferably bioabsorbable.

The present invention therefore overcomes the limitations of previous approaches and provides medical implants comprising (optionally biodegradable) biocomposite compositions featuring continuous fiber-reinforcement that retain their mechanical strength and stiffness for an extended period.

According to at least some embodiments, there is provided a medical implant comprising a plurality of biocomposite layers, said layers comprising a polymer, which is optionally biodegradable, and a plurality of uni-directionally aligned continuous reinforcement fibers. Optionally and preferably, the biodegradable polymer is embodied in a biodegradable composite. Also optionally and preferably, the fibers are embedded in a polymer matrix comprising one or more bioabsorbable polymers.

According to at least some embodiments, the composite layers are each comprised of one or more composite tapes, said tape comprising a polymer, which is optionally biodegradable, and a plurality of uni-directionally aligned continuous reinforcement fibers. Optionally and preferably, the biodegradable polymer is embodied in a biodegradable composite. Also optionally and preferably, the fibers are embedded in a polymer matrix comprising one or more bioabsorbable polymers.

Optionally and preferably, the fiber-reinforced biodegradable composite within the implant has a flexural modulus exceeding 10 GPa and flexural strength exceeding 100 MPa.

Preferably, the fiber-reinforced biodegradable composite within the implant has flexural strength in range of 400-800 MPa, more preferably 650-800 MPa. Elastic modulus in range of 10-27 GPa. More preferably 16-27 GPa.

Preferably, the fiber-reinforced composite within the implant has strength retention of Elastic Modulus above 10 GPa after 8 weeks implantation and flexural strength above 150 MPa after 8 weeks.

The term "biodegradable" as used herein also refers to materials that are resorbable, bioabsorbable or absorbable in the body.

BRIEF DESCRIPTION OF THE DRAWINGS

FIG. 30 shows an example of a continuous fiber-reinforced tape of the type that can be used to form a layer in a medical implant comprised of continuous fiber-reinforced layers.

FIG. 31 shows an example of a cut-away, three-dimensional view of a continuous fiber-reinforced tape (200).

FIG. 32a shows an example of a top-view of a reinforced bioabsorbable composite sheet (300) comprised of three layers of uni-directional fibers at different angles.

FIG. 32b shows an example of a cut-away view of a reinforced bioabsorbable composite structure (310) comprised of three layers of uni-directional fibers at different angles.

FIG. 33 shows an example of the wall of a continuous-fiber reinforced composite medical implant.

FIG. 34 shows an example of a bone filler cage that consists of continuous-fiber reinforced composite medical implant walls (500) that additionally contains perforations (502) to allow tissue and cellular ingrowth into the bone filler material (504) contained within the bone filler cage.

FIG. 35 shows an example of a bioabsorbable cannulated screw (600) that is a medical implant.

DETAILED DESCRIPTION

A medical implant according to at least some embodiments of the present invention is suitable for load-bearing orthopedic implant applications and comprises one or more biocomposite, optionally bioabsorbable, materials where sustained mechanical strength and stiffness are critical for proper implant function and wherein the implant is additionally comprised of a moisture barrier coating that restricts or eliminates fluid exchange into the implant.

The present invention, according to at least some embodiments, thus provides medical implants that are useful as structural fixation for load-bearing purposes, exhibiting sustained mechanical properties as a result of impeded degradation of the bioabsorbable materials that comprise the implant.

Relevant implants may include bone fixation plates, intramedullary nails, joint (hip, knee, elbow) implants, spine implants, and other devices for such applications such as for fracture fixation, tendon reattachment, spinal fixation, and spinal cages.

According to at least some embodiments, the herein invention relates to medical implants comprised of a biocomposite material composition. Preferably the biocomposite material composition is comprised of (an optionally bioabsorbable) polymer reinforced by a mineral composition. Preferably the mineral composition reinforcement is provided by a reinforcing fiber made from the mineral composition.

Preferably, the medical implant or part thereof is comprised of a number of biocomposite layers, each layer being comprised of bioabsorbable polymer reinforced by uni-directional reinforcing fibers. The properties of the implant are optionally and preferably determined according to the layer composition and structure, and the placement of the layers in regard to the device, for example with regard to layer direction. The fibers may optionally remain discrete but optionally some melting of the polymer may occur to bind the layers together.

Figure 7:
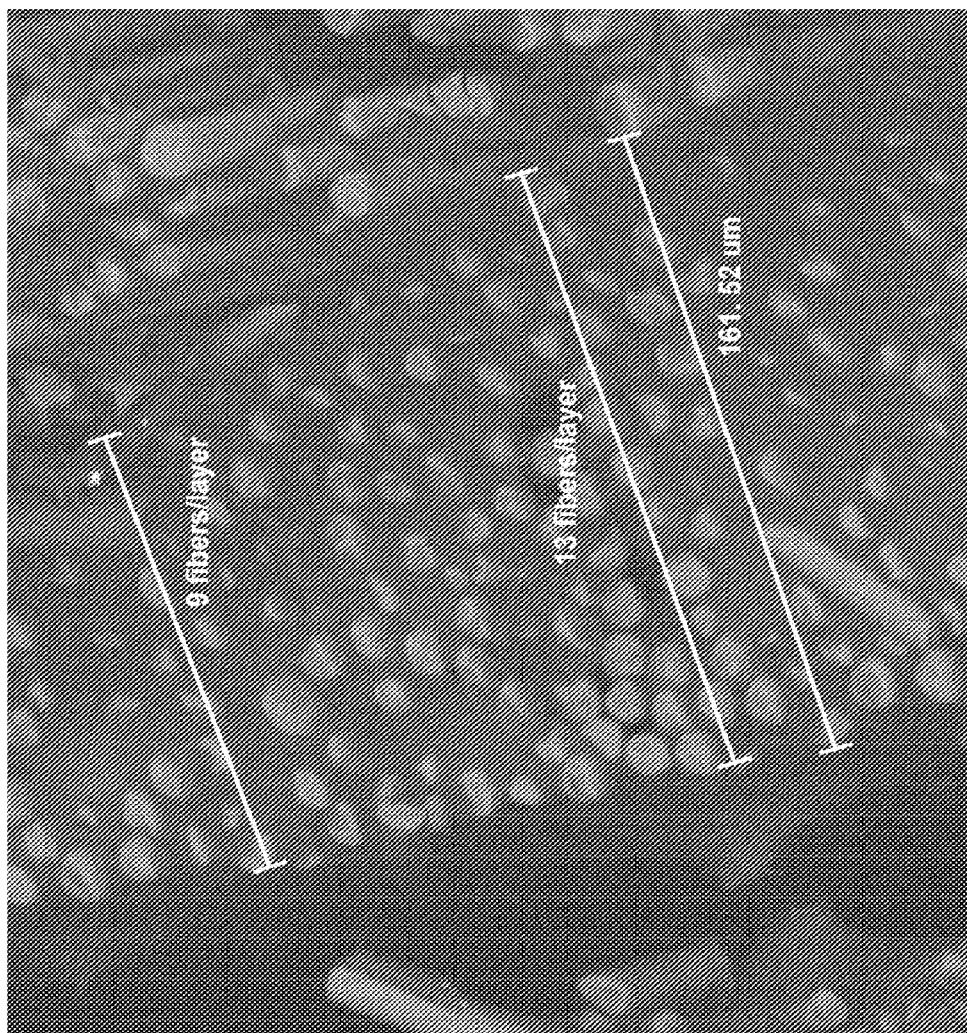
FIG. 7: Scanning Electron Microscope (SEM) image using a Back-Scattered Electrons (BSE) detector of a cross section of a 6 mm pin with 70% fiber content by weight, such as those described in Example 1. Magnification of this image is 500×. This image shows a magnification of the cross section of reinforcing mineral fibers embedded within bioabsorbable polymer matrix.
Figure 10:
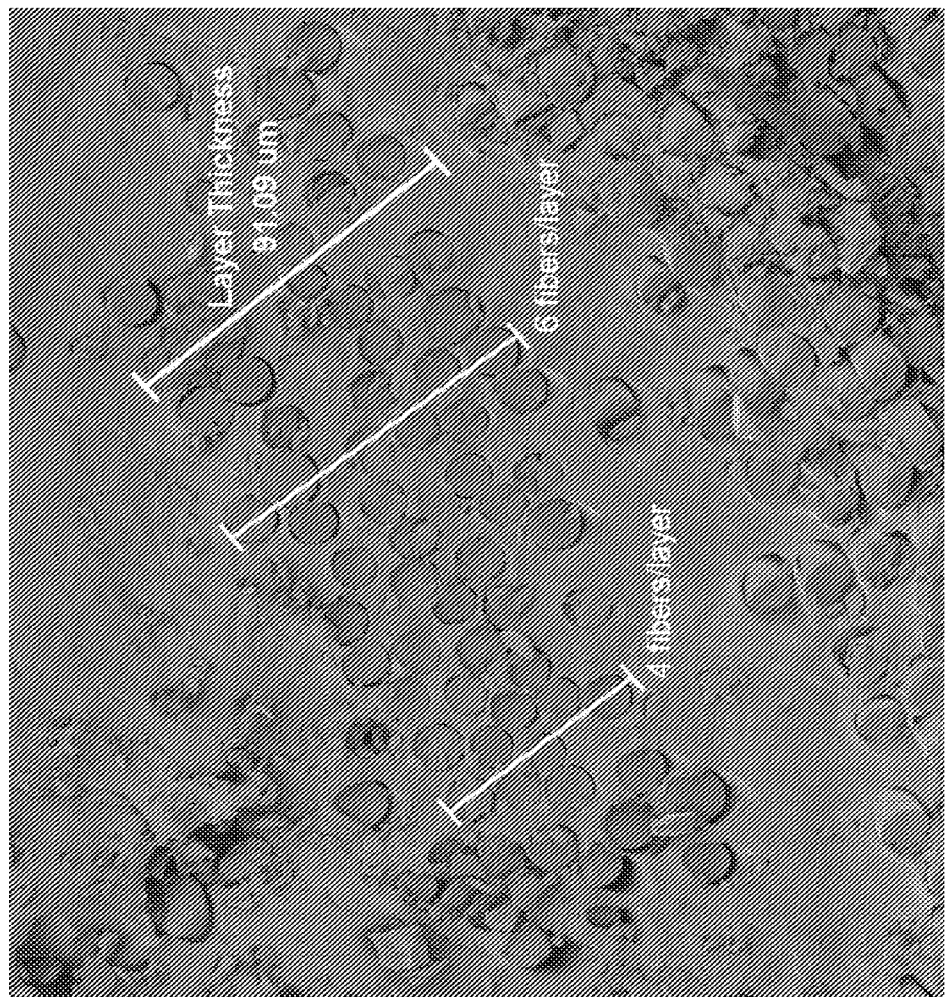
FIG. 10: Scanning Electron Microscope (SEM) image using a secondary electron detector of Au sputtered cross section of a 2 mm pin with 50% fiber content by weight, such as those described in Example 2. Magnification of this image is 1,000×. This image shows a magnification of the cross section of reinforcing mineral fibers embedded within bioabsorbable polymer matrix.
Figure 20:
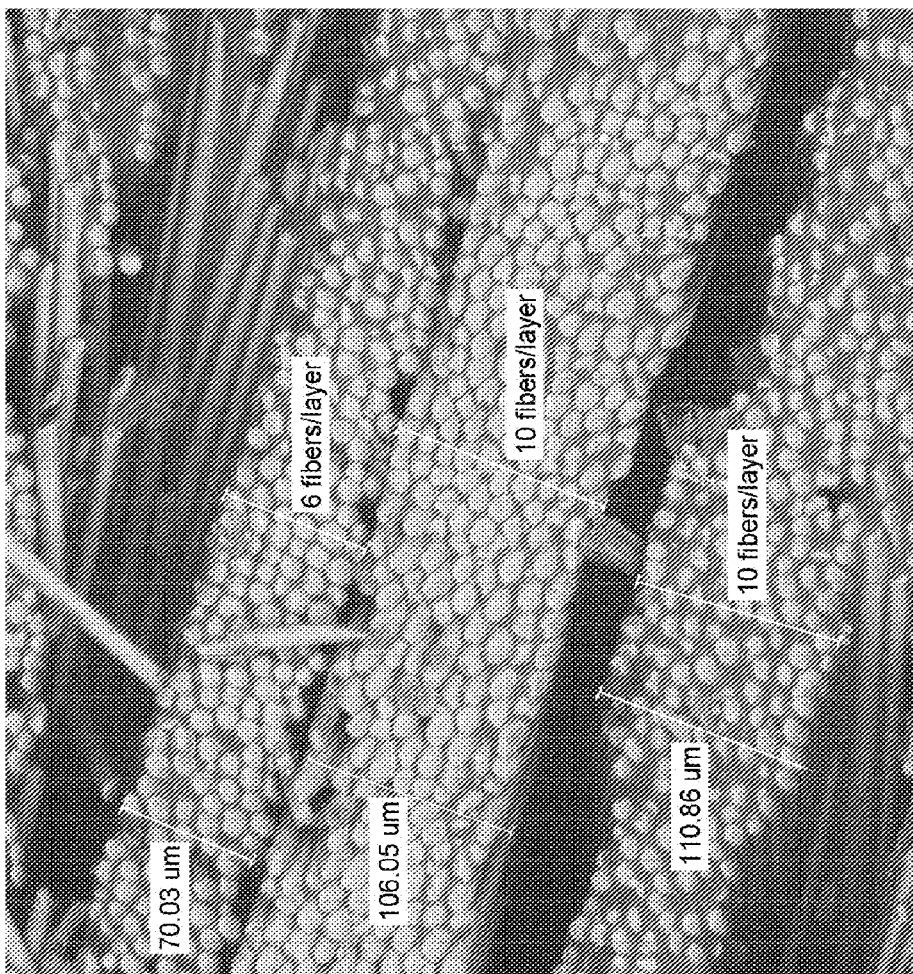
FIG. 20: Scanning Electron Microscope (SEM) image using a Back-Scattered Electrons (BSE) detector of a cross section of a 2 mm plate with 70% fiber content by weight, such as those described in Example 3. Magnification of this image is 250×. This image shows a magnification of the cross section of reinforcing mineral fibers embedded within bioabsorbable polymer matrix.

A biocomposite layer can be defined as a continuous or semi-continuous stratum running through part or all of a medical implant, wherein the layer is comprised of reinforcing fibers that aligned uni-directionally. Layers can be seen in several figures showing the internal structure of reinforced biocomposite medical implants, including in FIGS. 7, 10, and 20.

Preferably, there are between 1-100 reinforcing fibers forming the thickness of each biocomposite layer. Preferably, there are between 2-40 reinforcing fibers in each layer thickness and most preferably there are between 4-20 reinforcing fibers.

Figure 26:
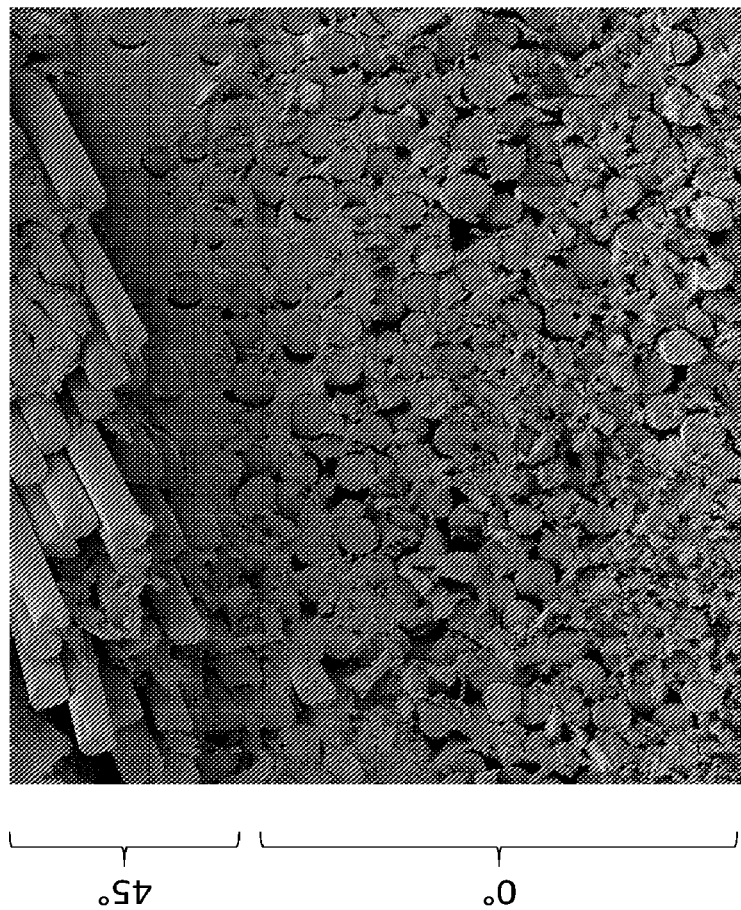
FIG. 26: Scanning Electron Microscope (SEM) image using a secondary electron detector of Au sputtered cross section of a 2 mm cannulated pin with 50% fiber content by weight, such as those described in Example 2. Magnification of this image is 1000×. This image shows a magnification of the cross section of reinforcing mineral fibers, embedded within bioabsorbable polymer matrix layers in alternating 0° and 45° orientation.
Figure 27:
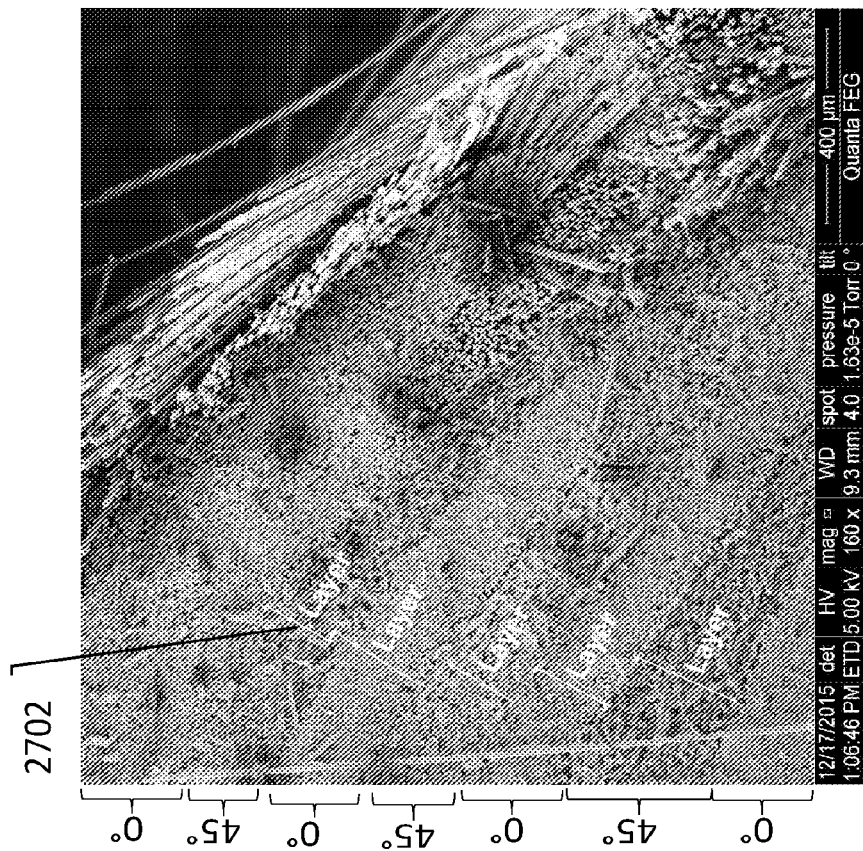
FIG. 27: Scanning Electron Microscope (SEM) image using a secondary electron detector of Au sputtered cross section of a 6 mm pin with 85% fiber content by weight, such as those described in Example 1. Magnification 160×. This image shows a magnification of the cross section of reinforcing mineral fibers, embedded within layers 2702 in alternating 0° and 45° orientation, with little or no bioabsorbable polymer matrix separating the layers.

Optionally, the directional fiber orientation between adjacent layers within the implant alternates between layers such that each adjacent layer is out of phase (of a different angle) from the layer that is adjacent to it. Preferably, the average or median angle difference between layers is between 15 to 75 degrees, more preferably between 30 to 60 degrees, and most preferably between 40 to 50 degrees. Microscopic images of such out of phase adjacent biocomposite layers can be seen in FIGS. 26 and 27.

Preferably, the biocomposite layers within the medical implant are well approximated to each other. More preferably, the distance between layers, as measured by the distance between the last fiber in one layers and the first fiber in the subsequent layer is between 0-200 µm, more preferably between 0-60 µm, 1-40 µm, and most preferably between 2-30 µm. Good approximation of the fibers within a layer to the fibers within the adjacent layer allow each layer to mechanically support the adjacent layer. However, some distance between the layers may be desirable to allow for some polymer to remain between the fibers of adjacent layers and thus adhere the layers together, prevent layer dehiscence under high mechanical load.

Figure 22:
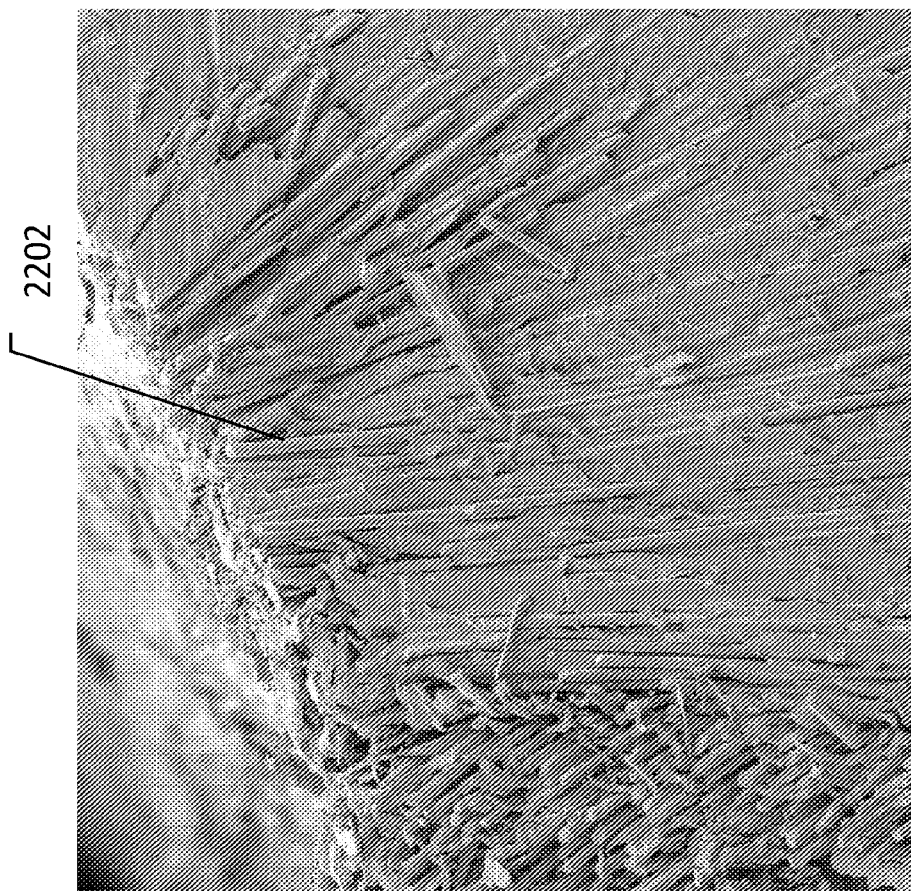
FIG. 22: Scanning Electron Microscope (SEM) image using a secondary electron detector of Au sputtered cross section of a 2 mm pin with 50% fiber content by weight, such as those described in Example 2. Magnification of this image is 300×. This image shows a magnification of the longitudinal axis of reinforcing mineral fibers 2202.

The reinforcing fibers are preferably continuous fibers. Said continuous fibers are preferably longer than 4 mm, more preferably longer than 8 mm, 12 mm, 16 mm, and most preferably longer than 20 mm. A microscopic image of such continuous fibers can be seen in FIG. 22.

Alternatively, or in addition, the reinforcing fiber length can be defined as a function of implant length wherein at least a portion of the reinforcing fibers, and preferably a majority of the reinforcing fibers, are of a continuous length at least 50% the longitudinal length of the medical implant or medical implant component that is comprised of these fibers. Preferably, the portion or majority of the reinforcing fibers are of continuous length at least 60% of the length of the medical implant, and more preferably at least 75% of the length of the medical implant. Such continuous reinforcing fibers can provide structural reinforcement to a large part of the implant.

The diameter of reinforcing fiber for use with herein reinforced biocomposite medical implant can be in the range of 0.1-100 µm. Preferably, fiber diameter is in the range of 1-20 µm. More preferably, fiber diameter is in the range of 4-16 µm.

The standard deviation of fiber diameter between fibers within the medical implant is preferably less than 5 µm, more preferably less than 3 µm, and most preferably less than 1.5 µm. Uniformity of fiber diameter is beneficial for consistent properties throughout the implant.

Optionally, the distance between adjacent reinforcing fibers within a biocomposite layer is in the range of 0.5-50 µm, preferably the distance between adjacent fibers is in the range of 1-30 µm, more preferably in the range of 1-20 µm, and most preferably in the range of 1-10 µm.

Preferably, the weight percentage of reinforcing fibers within the biocomposite medical implant is in the range of 20-90%, more preferably the weight percentage is in the range of 40%-70% Preferably, the volume percentage of reinforcing fibers within the biocomposite medical implant is in the range of 30-90%, more preferably the weight percentage is in the range of 40%-70%.

While the biocomposite composition within the implant is important in determining the mechanical and bulk properties of the implant, the specific composition and structure that comes into contact with the surface edge of the implant has unique significance in that this composition and structure can greatly affect how surrounding cells and tissue interact with the implant following implantation into the body. For example, the absorbable polymer part of the biocomposite may be hydrophobic in nature such that it will repel surrounding tissues to a certain degree while the mineral reinforcing fiber part of the biocomposite may be hydrophilic in nature and therefore encourage surrounding tissues to attach to the implant or create tissue ingrowth.

Figure 25:
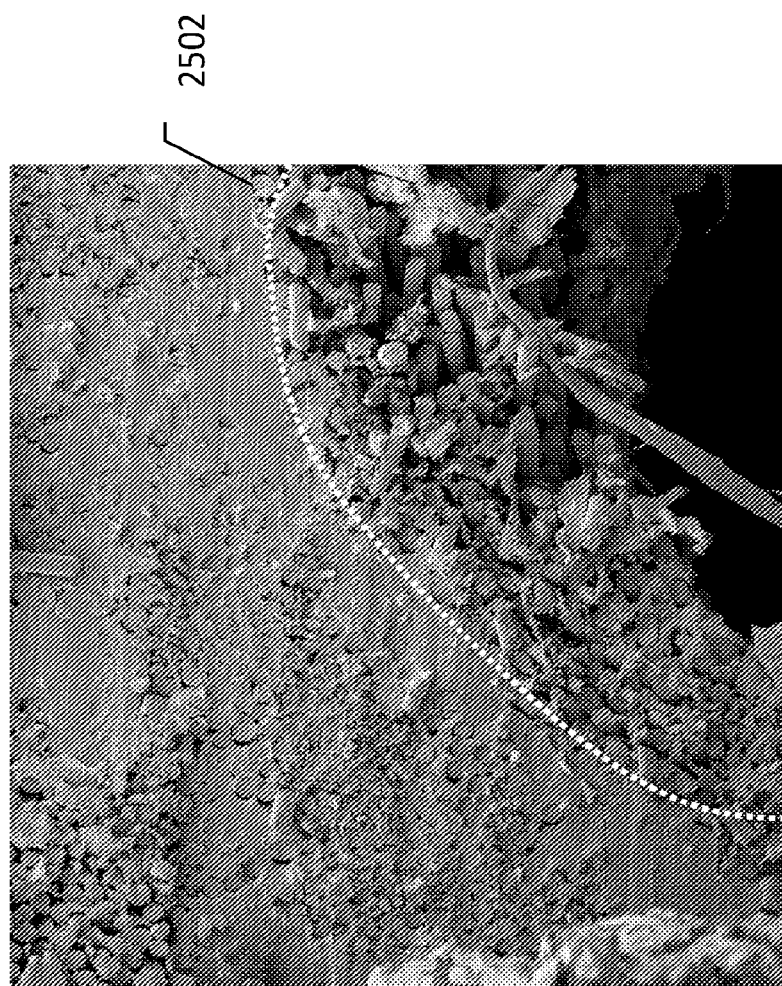
FIG. 25: Scanning Electron Microscope (SEM) image using a secondary electron detector of Au sputtered cross section of a 2 mm cannulated pin with 50% fiber content by weight, such as those described in Example 2. Magnification of this image is 500×. This image shows a magnification of the cross section of reinforcing mineral fibers surrounding the inner cannulation of the pin 2502.
Figure 29:
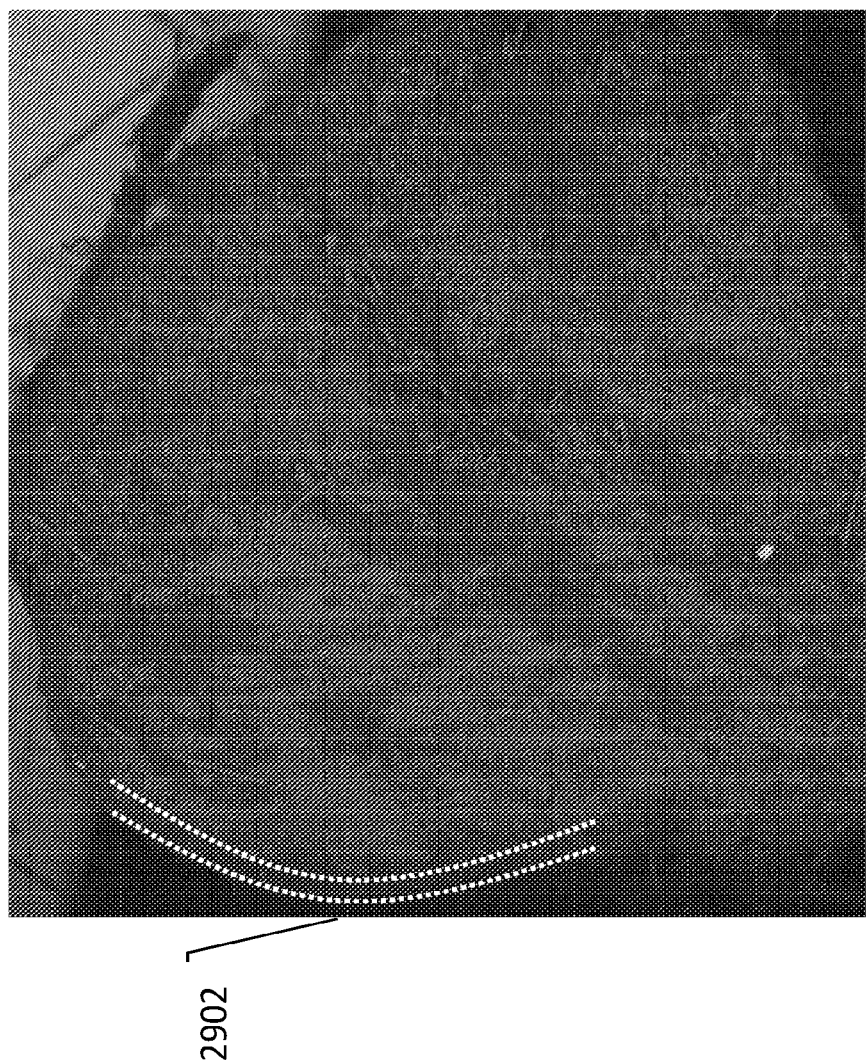
FIG. 29: Scanning Electron Microscope (SEM) image using a Back-Scattered Electrons (BSE) detector of a cross section of a 2 mm pin with 50% fiber content by weight, such as those described in Example 2. Magnification 60×. This image shows a magnification of the edge of the pin, indicating that the bioabsorbable polymer is present at the outer surface of the implant 2902.

In an optional embodiment of the herein invention, the surface presence of one of the compositional components by percentage of surface area is greater than the presence of that component in the bulk composition of the implant by volume percentage. For example, the amount of mineral on the surface might be greater than the amount of polymer, or vice versa. Without wishing to be limited by a single hypothesis, for greater integration with bone, a greater amount of mineral would optionally and preferably be present on the surface. For reduced integration with bone, a greater amount of polymer would optionally and preferably be present on the surface. Preferably, the percentage of surface area composition of one component is more than 10% greater than the percentage of volume percentage of that component in the overall biocomposite implant. More preferably, the percentage is more than 30% greater, and most preferably more than 50% greater. FIG. 25 shows a microscopic image of a biocomposite medical implant with a predominance of mineral reinforcing fiber along the inner surface area edge of the implant. FIG. 29 shows a microscopic image of a biocomposite medical implant with a predominance of bioabsorbable polymer along the outer surface area of the implant.

Optionally, one surface of the medical implant may have a local predominance of one of the biocomposite components while a different surface, or different part of the same surface, may have a local predominance of a different biocomposite component.

Optionally, the medical implant is a threaded screw or other threaded implant. Preferably, the outer layer of the implant will be directionally aligned such that the direction of the fibers approximates the helix angle of the threading. Preferably, the alignment angle of the fiber direction is within 45 degrees of the helix angle. More preferably, the alignment angle is within 30 degrees, and most preferably the alignment angle is within 15 degrees of the helix angle. Approximating the fiber alignment angle to the helix angle in this manner can improve the robustness of the threading and prevent dehiscence of the reinforcing fibers within the threading.

Figure 23:
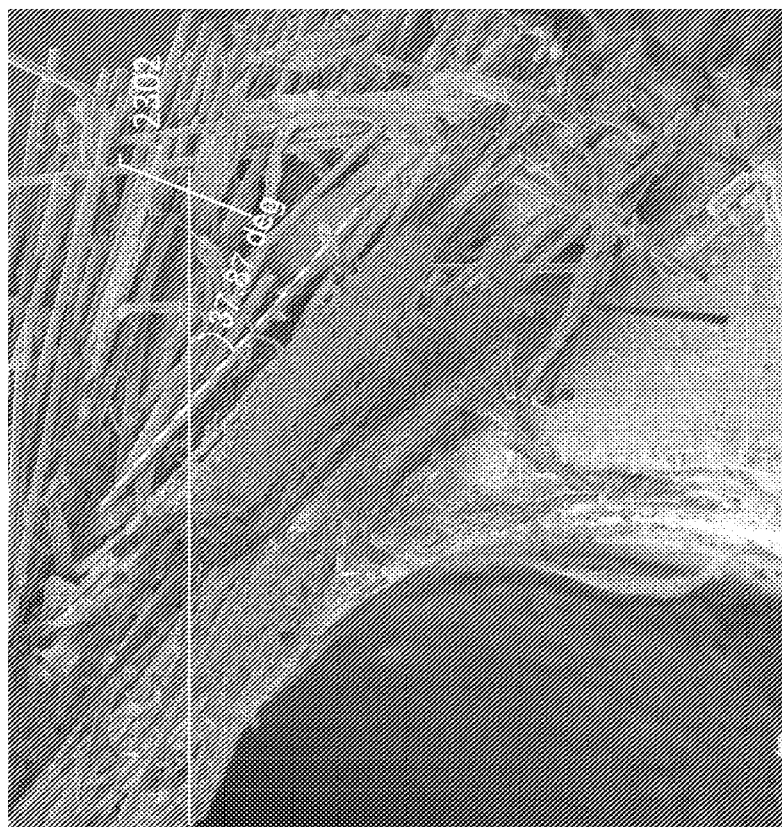
FIG. 23: Scanning Electron Microscope (SEM) image using a secondary electron detector of Au sputtered cross section of a 2 mm cannulated pin with 50% fiber content by weight, such as those described in Example 2. Magnification of this image is 250×. This image shows a magnification of the cannulated portion and the continuous, reinforcing mineral fibers. The tangential angle 2302 is defined as the deviation from the direction of the curve at a fixed starting point, where the fixed starting point is the point where the fiber touches or is closest to coming into contact with the center of the cross-sectional circular area.
Figure 24:
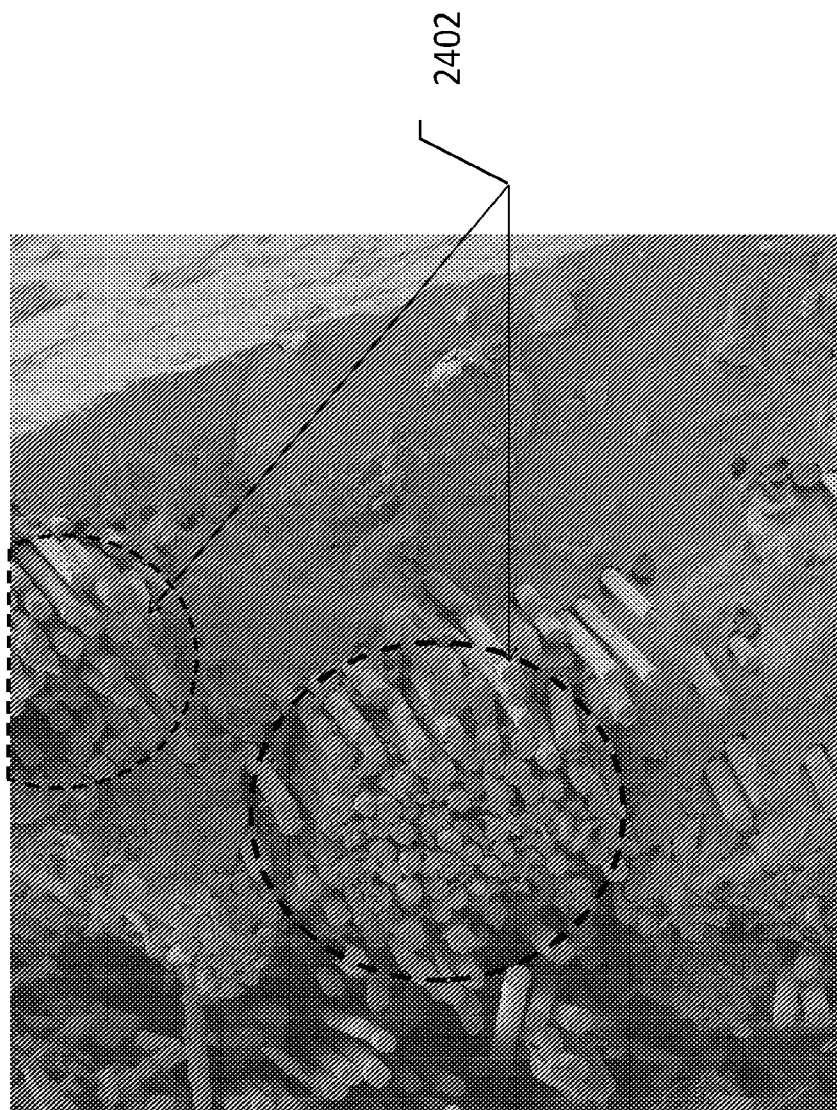
FIG. 24: Scanning Electron Microscope (SEM) image using a secondary electron detector of Au sputtered cross section of a 6 mm pin with 50% fiber content by weight, such as those described in Example 1. Magnification of this image is 500×. This image shows a magnification of the cross section of reinforcing mineral fibers, bundled tightly together in groups 2402 embedded within bioabsorbable polymer matrix.

With regard to circular implants, the reinforcing fibers may optionally take the full circular shape of the implant and curve around the circle shape of the implant without deviation from its circumference. Preferably, a portion or a majority of the reinforcing fibers deviate from the circle shape of the implant such that a tangential angle is formed. The tangential angle is defined as the deviation from the direction of the curve at a fixed starting point, where the fixed starting point is the point where the fiber touches or is closest to coming into contact with the center of the cross-sectional circular area. FIG. 23 depicts the tangential angle of reinforcing fibers to a cannulated circular pin.

Preferably the tangential angle between reinforcing fibers within the circular medical implant and the curvature of the implant is less than 90 degrees, more preferably less than 45 degrees.

Preferably the density of the biocomposite composition for use in herein invention is between 1 to 2 g/mL. More preferentially, density is between 1.2 to 1.9 g/mL. Most preferentially between 1.4 to 1.8 g/mL.

Bioabsorbable Polymers

In a preferred embodiment of the present invention, the biodegradable composite comprises a bioabsorbable polymer.

The medical implant described herein may be made from any biodegradable polymer. The biodegradable polymer may be a homopolymer or a copolymer, including random copolymer, block copolymer, or graft copolymer. The biodegradable polymer may be a linear polymer, a branched polymer, or a dendrimer. The biodegradable polymers may be of natural or synthetic origin. Examples of suitable biodegradable polymers include, but are not limited to polymers such as those made from lactide, glycolide, caprolactone, valerolactone, carbonates (e.g., trimethylene carbonate, tetramethylene carbonate, and the like), dioxanones (e.g., 1,4-dioxanone), 6-valerolactone, 1, dioxepanones) e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate, (polyurethanes, polyanhydrides, polymer drugs (e.g., polydiflunisol, polyaspirin, and protein therapeutics (and copolymers and combinations thereof. Suitable natural biodegradable polymers include those made from collagen, chitin, chitosan, cellulose, poly (amino acids), polysaccharides, hyaluronic acid, gut, copolymers and derivatives and combinations thereof.

According to the present invention, the biodegradable polymer may be a copolymer or terpolymer, for example: polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/ε-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically-3,6-substituted poly-1,4-dioxane-2,5-diones; polyhydroxyalkanoates; such as polyhydroxybutyrates (PH B); PHB/b-hydroxyvalerate copolymers (PHB/PHV); poly-b-hydroxypropionate (PHPA); poly-p-dioxanone (PDS); poly-d-valerolactone-poly-ε-caprolactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanbic acids; polycarbonates; polyorthoesters; polyphosphates; poly(ester anhydrides); and mixtures thereof; and natural polymers, such as sugars; starch, cellulose and cellulose derivatives, polysaccharides, collagen, chitosan, fibrin, hyaluronic acid, polypeptides and proteins. Mixtures of any of the above-mentioned polymers and their various forms may also be used.

Reinforced Bioabsorbable Polymers

According to at least some embodiments of the present invention, the medical implant comprises a reinforced bioabsorbable polymer (i.e. a bioabsorbable composite that includes the previously described polymer and also incorporates a reinforcing filler, generally in fiber form, to increase the mechanical strength of the polymer).

In a more preferred embodiment of the present invention, the reinforced bioabsorbable polymer is a reinforced polymer composition comprised of any of the above-mentioned bioabsorbable polymers and a reinforcing filler, preferably in fiber form. The reinforcing filler may be comprised of organic or inorganic (that is, natural or synthetic) material. Reinforcing filler may be a biodegradable glass, a cellulosic material, a nano-diamond, or any other filler known in the art to increase the mechanical properties of a bioabsorbable polymer. The filler is preferably made from a material or class of material other than the bioabsorbable polymer itself. However, it may also optionally be a fiber of a bioabsorbable polymer itself.

Numerous examples of such reinforced polymer compositions have previously been documented. For example: A biocompatible and resorbable melt derived glass composition where glass fibers can be embedded in a continuous polymer matrix (EP 2 243 749 A1), Biodegradable composite comprising a biodegradable polymer and 20-70 vol % glass fibers (WO2010128039 A1), Resorbable and biocompatible fiber glass that can be embedded in polymer matrix (US 2012/0040002 A1), Biocompatible composite and its use (US 2012/0040015 A1), Absorbable polymer containing poly[succinimide] as a filler (EPO 671 177 B1).

In a more preferred embodiment of the present invention, the reinforcing filler is bound to the bioabsorbable polymer such that the reinforcing effect is maintained for an extended period. Such an approach has been described in US 2012/0040002 A1 and EP 2243500B1, which discusses a composite material comprising biocompatible glass, a biocompatible matrix polymer and a coupling agent capable of forming covalent bonds.

As noted above, the biodegradable composite and fibers are preferably arranged in the form of biodegradable composite layers, where each layer comprises uni-directionally aligned continuous reinforcement fibers embedded in a polymer matrix comprised of one or more bioabsorbable polymers.

The biodegradable composite layers are preferably comprised of one or more biodegradable composite tapes, where each tape comprises uni-directionally aligned continuous reinforcement fibers embedded in a polymer matrix comprised of one or more bioabsorbable polymers.

The biodegradable composite is preferably embodied in a polymer matrix, which may optionally comprise any of the above polymers. Optionally and preferably, it may comprise a polymer selected from the group consisting of PLLA (poly-L-lactide), PDLLA (poly-DL-lactide), PLDLA, PGA (poly-glycolic acid), PLGA (poly-lactide-glycolic acid), PCL (Polycaprolactone), PLLA-PCL and a combination thereof. If PLLA is used, the matrix preferably comprises at least 30% PLLA, more preferably 50%, and most preferably at least 70% PLLA. If PDLA is used, the matrix preferably comprises at least 5% PDLA, more preferably at least 10%, most preferably at least 20% PDLA.

Preferably, the inherent viscosity (IV) of the polymer matrix (independent of the reinforcement fiber) is in the range of 1.2 to 2.4 dl/g, more preferably in the range of 1.5 to 2.1 dl/g, and most preferably in the range of 1.7 to 1.9 dl/g.

Inherent Viscosity (IV) is a viscometric method for measuring molecular size. IV is based on the flow time of a polymer solution through a narrow capillary relative to the flow time of the pure solvent through the capillary.

Reinforcement Fiber

Preferably, reinforcement fiber is comprised of silica-based mineral compound such that reinforcement fiber comprises a bioresorbable glass fiber, which can also be termed a bioglass fiber composite.

Bioresorbable glass fiber may optionally have oxide compositions in the following mol. % ranges:
$Na_2O$: 11.0-19.0 mol. %
$CaO$: 9.0-14.0 mol. %
$MgO$: 1.5-8.0 mol. %
$B_2O_3$: 0.5-3.0 mol. %
$Al_2O_3$: 0-0.8 mol. %
$P_2O_5$: 0.1-0.8 mol. %
$SiO_2$: 67-73 mol. %

And more preferably in the following mol. % ranges:
$Na_2O$: 12.0-13.0 mol. %
$CaO$: 9.0-10.0 mol. %
$MgO$: 7.0-8.0 mol. %
$B_2O_3$: 1.4-2.0 mol. %
$P_2O_5$: 0.5-0.8 mol. %
$SiO_2$: 68-70 mol. %

Additional optional glass fiber compositions have been described previously by Lehtonen T J et al. (*Acta Biomaterialia* 9 (2013) 4868-4877), which is included here by reference in its entirety; such glass fiber compositions may optionally be used in place of or in addition to the above compositions.

Additional optional bioresorbable glass compositions are described in the following patent applications, which are hereby incorporated by reference as if fully set forth herein: Biocompatible composite and its use (WO2010122098); and Resorbable and biocompatible fibre glass compositions and their uses (WO2010122019).

Optional Additional Features

The below features and embodiments may optionally be combined with any of the above features and embodiments.

Tensile strength of the reinforcement fiber is preferably in the range of 1200-2800 MPa, more preferably in the range of 1600-2400 MPa, and most preferably in the range of 1800-2200 MPa.

Elastic modulus of the reinforcement fiber is preferably in the range of 30-100 GPa, more preferably in the range of 50-80 GPa, and most preferably in the range of 60-70 GPa.

Fiber diameter is preferably in the range of 6-20 µm, more preferably in the range of 10-18 µm, and most preferably in the range of 14-16 µm.

Optionally, a majority of reinforcement fibers aligned to the longitudinal axis of the medical implant are of a length of at least 50% of the total length of the implant, preferably at least 60%, more preferably at least 75%, and most preferably at least 85%.

Optionally, fibers may be aligned at an angle to the longitudinal axis (i.e. on a diagonal) such that the length of the fiber may be greater than 100% of the length of the implant. Optionally and preferably, a majority of reinforcement fibers are aligned at an angle that is less than 90°, alternatively less than 60°, or optionally less than 45° from the longitudinal axis.

Preferably, the implant preferably comprises between 2-20 composite tape layers, more preferably between 2-10 layers, and most preferably between 2-6 layers; wherein each layer may be aligned in a different direction or some of the layers may be aligned in the same direction as the other layers.

Preferably, the maximum angle between fibers in at least some of the layers is greater than the angle between the fibers in each layer and the longitudinal axis. For example, one layer of reinforcing fibers may be aligned and a right diagonal to the longitudinal axis while another layer may be aligned at a left diagonal to the longitudinal axis.

Compatibilizer

Optionally and preferably, the composite composition additionally includes a compatibilizer, which for example be such an agent as described in WO2010122098, hereby incorporated by reference as if fully set forth herein.

Biodegradable Composite Alternative Forms

Alternatively, biodegradable composite may comprise composite strands comprising continuous reinforcement fibers or fiber bundles impregnated with bioabsorbable polymer. Preferably, strands are less than 1 cm in diameter. More preferably, strands are less than 8 mm, less than 5 mm, less than 3 mm, or less than 2 mm in diameter.

Alternatively, biodegradable composite may comprise a woven mesh of continuous reinforcement fibers wherein woven mesh is pre-impregnated with bioabsorbable polymer or woven mesh is comprised of reinforcement fibers and subsequently impregnated with bioabsorbable polymer.

Preferably, biodegradable composite mesh layer is less than 1 cm in thickness. More preferably, impregnated mesh is less than 8 mm, less than 5 mm, less than 3 mm, or less than 2 mm in thickness.

Medical Implant Composite Structure

Implant may be selected from a group that includes orthopedic pins, screws, plates, intramedullary rods, hip replacement, knee replacement, meshes, etc.

The average wall thickness in the implant is preferably in the range of 0.2 to 10 mm, more preferably in the range of 0.4 to 5 mm, more preferably of 0.5 to 2 mm, and most preferably in the range of 0.5 to 1.5 mm.

The implant preferably comprises between 2-20 composite tape layers, more preferably between 2-10 layers, and most preferably between 2-6 layers.

Optionally, implant may comprise reinforcing ribs, gussets, or struts.

Rib base thickness is preferably less than 100% of the adjoining wall thickness. More preferably, thickness is less than 85%, and most preferably less than 75%. Rib base thickness is preferably more than 20% of adjoining wall thickness, more preferably more than 30%, and most preferably more than 50% of adjoining wall thickness.

Preferably, rib height is at least 2.0 times the adjoining wall thickness, more preferably at least 3.0 times the wall thickness.

Draft angle of reinforcing ribs is preferably between 0.2-0.8°, more preferably between 0.4-0.6°.

Preferably, distance between ribs is at least 2 times adjoining wall thickness. More preferably, at least 3 times adjoining wall thickness.

Preferably, reinforcing rib or other element increases bending stiffness of implant by at least 20% without increasing compressive or tensile stiffness by more than 10%.

Optionally, ribs along one axis, for example the longitudinal axis of the implant, are taller than the ribs along the perpendicular axis, for example the latitudinal axis of the implant, in order to facilitate easier insertion of the implant.

Optionally, the implant may comprise one or more bosses to accommodate screw insertion. Preferably, the boss is between 2-3 times the screw diameter for self-tapping screw applications. Boss may additionally include supportive gusses or ribs.

Optionally, one or more sides of implant may be textured.

Optionally, implant may contain continuous fibers aligned in a circular arrangement around holes, such as screw or pin holes, within the implant.

Perforated Implant Part Walls

In some medical implants, it is desirable for there to be cellular or tissue ingrowth through the implant so as to strengthen the incorporation of the implant into the tissue and to increase compliance of the implant in physiological function. In order to further promote such ingrowth, it is beneficial to have gaps or holes in the walls of the herein described medical implant.

Preferably, if present, such perforations in implant walls comprise at least 10% of the surface area of the implant, more preferably at least 20%, at least 30%, at least 40%, or at least 50% of the surface area of the implant.

In one optional embodiment of the present invention, the implant is a screw and the fenestrations of the threading contain perforation.

In one embodiment of the present invention, the implant contains perforations between composite tapes or between the reinforcement fibers within composite tapes making up the implant.

In a preferred embodiment, a majority of perforations are between reinforcement fibers and do not penetrate reinforcement fibers.

Cages Full of Bone Filler

In another embodiment of herein invention, the implant comprises an orthopedic implant and the implant forms a partial or full container and an osteoconductive or osteoinductive material is contained within the implant container.

In a preferred embodiment, the implant container is additionally perforated so as to allow improved bone ingrowth into the osteoconductive or osteoinductive material contained within the implant cage.

In an optional embodiment, the implant comprises an opening or door through which bone filler can be introduced and/or bone ingrowth can take place.

In an optional embodiment, the implant comprises two or more discrete parts or separate parts joined by a joint such that implant cage may be filled with bone filler material and subsequently assembled or closed to trap bone filler inside.

Framework of Continuous Fiber Reinforced Structure with Non-Reinforced Surrounding Material Whereas continuous fiber reinforced bioabsorbable composite structures provide the optimal mechanical strength and stiffness to a medical implant, it may also be beneficial in certain cases to have additional features or layers in the medical implant that cannot be made from continuous fiber reinforced composite tapes. In such cases, the mechanical strength of the continuous fiber reinforced bioabsorbable composite structures can be incorporated into the implant but additional sections or layers of non-reinforced polymer may be added to improve or customize the implant. These sections or layers are preferably added to the implant either by overmolding onto the structure or by 3-D printing onto the structure.

In one embodiment of the present invention, medical implant comprises a structural support comprised of a continuous fiber-reinforced bioabsorbable composite material and additionally comprises a section or layer comprised of non-reinforced polymer material.

Optionally the second layer functions as a bone interface layer comprised of a non-reinforced absorbable polymer material. Also optionally the structural support and non-reinforced polymer section are each fabricated using a different production technique. Also optionally the structural support is fabricated by machining, compression molding, or composite flow molding and the interface layer is fabricated by injection molding or 3D printing; optionally the interface layer is fabricated on top of the prefabricated structural support.

Optionally the non-reinforced polymer section is a bone interface layer and dimensions of the interface layer are partially or entirely determined by the bone geometry of a specific patient or patient population.

Optionally the bone geometry of patient or patient population is determined by measuring through imaging technique such as X-Ray, CT, MRI.

Optionally the elastic modulus and/or flexural strength of structural support is at least 20% greater than that of the non-reinforced polymer section.

Optionally, continuous-fiber reinforced composite material in implant is coated with a polymer resin wherein the polymer resin on fiber in the composite material has a higher or lower melting temp than the flowable matrix resin; or polymer resin on fiber has slower or faster degradation rate than flowable matrix resin; or polymer resin on fiber is more hydrophobic or more hydrophilic than flowable matrix resin In an optional embodiment, an additional section or layer is comprised of a reinforced polymer but where polymer is reinforced by non-continuous fibers, preferably fibers less than 10 mm in length, and more preferably less than 5 mm in length.

In an optional embodiment, an additional section or layer of non-reinforced or non-continuous fiber reinforced polymer additional comprises an additive.

Optionally, additive comprises an osteoconductive material or combination of osteoconductive materials such as beta tricalcium phosphate, calcium phosphate, hydroxyapatite, decellularized bone.

Optionally, the additive comprises an anti-microbial agent or bone inducing agent.

Production Method

Continuous-fiber reinforced bioabsorbable implants may optionally be produced using any method known in the art. Preferably, implant is primarily produced by method other than injection molding. More preferably, implant is primarily produced using manufacturing method that subjects implant to compressive pressure, such as compression molding. Preferably, prior to compressive molding, a multi-layer structure is constructed from such composite material by wrapping or other method of adding layers, such that the reinforcement fibers are in tension following such layering.

Preferably, moisture content of implant following compression molding is less than 30%, more preferably less than 20%, even more preferably less than 10%, 8%, 6%, 5%.

Implant Contact with Surrounding Tissue

In an optional embodiment of the present invention, less than 100% of implant surface area is in contact with surrounding tissue. This may be clinically desirable for several reasons:
1. Reduced friction with surrounding tissue upon insertion, easing insertion
2. Reduced bone contact can reduce interference to bone surface blood flow In a preferred embodiment, implant contains surface protrusion elements of at least 0.1 mm in height and less than 2 mm in height that come into contact with tissue surrounding implant.

Preferably, total percentage of surface area of implant that comes into contact with surrounding tissue is less than 80%, more preferably less than 60%, 50%, 40%, 30%.

Balloons

In an optional embodiment of herein invention, implant additionally comprises a balloon. Balloon walls are preferably comprised of between 1-3 layers of reinforced composite.

Fabrication of the Implant

Any of the above-described bioabsorbable polymers or reinforced bioabsorbable polymers may be fabricated into any desired physical form for use with the present invention. The polymeric substrate may be fabricated for example, by compression molding, casting, injection molding, pultrusion, extrusion, filament winding, composite flow molding (CFM), machining, or any other fabrication technique known to those skilled in the art. The polymer may be made into any shape, such as, for example, a plate, screw, nail, fiber, sheet, rod, staple, clip, needle, tube, foam, or any other configuration suitable for a medical device.

Load-Bearing Mechanical Strength

The herein invention particularly relates to bioabsorbable composite materials that can be used in medical applications that require high strength and a stiffness compared to the stiffness of bone. These medical applications require the medical implant to bear all or part of the load applied by or to the body and can therefore be referred to generally as "load-bearing" applications. These include fracture fixation, tendon reattachment, joint replacement, spinal fixation, and spinal cages.

The flexural strength preferred from the herein described load-bearing medical implant is at least 200 MPa, preferably above 400 MPa, more preferably above 600 MPa, and even more preferably above 800 MPa. The Elastic Modulus (or Young's Modulus) of the bioabsorbable composite for use with herein invention is preferably at least 10 GPa, more preferably above 15 GPa, and even more preferably above 20 GPa but not exceeding 100 GPa and preferably not exceeding 60 GPa.

Sustained Mechanical Strength

There is a need for the bioabsorbable load-bearing medical implants of the herein invention to maintain their mechanical properties (high strength and stiffness) for an extended period to allow for sufficient bone healing. The strength and stiffness preferably remains above the strength and stiffness of cortical bone, approximately 150-250 MPa and 15-25 GPa respectively, for a period of at least 3 months, preferably at least 6 months, and even more preferably for at least 9 months in vivo (i.e. in a physiological environment).

More preferably, the flexural strength remains above 400 MPa and even more preferably remains above 600 MPa.

In another embodiment of the present invention, the mechanical strength degradation rate of the coated medical implant approximates the material degradation rate of the implant, as measured by weight loss of the biodegradable composite.

In a preferred embodiment, the implant retains greater than 50% of its mechanical strength after 3 months of implantation while greater than 50% of material degradation and hence weight loss occurs within 12 months of implantation.

In a preferred embodiment, the implant retains greater than 70% of its mechanical strength after 3 months of implantation while greater than 70% of material degradation and hence weight loss occurs within 12 months of implantation.

In a preferred embodiment, the implant retains greater than 50% of its mechanical strength after 6 months of implantation while greater than 50% of material degradation and hence weight loss occurs within 9 months of implantation.

In a preferred embodiment, the implant retains greater than 70% of its mechanical strength after 6 months of implantation while greater than 70% of material degradation and hence weight loss occurs within 9 months of implantation.

The mechanical strength degradation and material degradation (weight loss) rates of the medical implant can be measured after in vivo implantation or after in vitro simulated implantation. In the case of in vitro simulated implantation, the simulation may be performed in real time or according to accelerated degradation standards.

"Biodegradable" as used herein is a generalized term that includes materials, for example polymers, which break down due to degradation with dispersion in vivo. The decrease in mass of the biodegradable material within the body may be the result of a passive process, which is catalyzed by the physicochemical conditions (e.g. humidity, pH value) within the host tissue. In a preferred embodiment of biodegradable, the decrease in mass of the biodegradable material within the body may also be eliminated through natural pathways either because of simple filtration of degradation by-products or after the material's metabolism ("Bioresorption" or "Bioabsorption"). In either case, the decrease in mass may result in a partial or total elimination of the initial foreign material. In a preferred embodiment, said biodegradable composite comprises a biodegradable polymer that undergoes a chain cleavage due to macromolecular degradation in an aqueous environment.

A polymer is "absorbable" within the meaning of this invention if it is capable of breaking down into small, non-toxic segments which can be metabolized or eliminated from the body without harm. Generally, absorbable polymers swell, hydrolyze, and degrade upon exposure to bodily tissue, resulting in a significant weight loss. The hydrolysis reaction may be enzymatically catalyzed in some cases. Complete bioabsorption, i.e. complete weight loss, may take some time, although preferably complete bioabsorption occurs within 24 months, most preferably within 12 months.

The term "polymer degradation" means a decrease in the molecular weight of the respective polymer. With respect to the polymers, which are preferably used within the scope of the present invention said degradation is induced by free water due to the cleavage of ester bonds. The degradation of the polymers as for example used in the biomaterial as described in the examples follows the principle of bulk erosion. Thereby a continuous decrease in molecular weight precedes a highly pronounced mass loss. Said mass loss is attributed to the solubility of the degradation products. Methods for determination of water induced polymer degradation are well known in the art such as titration of the degradation products, viscometry, differential scanning calorimetry (DSC).

The term "Biocomposite" as used herein is a composite material formed by a matrix and a reinforcement of fibers wherein both the matrix and fibers are biocompatible and optionally bioabsorbable. In most cases, the matrix is a polymer resin, and more specifically a synthetic bioabsorbable polymer. The fibers are optionally and preferably of a different class of material (i.e. not a synthetic bioabsorbable polymer), and may optionally comprise mineral, ceramic, cellulosic, or other type of material.

Clinical Applications

The medical implants discussed herein are generally used for bone fracture reduction and fixation to restore anatomical relationships. Such fixation optionally and preferably includes one or more, and more preferably all, of stable fixation, preservation of blood supply to the bone and surrounding soft tissue, and early, active mobilization of the part and patient.

There are several exemplary, illustrative, non-limiting types of bone fixation implants for which the materials and concepts described according to at least some embodiments of the present invention may be relevant, as follows:

Bone Plate

A bone plate is typically used to maintain different parts of a fractured or otherwise severed bone substantially stationary relative to each other during and/or after the healing process in which the bone mends together. Bones of the limbs include a shaft with a head at either end thereof. The shaft of the bone is generally elongated and of relatively cylindrical shape.

It is known to provide a bone plate which attaches to the shaft or head and shaft of a fractured bone to maintain two or more pieces of the bone in a substantially stationary position relative to the one another. Such a bone plate generally comprises a shape having opposing substantially parallel sides and a plurality of bores extending between the opposing sides, wherein the bores are suitable for the receipt of pins or screws to attach the plate to the bone fragments.

For proper function of the bone plate in maintaining different parts of a fractured bone stationary relative to each other, the plate must be of sufficient mechanical strength and stiffness to maintain the position of the bone fragments or pieces. However, it must achieve these mechanical properties within a low profile thickness profile to ensure that there will be sufficient space for the bone plate to fit between bone and the surrounding soft tissue. The thickness of the bone plate is generally in the range of 2.0 mm to 8.0 mm and more commonly in the range of 2.0 mm to 4.0 mm. The widths of the plates are variable but Screws Screws are used for internal bone fixation and there are different designs based on the type of fracture and how the screw will be used. Screws come in different sizes for use with bones of different sizes. Screws can be used alone to hold a fracture, as well as with plates, rods, or nails. After the bone heals, screws may be either left in place or removed.

Screws are threaded, though threading can be either complete or partial. Screws can include compression screws, locking screws, and/or cannulated screws. External screw diameter can be as small as 0.5 or 1.0 mm but is generally less than 3.0 mm for smaller bone fixation. Larger bone cortical screws can be up to 5.0 mm and cancellous screws can even reach 7-8 mm. Some screws are self-tapping and others require drilling prior to insertion of the screw. For cannulated screws, a hollow section in the middle is generally larger than 1 mm diameter in order to accommodate guide wires.

Wires/Pins

Wires are often used to pin bones back together. They are often used to hold together pieces of bone that are too small to be fixed with screws. They can be used in conjunction with other forms of internal fixation, but they can be used alone to treat fractures of small bones, such as those found in the hand or foot. Wires or pins may have sharp points on either one side or both sides for insertion or drilling into the bone.

"K-wire" is a particular type of wire generally made from stainless steel, titanium, or nitinol and of dimensions in the range of 0.5-2.0 mm diameter and 2-25 cm length. "Steinman pins" are general in the range of 2.0-5.0 mm diameter and 2-25 cm length. Nonetheless, the terms pin and wire for bone fixation are used herein interchangeably.

Anchors

Anchors and particularly suture anchors are fixation devices for fixing tendons and ligaments to bone. They are comprised of an anchor mechanism, which is inserted into the bone, and one or more eyelets, holes or loops in the anchor through which the suture passes. This links the anchor to the suture. The anchor which is inserted into the bone may be a screw mechanism or an interference mechanism. Anchors are generally in the range of 1.0-6.5 mm diameter Cable, Ties, Wire Ties Cables, ties, or wire ties can be used to perform fixation by cerclage, or binding, bones together. Such implants may optionally hold together bone that cannot be fixated using penetration screws or wires/pin, either due to bone damage or presence of implant shaft within bone. Generally, diameter of such cable or tie implants is optionally in the range of 1.0 mm-2.0 mm and preferably in the range of 1.25-1.75 mm. Wire tie width may optionally be in the range of 1-10 mm.

Nails or Rods

In some fractures of the long bones, medical best practice to hold the bone pieces together is through insertion of a rod or nail through the hollow center of the bone that normally contains some marrow. Screws at each end of the rod are used to keep the fracture from shortening or rotating, and also hold the rod in place until the fracture has healed. Rods and screws may be left in the bone after healing is complete. Nails or rods for bone fixation are generally 20-50 cm in length and 5-20 mm in diameter (preferably 9-16 mm). A hollow section in the middle of nail or rod is generally larger than 1 mm diameter in order to accommodate guide wires.

Any of the above-described bone fixation implants may optionally be used to fixate various fracture types including but not limited to comminuted fractures, segmental fractures, non-union fractures, fractures with bone loss, proximal and distal fractures, diaphyseal fractures, osteotomy sites, etc.

Example #1—Large Diameter Pins

Below example describes production of large diameter orthopedic pins with reinforced biocomposite materials. This example demonstrates how different medical implant pins comprised of reinforced biocomposite materials can have different performance properties with regard to flexural modulus and strength, both at time zero (following production) and following simulated degradation, relating to the compositional structure, geometry, and composition of each type of pin.

Materials & Methods

Three types of pin implants, each of outer diameter 6 mm and 5 cm length were produced using reinforced composite material. Material composite was comprised of PLDLA 70/30 polymer reinforced with 50% w/w, 70%, or 85% w/w continuous mineral fibers. Mineral fibers composition was approximately $Na_2O$ 14%, $MgO$ 5.4%, $CaO$ 9%, $B_2O_3$ 2.3%, $P_2O_5$ 1.5%, and $SiO_2$ 67.8% w/w. Testing samples were manufactured by compression molding of multiple layers of composite material into a tubular mold, either with or without a 3 mm pin insert in the center. Each layer was comprised of the PLDLA polymer with embedded unidirectionally aligned continuous fibers. Orientation of layers relative to longitudinal axis of implant were 0° (parallel to implant longitudinal axis), 45°, 0°, −45°, 0°, in a repetitive manner according to number of layers in the implant. Each layer was approximately 0.18 mm thick. Three (3) pin samples were produced for each pin group.

Implant samples were tested in a tensile testing system (220Q1125-95, TestResources, MN, USA) for flexural strength, flexural modulus and maximum flexural load according to modified standard test method, ASTM D790 (Standard Test Methods for Flexural Properties of Unreinforced and Reinforced Plastics and Electrical Insulating Materials, http://www.astm.org/Standards/D790.htm, ASTM International, PA, USA). Testing was conducted initially and following simulated in vitro degradation according to modified ASTM F1635 (Standard Test Method for in vitro Degradation Testing of Hydrolytically Degradable Polymer Resins and Fabricated Forms for Surgical Implants, https://www.astm.org/Standards/F1635.htm ASTM International, PA, USA), wherein samples were incubated in simulated body fluid (SBF), 142 $Na^+$, 5 $K^+$, 1.5 $Mg^{2+}$, 2.5 $Ca^{2+}$, 147.8 $Cl^-$, 4.2 $HCO_3^-$, 1 $HPO_4^{3-}$, 0.5 $SO_4^{2-}$ mol/m$^3$, for 5 days at a temperature of 50° C., while shaking at 30 rpm. Mechanical testing was performed using a 5 KN load cell and an appropriate fixture for three point bending testing. Sample span was 40 mm at the beginning of the test and cross head speed was set at 2 mm/min. Dimensions, weight and density of samples were recorded.

Scanning electron microscope (SEM) (FEI Quanta FEG 250, Holland) images were captured for cross-sections of implant samples at several magnifications, with and without Au sputtering, and using either SE or BSE detectors. ImageJ™ (NIH Image Processing Software, http://www.imagej.nih.gov/ii/, National Institute of Health, Maryland, USA) was used to count or measure the following parameters:
1. Distance between fibers
2. Distance between layers
3. Number of fibers per layer
4. Fiber diameter
5. Tangential angle to curvature MATLAB (http://www.mathworks.com/products/matlab/, Mathworks, MA, USA) was used to count or measure the following parameters:
1. Volume distribution of fibers within cross section of implant Results Table 1a shows the mechanical performance results of implant pins made from three different types of reinforced composites as described above. The structural properties of these implants are described by the production methods discussed above and their internal compositions are seen in the associated images. Quantification of several parameters related to the internal composition structure of the implants can be seen in table 1b.

TABLE 1a

Mean values and standard deviations of the mechanical properties and bulk properties of the implants (n = 3).

| Pin Type | E [MPa] | Flexural Strength [MPa] | Max Load [N] | Density [gr/ml] | Volume [mm³] |
|---|---|---|---|---|---|
| Full pin. OD 6 mm. 50% w/w fiber. T = 0 | 8697.0 ± 237.8 | 243.7 ± 14.5 | 549.6 ± 57.3 | 1.60 | 1472.7 |
| Full pin. OD 6 mm. 50% w/w fiber. T = 5 d | 6423.5 ± 243.6 | 118.6 ± 16.6 | 267.9 ± 41.3 | 1.64 | 1480.5 |
| Full pin. OD 6 mm. 70% w/w fiber. T = 0 | 14207.5 ± 811.7 | 224.6 ± 51.6 | 455.1 ± 130.5 | 1.83 | 1365.9 |
| Full pin. OD 6 mm. 70% w/w fiber. T = 5 d | 6745.0 ± 677.6 | 85.1 ± 15.2 | 209.7 ± 48.6 | 1.78 | 1567.7 |
| Hollow pin. OD 6 mm. ID 3 mm. 50% w/w fiber. T = 0 | 7244.6 ± 1736.9 | 148.5 ± 5.4 | 294.0 ± 5.1 | 1.58 | 1067.4 |
| Hollow pin. OD 6 mm. ID 3 mm. 50% w/w fiber. T = 5 d | 4281.6 ± 1608.2 | 81.2 ± 12.5 | 169.6 ± 27.4 | 1.63 | 1113.1 |

Figure 28:
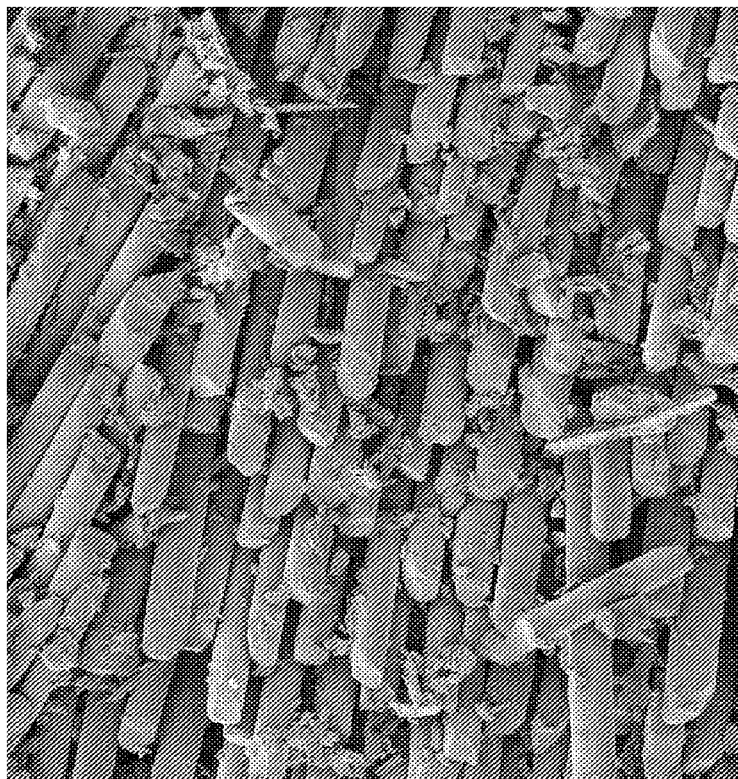
FIG. 28: Scanning Electron Microscope (SEM) image using a secondary electron detector of Au sputtered cross section of a 6 mm pin with 85% fiber content by weight, such as those described in Example 1. Magnification 1000×. This image shows a magnification of the cross section of reinforcing mineral fibers, with little or no bioabsorbable polymer matrix surrounding the said fibers.

Full pin samples produced with GD 6 mm, 85% w/w fiber severely lacked in cohesive strength, likely due to insufficient amount of polymer binding between fiber layers. These samples failed during loading onto the tensile testing system and therefore mechanical property results were not recorded. Images of these pins can be seen in FIGS. 27 and 28, which show high amount of fibers and absence of polymer.

As can be seen in Table IA, incubation for 5 days in SBF at 50° C., which accelerates degradation rate, resulted in a decrease in modulus of 26%, 53% and 41% in the full 50% w/w, full 70% w/w and hollow 6 mm pins respectively. Incubation for 5 days in SBF at 50° C., which accelerates degradation rate, resulted in a decrease in flexural strength of 51%, 62% and 45% in the full 50% w/w, full 70% w/w and hollow 6 mm pins respectively. Incubation for 5 days in SBF at 50° C., which accelerates degradation rate, resulted in a decrease in maximum flexural load of 51%, 53% and 42% in the full 50% w/w, full 70% w/w and hollow 6 mm pins respectively.

TABLE 1b

Measured structural parameters relating the reinforcing fibers and biocomposite layers within two types of biocomposite pins.

Figure 1:
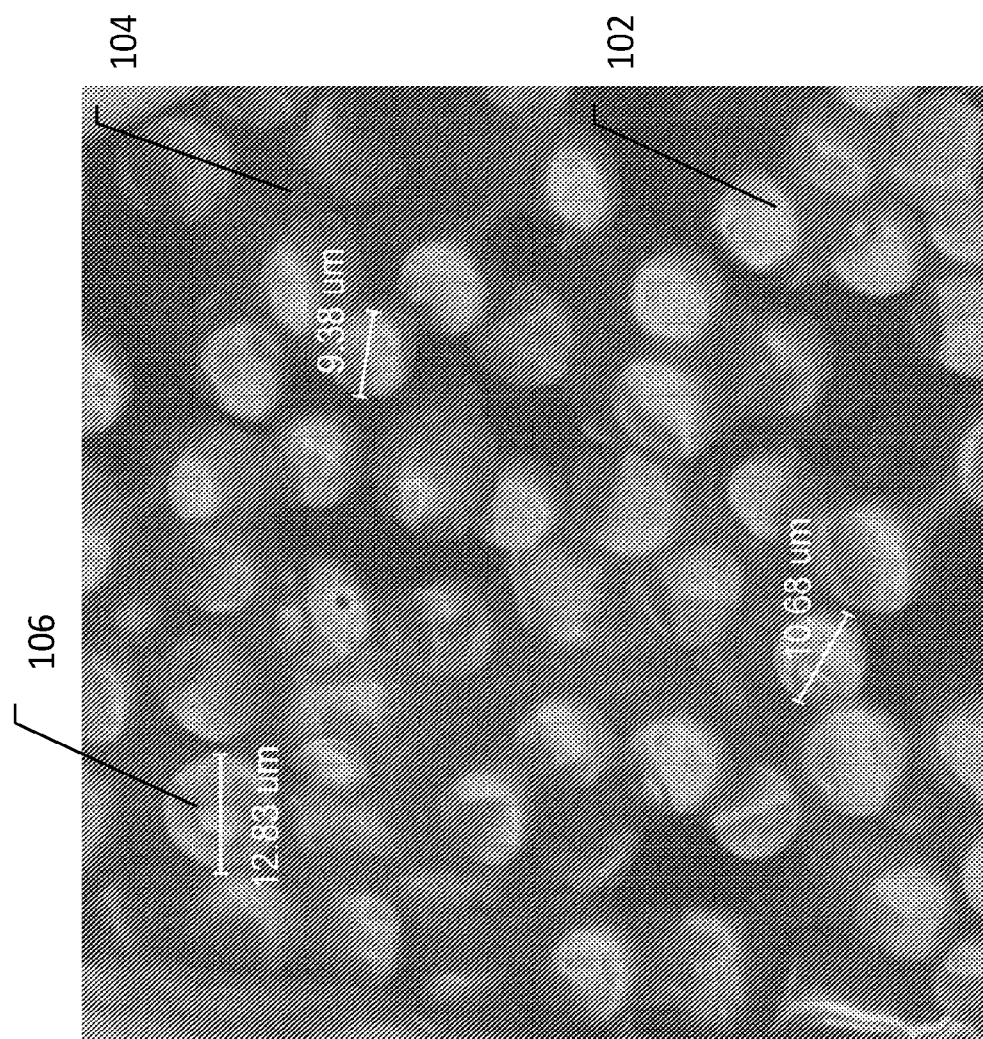
FIG. 1: Scanning Electron Microscope (SEM) image using a Back-Scattered Electrons (BSE) detector of a cross section of a 6 mm pin with 50% fiber content by weight, such as those described in Example 1. Magnification of this image is 2,500×. This image shows a magnification of the cross section of reinforcing mineral fibers 102 embedded within bioabsorbable polymer matrix 104. The fiber diameter is indicated within the image 106.
Figure 2:
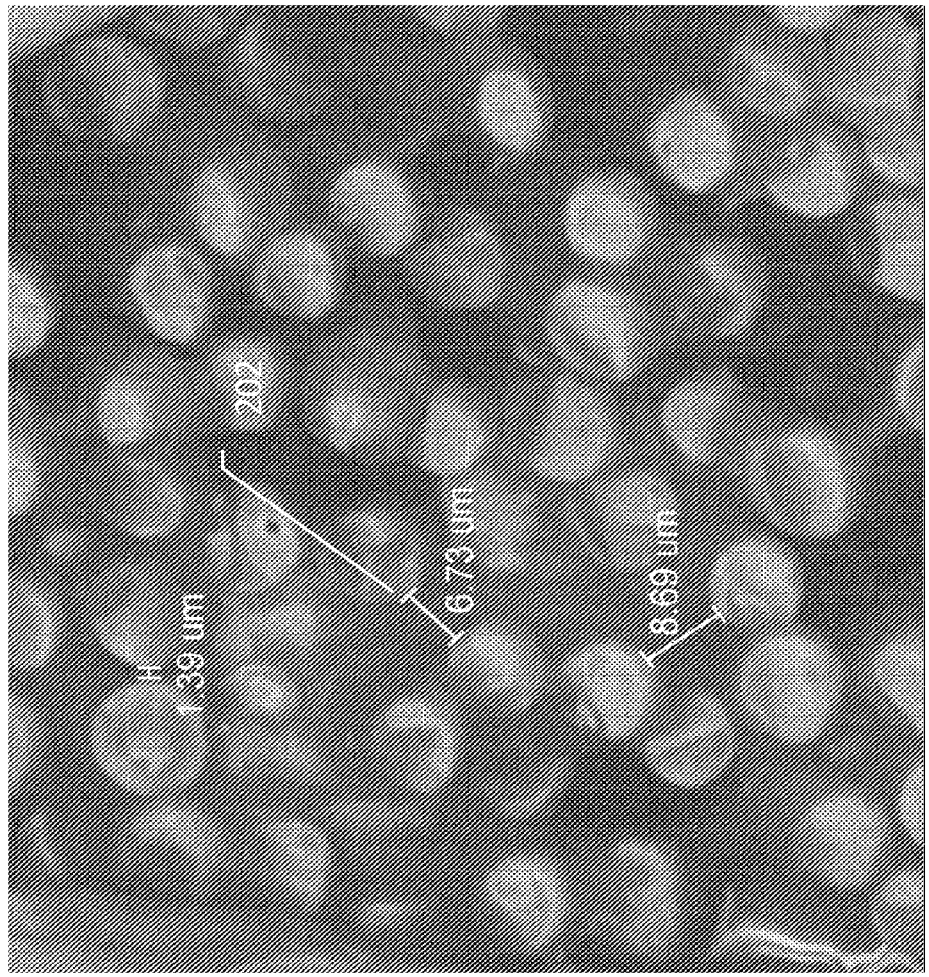
FIG. 2: Scanning Electron Microscope (SEM) image using a Back-Scattered Electrons (BSE) detector of a cross section of a 6 mm pin with 50% fiber content by weight, such as those described in Example 1. Magnification of this image is 2,500×. This image shows a magnification of the cross section of reinforcing mineral fibers embedded within bioabsorbable polymer matrix. The distance between adjacent fibers is indicated by 202.
Figure 3:
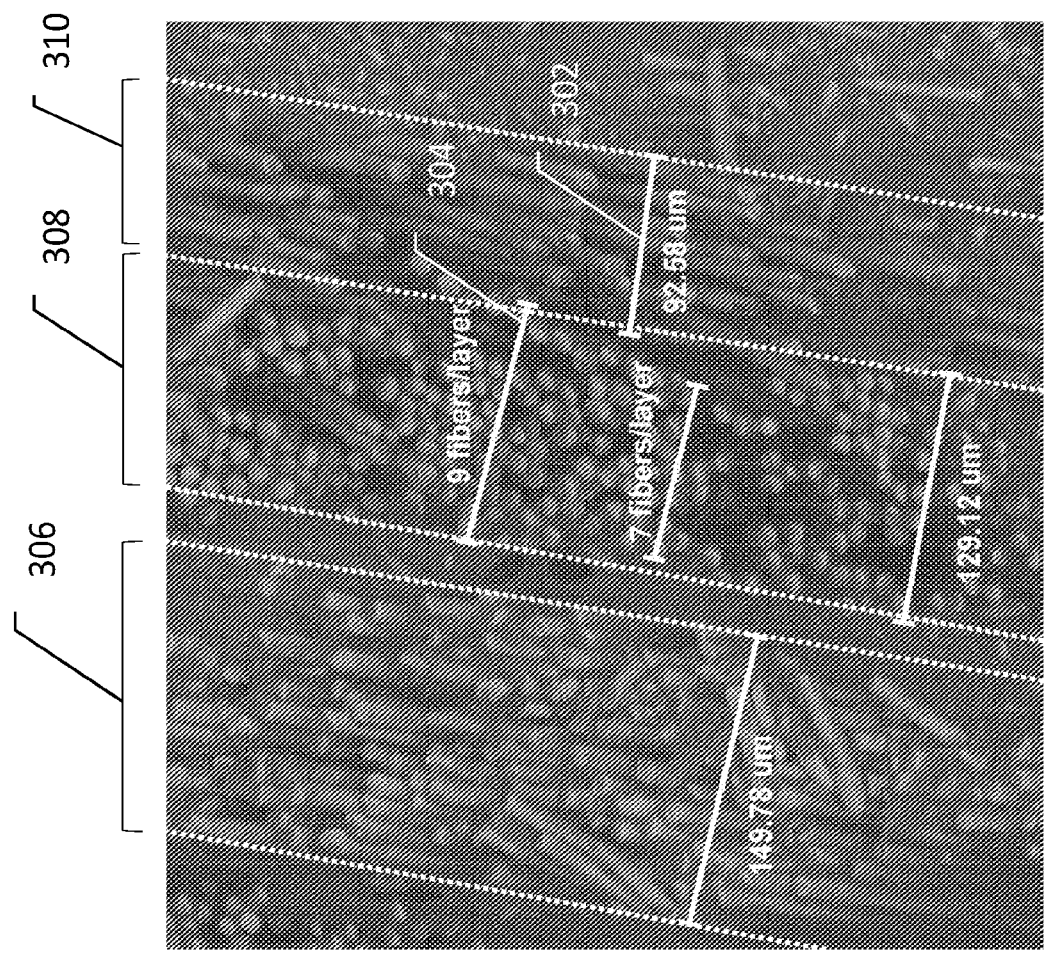
FIG. 3: Scanning Electron Microscope (SEM) image using a Back-Scattered Electrons (BSE) detector of a cross section of a 6 mm pin with 50% fiber content by weight, such as those described in Example 1. Magnification of this image is 500×. This image shows a magnification of the cross section of reinforcing mineral fibers embedded within bioabsorbable polymer matrix. Each layer 306 308 310 is comprised of reinforcement fibers 304 and is of a certain thickness 302.
Figure 4:
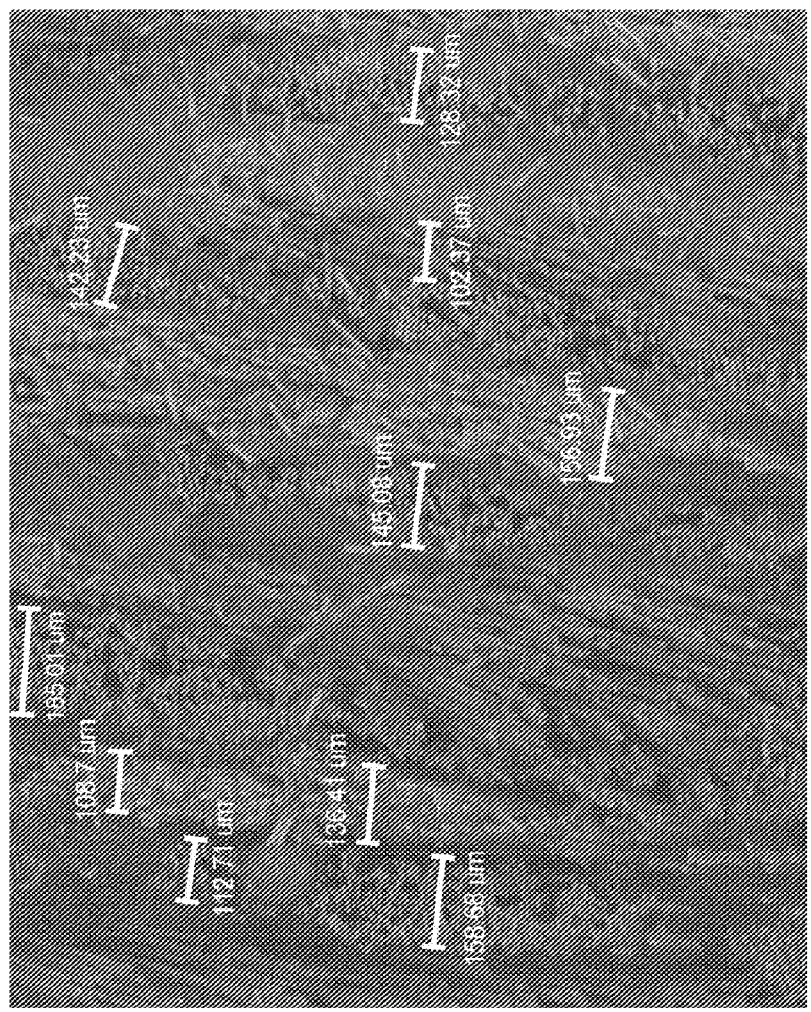
FIG. 4: Scanning Electron Microscope (SEM) image using a Back-Scattered Electrons (BSE) detector of a cross section of a 6 mm pin with 50% fiber content by weight, such as those described in Example 1. Magnification of this image is 150×. This image shows a magnification of the cross section of reinforcing mineral fibers embedded within bioabsorbable polymer matrix.
Figure 5:
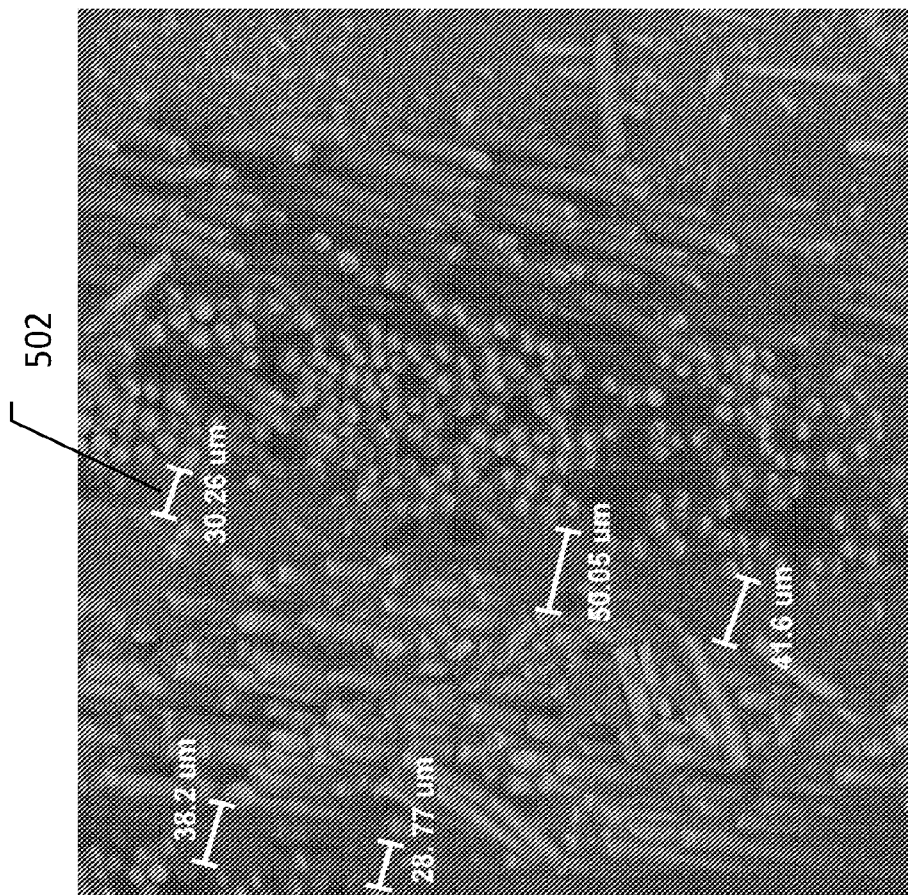
FIG. 5: Scanning Electron Microscope (SEM) image using a Back-Scattered Electrons (BSE) detector of a cross section of a 6 mm pin with 50% fiber content by weight, such as those described in Example 1. Magnification of this image is 500×. This image shows a magnification of the cross section of reinforcing mineral fibers embedded within bioabsorbable polymer matrix. Each layer is separated by an area of bioabsorbable polymer matrix 502.
Figure 6:
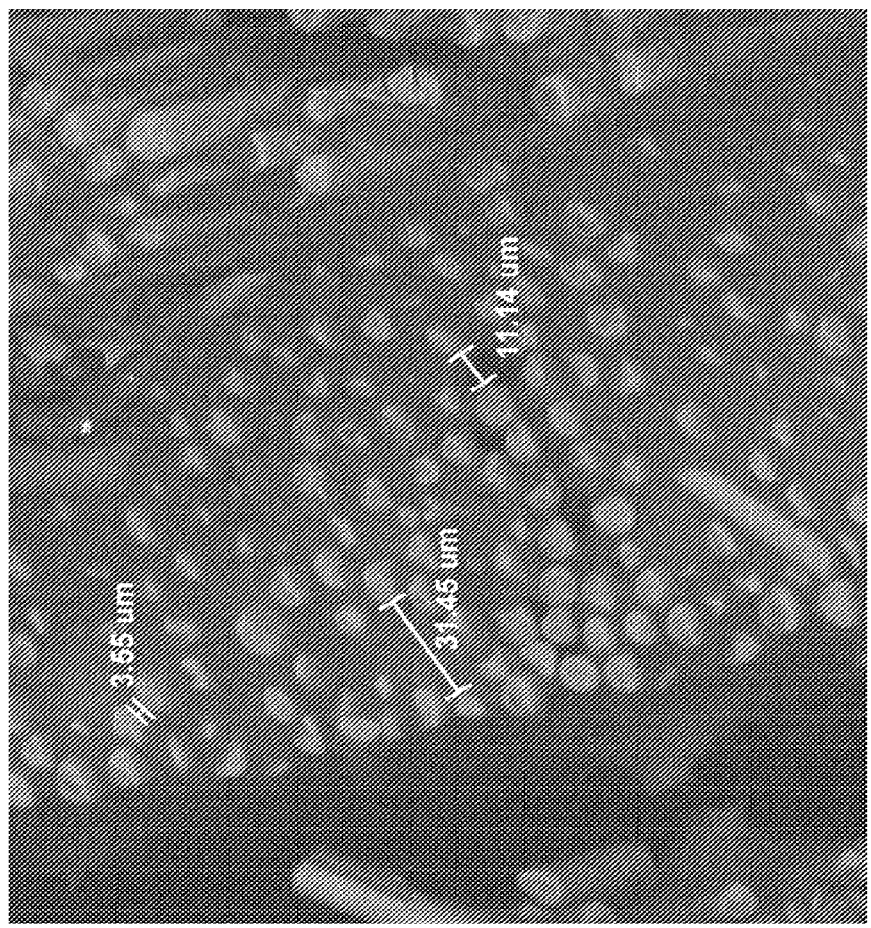
FIG. 6: Scanning Electron Microscope (SEM) image using a Back-Scattered Electrons (BSE) detector of a cross section of a 6 mm pin with 70% fiber content by weight, such as those described in Example 1. Magnification of this image is 500×. This image shows a magnification of the cross section of reinforcing mineral fibers embedded within bioabsorbable polymer matrix. The distance between adjacent fibers is indicated.

| | Fiber diameter range (μm) | Distance between fibers (μm) | Fibers in layer thickness | Layer thickness (μm) | Distance between layers (μm) |
|---|---|---|---|---|---|
| Full pin. OD 6 mm. 50% w/w fiber | 9.38-12.83 (FIG. 1) | 1.39-8.7 (FIG. 2) | 7-9 (FIG. 3) | 92.6-185.0 (FIG. 3, 4) | 28.77-50.05 (FIG. 5) |
| Full pin. OD 6 mm. 70% w/w fiber | | 4.63-31.45 (FIG.6) | 9-13 (FIG.7) | 161.52 (FIG. 7) | |

Without wishing to be limited by a single hypothesis, it is believed that reinforcing fiber content, diameter, distribution, and arrangement into layers seen in this example (Example 1) were the cause or at least a significantly contributing factor.

Specifically with regard to reinforcing fiber, increasing reinforcing fiber content may contribute positively to mechanical properties of a medical implant, as seen by the stronger and stiffer samples produced with 70% fiber as compared with those produced with 50% fiber. However, the 70% fiber implants seemed to lose mechanical properties at a faster rate. Thus, there are potential benefits to each of these amount of fibers. Above a certain point, overly high fiber content can result in failure of the implant, as observed with the 85% fiber pins.

Example #2—Small Diameter Pins

Below example describes production of small diameter orthopedic pins with reinforced biocomposite materials. This example demonstrates how different medical implant pins comprised of reinforced biocomposite materials can have different performance properties with regard to flexural modulus and strength, both at time zero (following production) and following simulated degradation (for example upon insertion to the body), relating to the compositional structure, geometry, and composition of each type of pin.

Materials & Methods

Three types of pin implants, each of outer diameter 2 mm and 5 cm length were produced using reinforced composite material. Material composite was comprised of PLDLA 70/30 polymer reinforced with 50% w/w or 70% w/w continuous mineral fibers. Mineral fiber composition was approximately $Na_2O$ 14%, $MgO$ 5.4%, $CaO$ 9%, $B_2O_3$ 2.3%, $P_2O_5$ 1.5%, and $SiO_2$ 67.8% w/w. Testing samples were manufactured by compression molding of multiple layers of composite material into a tubular mold, either with or without a 1 mm pin insert in the center. Each layer was comprised of the PLDLA polymer with embedded unidirectionally aligned continuous fibers. Orientation of layers relative to longitudinal axis of implant were 0° (parallel to implant longitudinal axis), 45°, 0°, −45°, 0°, in a repetitive manner according to number of layers in the implant. Each layer was approximately 0.18 mm thick. Three (3) pin samples were produced for each pin group.

Implant samples were tested in a tensile testing system (220Q1125-95, TestResources, MN, USA) for flexural strength, flexural modulus and maximum flexural load according to modified standard test method, ASTM D790 (Standard Test Methods for Flexural Properties of Unreinforced and Reinforced Plastics and Electrical Insulating Materials, http://www.astm.org/Standards/D790.htm, ASTM International, PA, USA). Testing was conducted initially and following simulated in vitro degradation according to modified ASTM F1635, (Standard Test Method for in vitro Degradation Testing of Hydrolytically Degradable Polymer Resins and Fabricated Forms for Surgical Implants, http://www.astm.org/Standards/D1635.htm ASTM International, PA, USA) wherein samples were incubated in simulated body fluid (SBF), 142 $Na^+$, 5 $K^+$, 1.5 $Mg^{2+}$, 2.5 $Ca^{2+}$, 147.8 $Cl^-$, 4.2 $HCO_3^-$, 1 $HPO_4^{3-}$, 0.5 $SO_4^{2-}$ mol/$m^3$, for 5 days at a temperature of 50° C., while shaking at 30 rpm. Mechanical testing was performed using a 500 N load cell and an appropriate fixture for three point bending testing. Sample span was 40 mm at the beginning of the test and cross head speed was set at 2 mm/min. Dimensions, weight and density of samples were recorded.

Scanning electron microscope (SEM) (FEI Quanta FEG 250, Holland) images were captured for cross-sections of implant samples at several magnifications, with and without Au sputtering, and using either SE or BSE detectors. ImageJ™ (NIH Image Processing Software, http://www.imagej.nih.gov/ii/, National Institute of Health, Maryland, USA) was used to count or measure the following parameters:
1. Distance between fibers
2. Distance between layers
3. Number of fibers per layer
4. Fiber diameter
5. Tangential angle to curvature MATLAB (http://www.mathworks.com/products/matlab, Mathworks, MA, USA) was used to count or measure the following parameters:
1. Volume distribution of fibers within cross section of implant: The percentage of fiber to polymer was calculated by summing the entire fiber area in the image divided by the area of the entire implant cross section in the image.

Percentage of Fiber to Polymer=Sum of Fiber AreaArea of Entire Cross Section*100

Results

Table 2a shows the mechanical performance results of three different types of reinforced composites implant pins produced as described above. The structural properties of these implants are described by the production methods discussed above and their internal compositions are seen in the associated images. Quantification of several parameters related to the internal composition structure of the implants can be seen in tables 2b, c and d.

TABLE 2a

Mean values and standard deviations of the mechanical properties and bulk properties of the implants (n = 3).

| Pin Type | E [MPa] | Flexural Strength [MPa] | Max Load [N] | Density [gr/ml] | Volume [mm³] |
|---|---|---|---|---|---|
| Full pin. OD 2 mm. 50% w/w fiber. T = 0 | 273.6 ± 48.3 | 11761.0 ± 1028.8 | 25.7 ± 3.79 | 1.43 | 180.7 |
| Full pin. OD 2 mm. 50% w/w fiber. T = 5 d | 127.2 ± 23.4 | 11954.9 ± 2885.5 | 12.45 ± 2.4 | 1.37 | 185.88 |
| Full pin. OD 2 mm. 70% w/w fiber. T = 0 | 290.6 ± 2.7 | 14062.2 ± 2158.3 | 30.16 ± 1.6 | 1.55 | 192.43 |
| Full pin. OD 2 mm. 70% w/w fiber. T = 5 d | 78.9 ± 14.4 | 9931.5 ± 358.8 | 8.65 ± 1.2 | 1.57 | 201.7 |
| Hollow pin. OD 2 mm. ID 1 mm. 50% w/w fiber. T = 0 | 136.6 ± 11.7 | 10231.3 ± 1609.2 | 14.1 ± 1.1 | 1.37 | 157.6 |
| Hollow pin. OD 2 mm. ID 1 mm. 50% w/w fiber. T = 5 d | 100.1 ± 16.5 | 6913.7 ± 2420.1 | 10.35 ± 2.11 | 1.56 | 158.1 |

Incubation for 5 days in SBF at 50° C., which accelerates degradation rate, resulted in a decrease in flexural strength of 54%, 27% and 73% in the full 50% w/w, full 70% w/w and hollow 2 mm pins respectively. Incubation for 5 days in SBF at 50 UC, which accelerates degradation rate, resulted in a decrease in maximum flexural load of 52%, 27% and 71% in the full 50% w/w, full 70% w/w and hollow 2 mm pins respectively. Incubation for 5 days in SBF at 50° C., which accelerates degradation rate, resulted in a decrease in flexural modulus of 32% and 29% in the full 70% w/w and hollow 2 mm 50% w/w pins respectively.

TABLE 2b

Measured structural parameters relating the reinforcing fibers and biocomposite layers within a biocomposite pin

Figure 8:
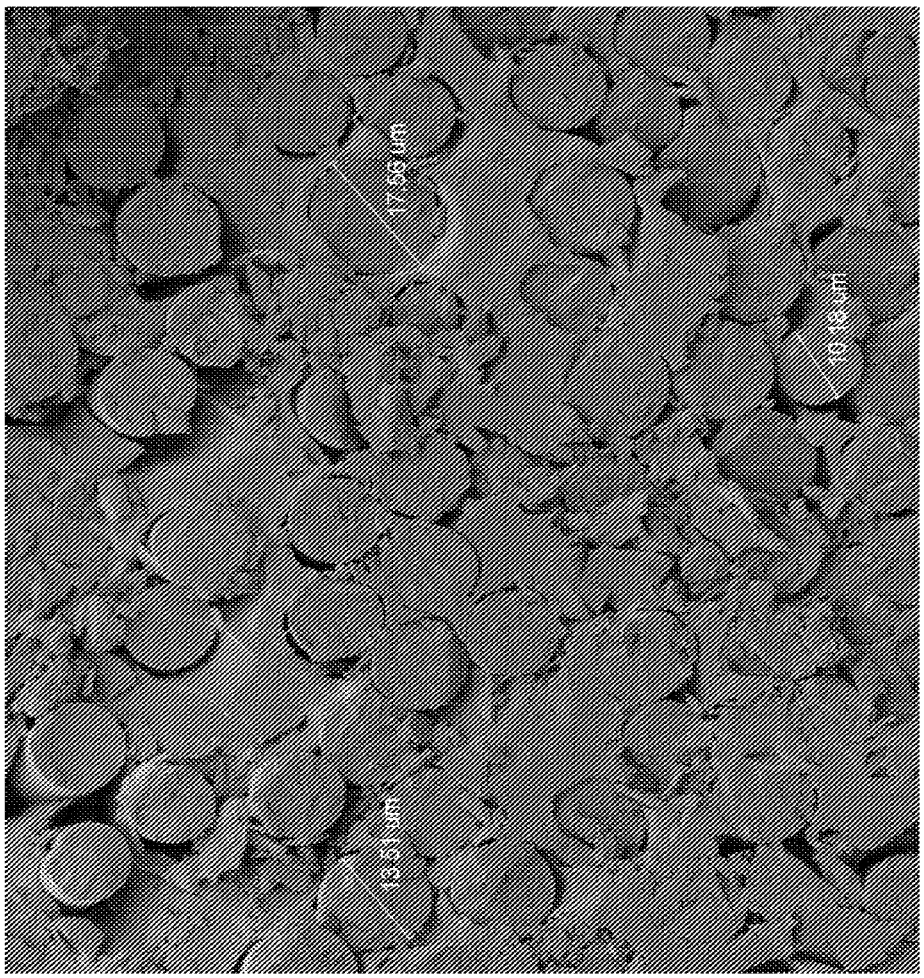
FIG. 8: Scanning Electron Microscope (SEM) image using a secondary electron detector of Au sputtered cross section of a 2 mm pin with 50% fiber content by weight, such as those described in Example 2. Magnification of this image is 2,000×. This image shows a magnification of the cross section of reinforcing mineral fibers embedded within bioabsorbable polymer matrix. The fiber diameter is indicated within the image.
Figure 9:
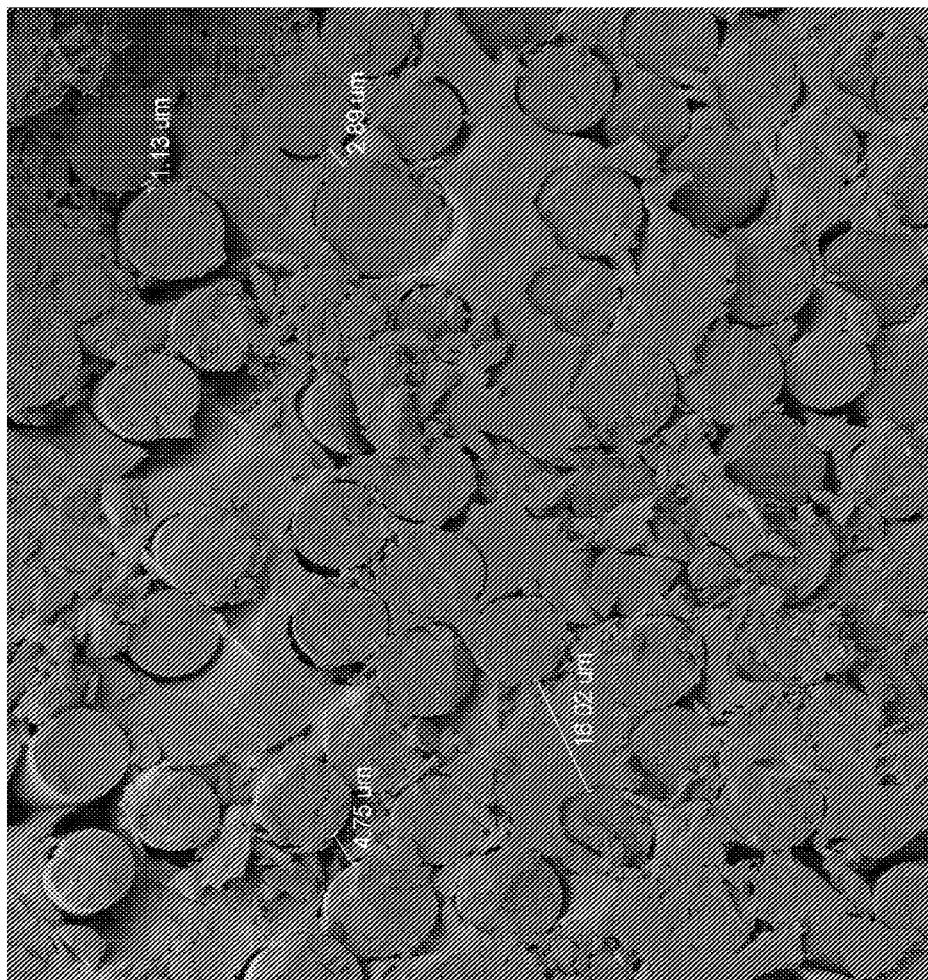
FIG. 9: Scanning Electron Microscope (SEM) image using a secondary electron detector of Au sputtered cross section of a 2 mm pin with 50% fiber content by weight, such as those described in Example 2. Magnification of this image is 2,000×. This image shows a magnification of the cross section of reinforcing mineral fibers embedded within bioabsorbable polymer matrix. The distance between adjacent fibers is indicated.
Figure 12:
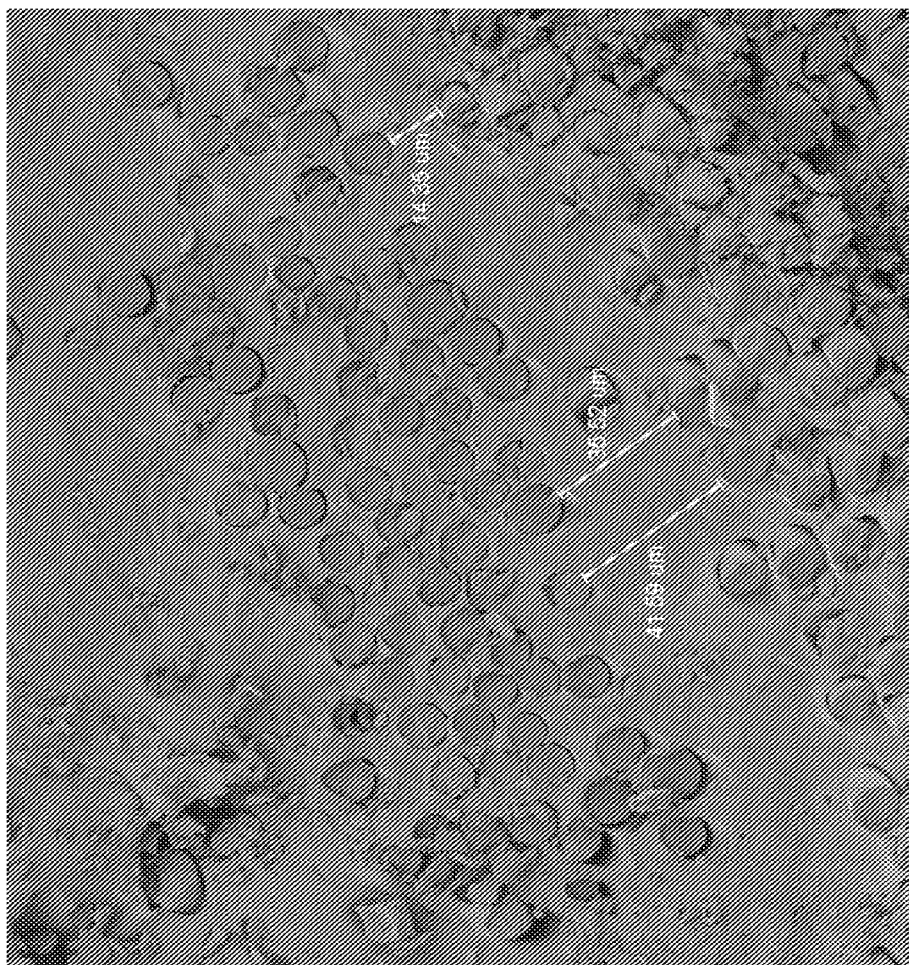
FIG. 12: Scanning Electron Microscope (SEM) image using a secondary electron detector of Au Sputtered cross section of a 2 mm pin with 50% fiber content by weight, such as those described in Example 2. Magnification of this image is 1,000×. This image shows a magnification of the cross section of reinforcing mineral fibers embedded within bioabsorbable polymer matrix. Each layer is separated by an area of bioabsorbable polymer matrix.
Figure 13:
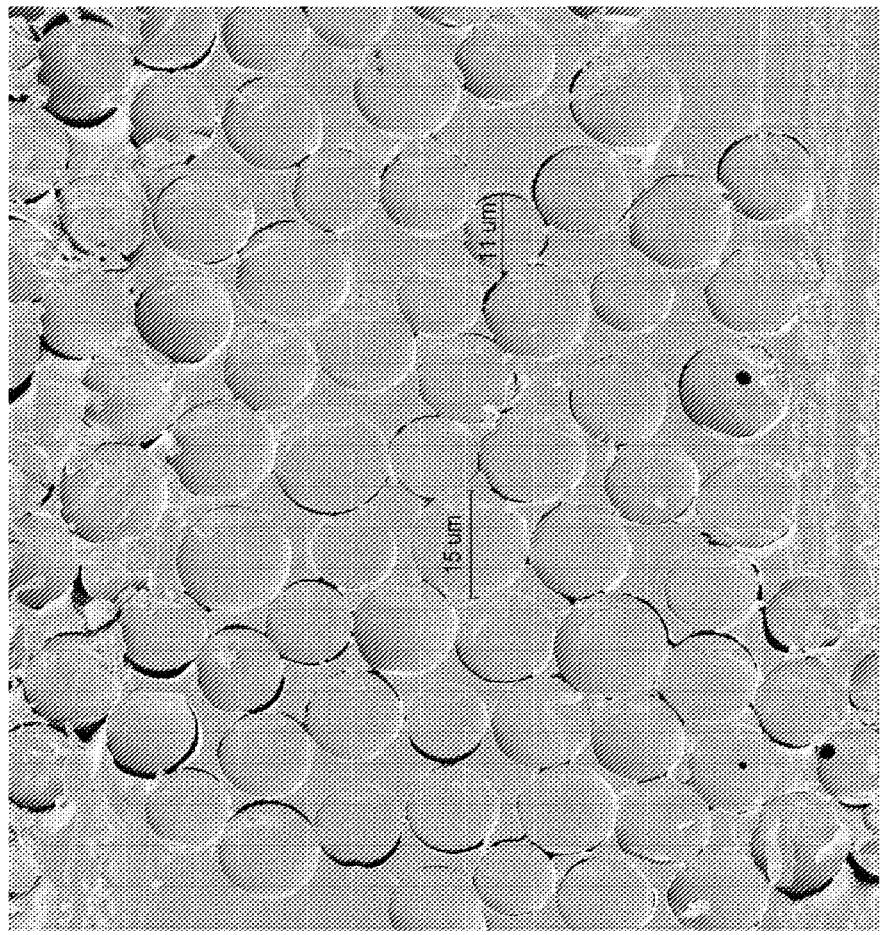
FIG. 13: Scanning Electron Microscope (SEM) image using a secondary electron detector of Au Sputtered cross section of a 2 mm cannulated pin with 50% fiber content by weight, such as those described in Example 2. Magnification of this image is 1,000×. This image shows a magnification of the cross section of reinforcing mineral fibers embedded within bioabsorbable polymer matrix. The fiber diameter is indicated within the image.
Figure 14:
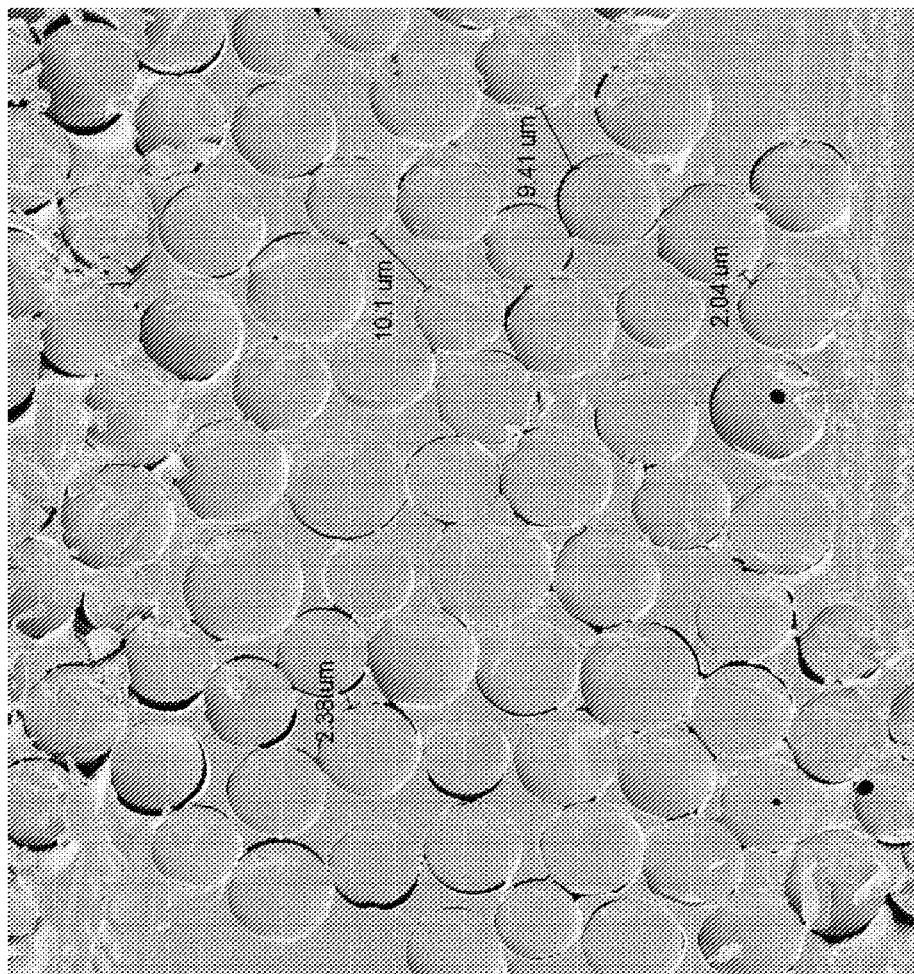
FIG. 14: Scanning Electron Microscope (SEM) image using a secondary electron detector of Au Sputtered cross section of a 2 mm cannulated pin with 50% fiber content by weight, such as those described in Example 2. Magnification of this image is 1,000×. This image shows a magnification of the cross section of reinforcing mineral fibers embedded within bioabsorbable polymer matrix. The distance between adjacent fibers is indicated.
Figure 16:
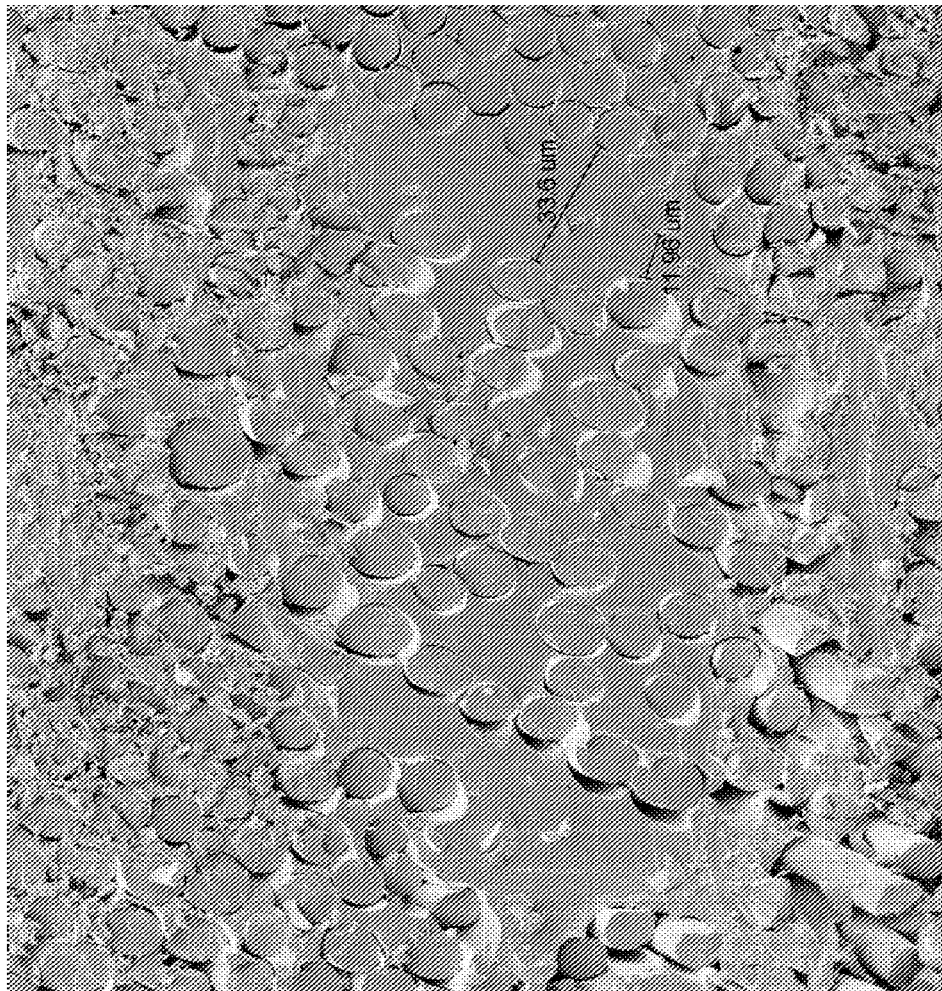
FIG. 16: Scanning Electron Microscope (SEM) image using a secondary electron detector of Au Sputtered cross section of a 2 mm cannulated pin with 50% fiber content by weight, such as those described in Example 2. Magnification of this image is 1,000×. This image shows a magnification of the cross section of reinforcing mineral fibers embedded within bioabsorbable polymer matrix. Each layer is separated by an area of bioabsorbable polymer matrix.

| | Fiber diameter range (μm) | Distance between fibers (μm) | Fibers in layer thickness | Layer thickness (μm) | Distance between layers (μm) |
|---|---|---|---|---|---|
| Full pin. OD 2 mm. 50% w/w fiber | 10.18-13.5 (FIG. 8) | 2.80-16.02 (FIG. 9) | 4-6 (FIG. 10) | 91.09 (FIG. 10) | 14.35-41.59 (FIG. 12) |
| Hollow pin. OD 2 mm, ID 1 mm. 50% w/w fiber | 11-15 (FIG. 13) | 2.04-10.11 (FIG. 14) | | | 11.96-33.6 (FIG. 16) |

TABLE 2c

Figure 11:
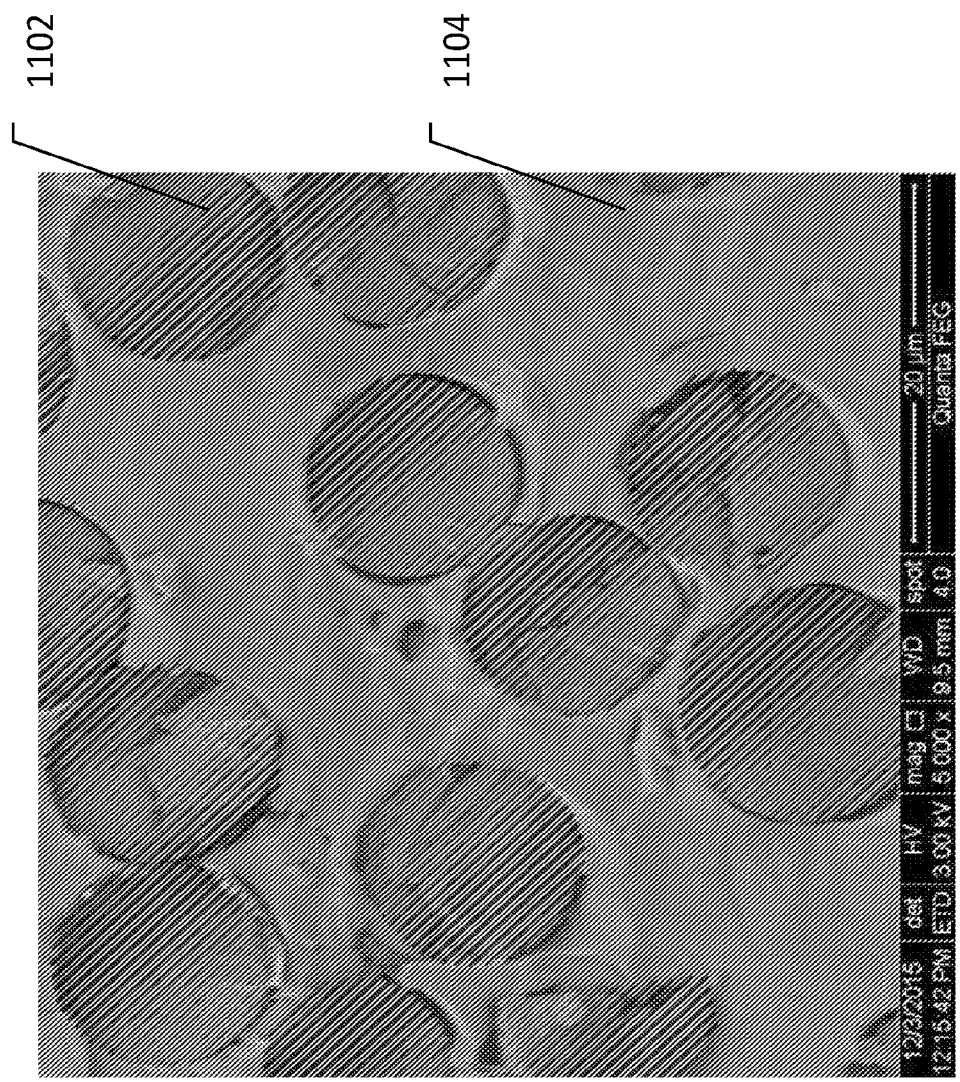
FIG. 11: Scanning Electron Microscope (SEM) image using a secondary electron detector of Au sputtered cross section of a 2 mm pin with 50% fiber content by weight, such as those described in Example 2. Magnification of this image is 5,000×. This image shows a magnification of the cross section of reinforcing mineral fibers 1102 embedded within bioabsorbable polymer matrix 1104.

Measured volume percentage of fiber as measured from cross-section of biocomposite full pin implant of OD 2 mm, 50% w/w fiber (see FIG. 11)

| Area of Entire Cross Section | Sum of Fiber Area | Remaining Area | Percentage of Fiber to Polymer |
|---|---|---|---|
| 22579 μm | 11043 μm | 1.1536e+04 μm | 48.90% |

TABLE 2d

Figure 15:
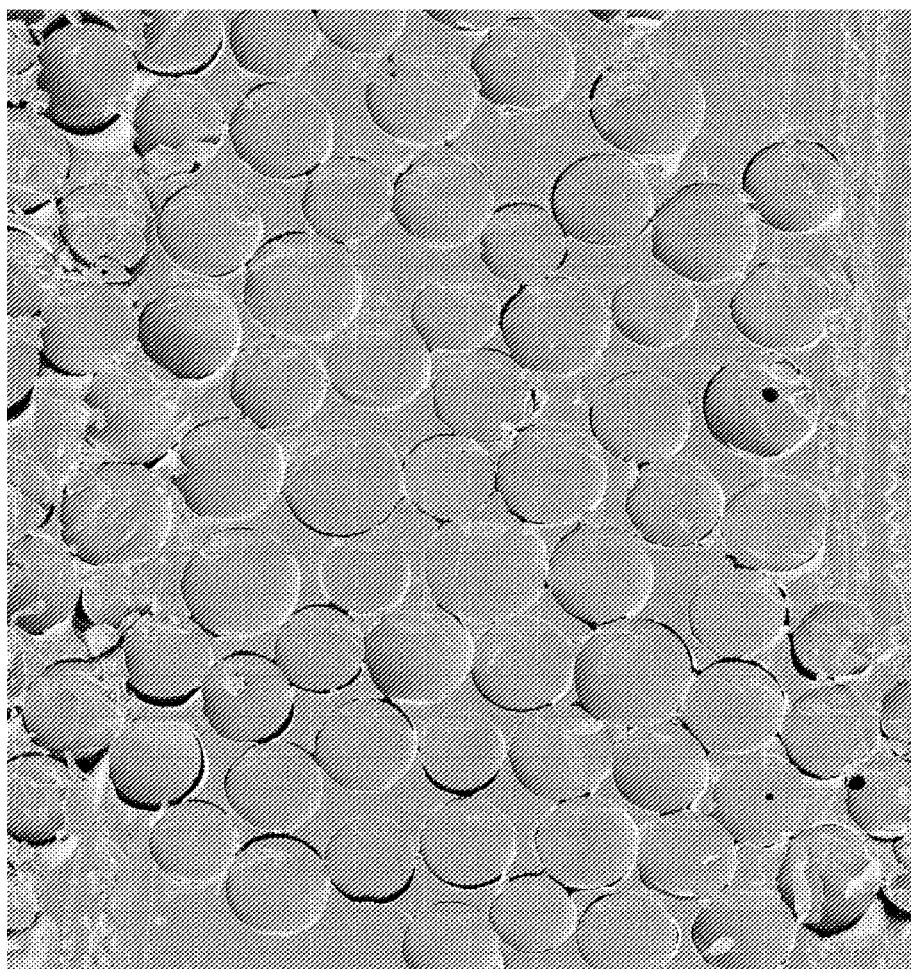
FIG. 15: Scanning Electron Microscope (SEM) image using a secondary electron detector of Au sputtered cross section of a 2 mm cannulated pin with 50% fiber content by weight, such as those described in Example 2. Magnification of this image is 1,000×. This image shows a magnification of the cross section of reinforcing mineral fibers embedded within bioabsorbable polymer matrix.

Measured volume percentage of fiber as measured from cross-section of biocomposite full plate implant of OD 2 mm, ID 1 mm, 50% w/w fiber (see FIG. 15)

| Area of Entire Cross Section | Sum of Fiber Area | Remaining Area | Percentage of Fiber to Polymer |
|---|---|---|---|
| 14094 μm | 9645.14 μm | 4448.86 μm | 68.43% |

Without wishing to be limited by a single hypothesis, it is believed that reinforcing fiber content, diameter, distribution, and arrangement into layers seen in this example (Example 2) were the cause or at least a significantly contributing factor.

This example also suggests a potential structural difference between different implant part geometries (between a full pin and cannulated pin), where it is optionally possible for reinforcing fiber layers in the biocomposite implant to arrange and align themselves in differential manners depending on the shape of the implant and the forces that the implant is exposed to during its production.

Example #3—Plates

Below example describes production of thin orthopedic plates with reinforced biocomposite materials. This example demonstrates how different medical implant plates comprised of reinforced biocomposite materials can have different performance properties with regard to flexural modulus and strength, both at time zero (following production) and following simulated degradation, relating to the compositional structure, geometry, and composition of each type of plate.

Materials & Methods

Four types of plate implants, each with a thickness of 2 mm, width of 12.8 mm and 6 cm length were produced using reinforced composite material. Material composite was comprised of PLDLA 70/30 polymer reinforced with 50% w/w or 70% w/w continuous mineral fibers. Mineral fibers composition was approximately $Na_2O$ 14%, MgO 5.4%, CaO 9%, $B_2O_3$ 2.3%, $P_2O_5$ 1.5%, and $SiO_2$ 67.8% w/w. Testing samples were manufactured by compression molding of multiple layers of composite material into a rectangle mold. Each layer was comprised of the PLDLA polymer with embedded uni-directionally aligned continuous fibers. Orientation of layers relative to longitudinal axis of implant were 0° (parallel to implant longitudinal axis), 45°, 0°, −45°, 0°, in a repetitive manner according to number of layers in the implant. Each layer was approximately 0.18 mm thick. For the amorphous plates, continuous fibers were cut to small pieces, mixed and molded. Three (3) plate samples were produced for each plate group.

Implant samples were tested in a tensile testing system (220Q1125-95, TestResources, MN, USA) for flexural strength, flexural modulus and maximum flexural load according to modified standard test method, ASTM D790 (Standard Test Methods for Flexural Properties of Unreinforced and Reinforced Plastics and Electrical Insulating Materials, http://www.astm.org/Standards/D790.htm, ASTM International, PA, USA). Testing was conducted initially and following simulated in vitro degradation according to modified ASTM F1635, (Standard Test Method for in vitro Degradation Testing of Hydrolytically Degradable Polymer Resins and Fabricated Forms for Surgical Implants, http://www.astm.org/Standards/D1635.htm ASTM International, PA, USA) wherein samples were incubated in simulated body fluid (SBF), 142 $Na^+$, 5 $K^+$, 1.5 $Mg^{2+}$, 2.5 $Ca^{2+}$, 147.8 $Cl^-$, 4.2 $HCO_3^-$, 1 $HPO_4^{3-}$, 0.5 $SO_4^{2-}$ mol/m$^3$, for 5 days at a temperature of 50° C., while shaking at 30 rpm. Mechanical testing was performed using a 5 KN load cell and an appropriate fixture for three point bending testing. Sample span was 40 mm at the beginning of the test and cross head speed was set at 2 mm/min. Dimensions, weight and density of samples were recorded.

Scanning electron microscope (SEM) (FEI Quanta FEG 250, Holland) images were captured for cross-sections of implant samples at several magnifications, with and without Au sputtering, and using either SE or BSE detectors. Image™ (NIH Image Processing Software, http://www.imagej.nih.gov/ij, National Institute of Health, Maryland, USA) was used to count or measure the following parameters:
1. Distance between fibers
2. Distance between layers
3. Number of fibers per layer
4. Fiber diameter
5. Tangential angle to curvature MATLAB (http://www.mathworks.com/products/matlab/, Mathworks, MA, USA) was used to count or measure the following parameters:
1. Volume distribution of fibers within cross section of implant Results Table 3a shows the mechanical performance results of three different types of reinforced composites implant pins produced as described above. The structural properties of these implants are described by the production methods discussed above and their internal compositions are seen in the associated images. Quantification of several parameters related to the internal composition structure of the implants can be seen in table 3b.

TABLE 3a

Mean values and standard deviations of the mechanical properties and bulk properties of the implants (n = 3).

| Plate Type | E [MPa] | Flexural Strength [MPa] | Max Load [N] | Density [gr/ml] | Volume [mm³] |
|---|---|---|---|---|---|
| Plate. 50% w/w fiber. T = 0 | 306.9 ± 13.9 | 15362.1 ± 502.4 | 285.27 ± 7.7 | 1.65 | 1624.8 |
| Plate. 50% w/w fiber. T = 5 d | 127.0 ± 39.1 | 11063.3 ± 688.8 | 143.5 ± 41.7 | 1.6 | 1786 |
| Plate. 70% w/w fiber. T = 0 | 358.5 ± 142.9 | 23088.4 ± 2012.5 | 307.56 ± 121 | 1.89 | 1552.0 |
| Plate. 70% w/w fiber. T = 5 d | 83.2 ± 34.3 | 10806.9 ± 1463.3 | 115.76 ± 115.8 | 1.7 | 1947.7 |
| Plate. Amorphous 50% w/w fiber. T = 0 | 108.1 ± 16.5 | 8299.7 ± 1276.9 | 97.4 ± 17.0 | 1.66 | 1595.1 |

Incubation for 5 days in SBF at 50° C., which accelerates degradation rate, resulted in a decrease in flexural modulus of 27% and 53% in the full 50% w/w and full 70% w/w plates respectively. Incubation for 5 days in SBF at 50° C., which accelerates degradation rate, resulted in a decrease in flexural strength of 58% and 76% in the full 50% w/w and full 70% w/w plates respectively.

Incubation for 5 days in SBF at 50° C., which accelerates degradation rate, resulted in a decrease in maximum flexural load of 50% and 62% in the full 50% w/w and full 70% w/w plates respectively.

For this geometry and production method it seems that the increase in fiber content from 50% to 70 w/w, increases the initial mechanical strength but accelerates the degradation process.

Having short non oriented fibers as exist in the amorphous plate versus continuously oriented fibers resulted in a decrease of 46%, 65% and 66% in the modulus, flexural strength and maximum load for a similar density and production conditions.

TABLE 3b

Measured structural parameters relating the reinforcing fibers and biocomposite layers within a biocomposite plate

Figure 17:
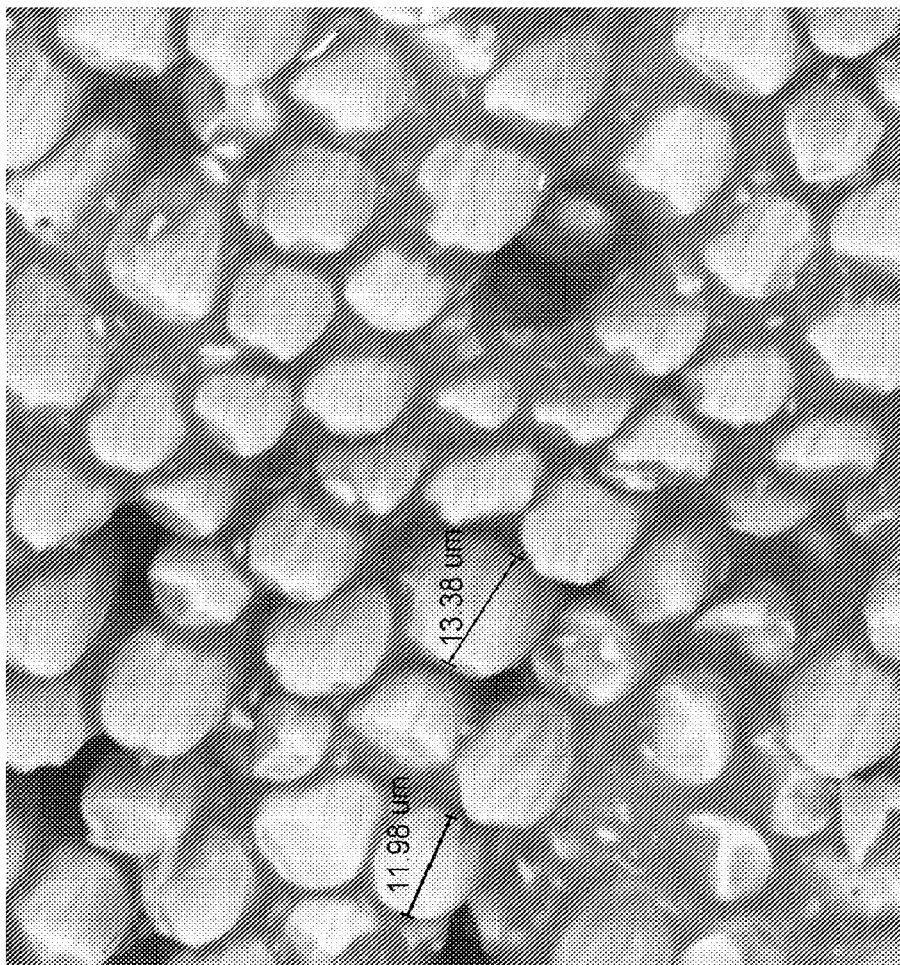
FIG. 17: Scanning Electron Microscope (SEM) image using a Back-Scattered Electrons (BSE) detector of a cross section of a 2 mm plate with 50% fiber content by weight, such as those described in Example 3. Magnification of this image is 1250×. This image shows a magnification of the cross section of reinforcing mineral fibers embedded within bioabsorbable polymer matrix. The fiber diameter is indicated within the image.
Figure 18:
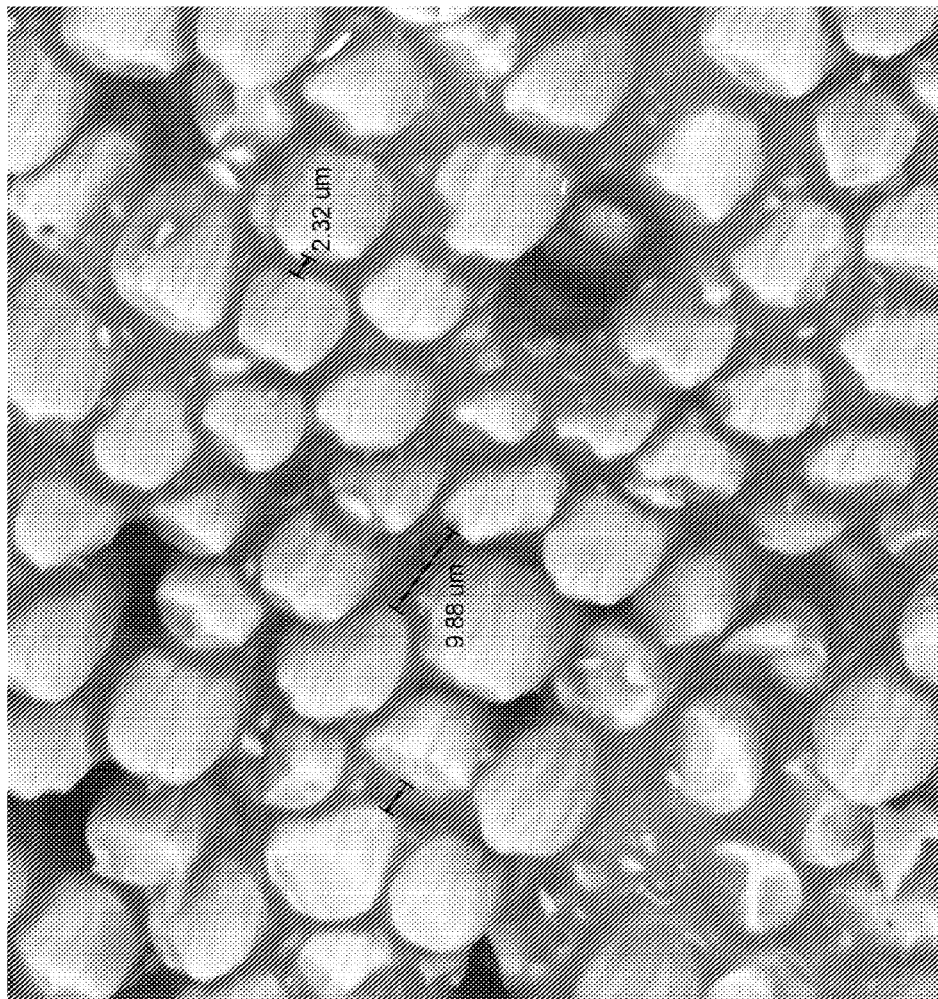
FIG. 18: Scanning Electron Microscope (SEM) image using a Back-Scattered Electrons (BSE) detector of a cross section of a 2 mm plate with 50% fiber content by weight, such as those described in Example 3. Magnification of this image is 1250×. This image shows a magnification of the cross section of reinforcing mineral fibers embedded within bioabsorbable polymer matrix. The distance between adjacent fibers is indicated.
Figure 19:
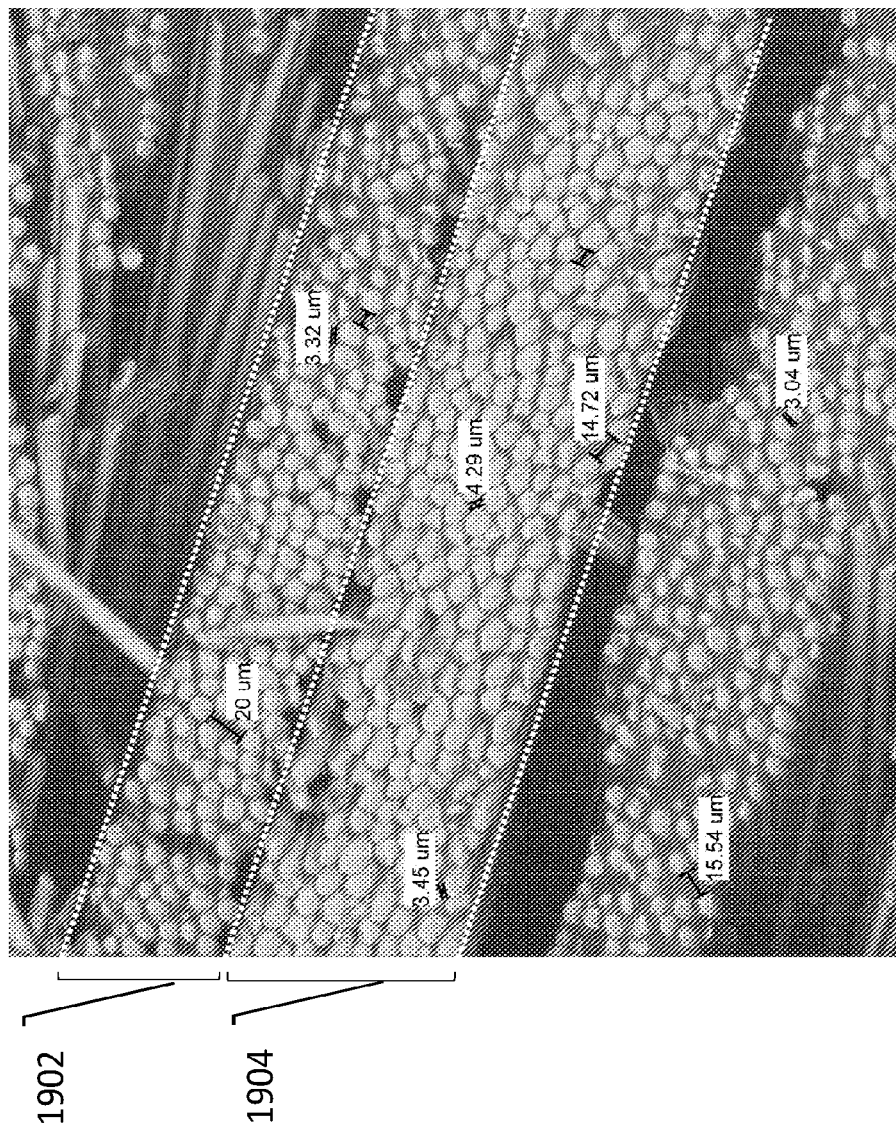
FIG. 19: Scanning Electron Microscope (SEM) image using a Back-Scattered Electrons (BSE) detector of a cross section of a 2 mm plate with 70% fiber content by weight, such as those described in Example 3. Magnification of this image is 250×. This image shows a magnification of the cross section of reinforcing mineral fibers embedded within bioabsorbable polymer matrix. Each layer 1902, 1904 is comprised of fibers. The distance between adjacent fibers is indicated.
Figure 21:
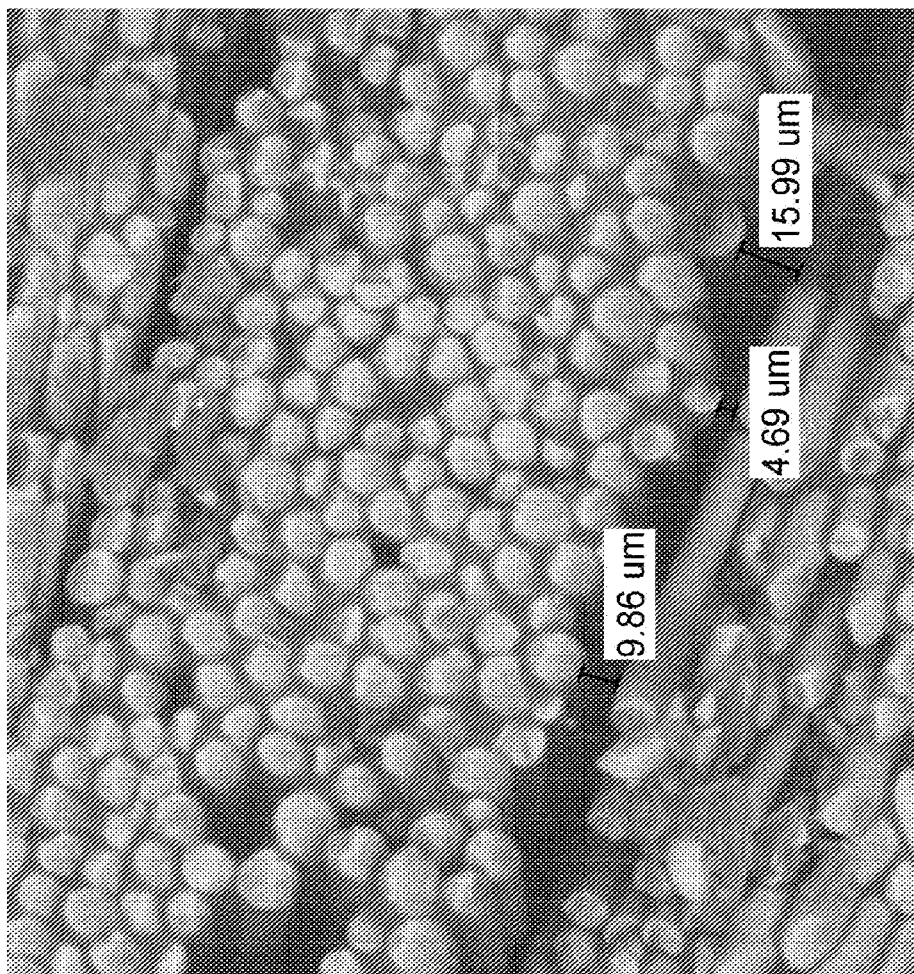
FIG. 21: Scanning Electron Microscope (SEM) image using a Back-Scattered Electrons (BSE) detector of a cross section of a 2 mm plate with 70% fiber content by weight, such as those described in Example 3. Magnification of this image is 500×. This image shows a magnification of the cross section of reinforcing mineral fibers embedded within bioabsorbable polymer matrix. Each layer is separated by an area of bioabsorbable polymer matrix.

|  | Fiber diameter range (μm) | Distance between fibers (μm) | Fibers in layer thickness | Layer thickness (μm) | Distance between layers (μm) |
|---|---|---|---|---|---|
| Plate. 50% w/w fiber | 11.48-13.98 (FIG. 17) | 2.32-9.88 (FIG. 18) |  |  |  |
| Plate. 70% w/w fiber |  | 3.04-20 (FIG. 19) | 6-10 (FIG. 20) | 70.03-110.86 (FIG. 20) | 3.77-15.99 (FIG.21) |

Example #4—Degradation Differences

Below example describes the degradation of orthopedic implants produced with reinforced biocomposite materials. This example demonstrates how different medical implants comprised of reinforced biocomposite materials can differ in performance properties with regards to material loss and swelling ratio following simulated degradation. An absorbable orthopedic implant, used for bone fixation, as intended for the following, ideally needs to retain its strength for the period needed for the bone to heal, and then gradually degrade and lose its strength as it is replaced by bone.

Material weight loss is an indication for the rate of degradation. Swelling ratio is an indication for conformational changes, hydrophilicity as well as an indication for porosity. Control of both parameters are important for implant design.

Materials & Methods

Pin and plate implants were produced using reinforced composite material as described in example 1-3. Material composite was comprised of PLDLA 70/30 polymer reinforced with 50% w/w or 70% w/w continuous mineral fibers. Mineral fibers composition was approximately $Na_2O$ 14%, MgO 5.4%, CaO 9%, $B_2O_3$ 2.3%, $P_2O_5$ 1.5%, and $SiO_2$ 67.8% w/w. Testing samples were manufactured by compression molding of multiple layers of composite material into an appropriate mold. Each layer was comprised of the PLDLA polymer with embedded uni-directionally aligned continuous fibers. Orientation of layers relative to longitudinal axis of implant were 0° (parallel to implant longitudinal axis), 45°, 0°, −45°, 0°, in a repetitive manner according to number of layers in the implant. Each layer was approximately 0.18 mm thick. Three (3) implant samples were produced for each group.

Implant samples were weighed initially and following simulated in vitro degradation according to a modified ASTM F1635, wherein samples were incubated in simulated body fluid (SBF), 142 $Na^+$, 5 $K^+$, 1.5 $Mg^{2+}$, 2.5 $Ca^{2+}$, 147.8 $Cl^-$, 4.2 $HCO_3^-$, 1 $HPO_4^{3-}$, 0.5 $SO_4^{2-}$ mol/m³, for 5 days at a temperature of 50° C., while shaking at 30 rpm. Samples were then dried in a vacuum desiccator overnight and weighed again. Material percentage loss was calculated as (initial weight−dried weight)/initial weight*100. Swelling ratio was calculated as (weight at the end of the incubation−dried weight)/dried weight*100.

Results

Table 4 shows the weight measurement results of different types of reinforced composite implants produced as described above.

TABLE 4

Mean values and standard deviations of implant weight measurements and calculated material loss and swelling ratio (n = 3). Measurements are of the weight at the beginning of the experiment (T0), after degradation of 5 days in SBF at 50° C., 30 rpm (5 days) and after dehydration in the desiccator overnight (dried).

|  | T0 [gr] | 5 Days [gr] | Dried [gr] | Material loss (%) | Swelling ratio (%) |
|---|---|---|---|---|---|
| Full pin. OD 6 mm. 50% w/w | 2.33 ± 0.09 | 2.43 ± 0.09 | 2.35 ± 0.09 | 0.245 | 4.42 |
| Full pin. OD 6 mm. 70% w/w | 2.68 ± 0.09 | 2.79 ± 0.01 | 2.69 ± 0.01 | 0.262 | 4.35 |
| Hollow pin. OD 6 mm. ID 3 mm. 50% w/w | 1.69 ± 0.01 | 1.81 ± 0.01 | 1.69 ± 0.01 | 0.262 | 7.57 |
| Full pin. OD 2 mm. 50% w/w | 0.257 ± 0.01 | 0.273 ± 0.01 | 0.254 ± 0.01 | 1.24 | 7.456 |
| Full pin. OD 2 mm. 70% w/w | 0.281 ± 0.02 | 0.317 ± 0.03 | 0.274 ± 0.02 | 2.6 | 15.626 |
| Hollow pin. OD 2 mm. ID 1 mm. 50% w/w | 0.226 ± 0.03 | 0.246 ± 0.02 | 0.221 ± 0.02 | 2.085 | 11.347 |
| Plate. 50% w/w fiber | 2.755 ± 0.01 | 2.870 ± 0.01 | 2.75 ± 0.01 | 0.143 | 4.353 |
| Plate. 70% w/w fiber | 3.158 ± 0.3 | 3.346 ± 0.3 | 3.149 ± 0.25 | 0.312 | 6.237 |

Mineral fiber concentration increase from 50% to 70%, in the 2 mm pins and plates, increased the material loss and the swelling ratio over time by ~110% and more than 40% respectively. Relative degradation, as measured by relative material loss, seemed to be faster in cannulated implants vs non cannulated designs.

In the 6 mm pins, mineral fiber concentration increase from 50% to 70% also caused an increase in degradation as measured by material loss %. In the 6 mm cannulated pins, the relative degradation increase could also be noted by the increase in swelling ratio of 74% vs the full pins.

Additional Drawings Showing Various Embodiments

FIG. 30 shows a continuous fiber-reinforced tape of the type that can be used to form a layer in a medical implant comprised of continuous fiber-reinforced layers. The top view (3000) shows a single strip of composite tape comprising reinforcement fibers aligned in a single direction within a bioabsorbable polymer matrix. The interspersed reinforcement fibers (3006) within the bioabsorbable polymer matrix (3008) can be seen more clearly in the close-up top view (3002) of the continuous-fiber reinforced composite tape. The reinforcement fibers can be present as separate fibers or in bundles of several reinforcement fibers per bundle. The cross-sectional view of the continuous fiber reinforced tape (3004) shows the bundles of aligned reinforcement fibers (3010) embedded within the bioabsorbable polymer matrix (3012). Fibers preferably do not breach the surface of the bioabsorbable polymer matrix.

FIG. 31 shows a cut-away, three-dimensional view of a continuous fiber-reinforced tape (200). The cut-away view shows the aligned reinforcement fibers (202) embedded within the bioabsorbable polymer matrix (204).

FIG. 32a shows a top-view of a reinforced bioabsorbable composite sheet (300) comprised of three layers of uni-directional fibers at different angles. Each layer can optionally be comprised of continuous fiber reinforced tapes of the type depicted in FIG. 30. The expanded view (302) shows layers of uni-directional fibers at different angles within an implant. One layer (304) aligned in the longitudinal axis, one layer (306) aligned at an angle to the right of the longitudinal axis, and one layer (308) aligned at an angle to the left of the longitudinal axis.

FIG. 32b shows a cut-away view of a reinforced bioabsorbable composite structure (310) comprised of three layers of uni-directional fibers at different angles. One layer (312) aligned in the longitudinal axis, one layer (314) aligned at an angle to the right of the longitudinal axis, and one layer (316) aligned at an angle to the left of the longitudinal axis. Each layer is comprised of reinforced continuous fibers (318) embedded within bioabsorbable polymer matrix (320).

FIG. 33 shows the wall of a continuous-fiber reinforced composite medical implant. The implant wall is comprised of two layers of uni-directional continuous-fiber reinforced composite tape layers (402 & 404) aligned at a perpendicular angle to each other. The medical implant wall additional comprises perforations (406) to allow for tissue penetration into or through the implant.

FIG. 34 shows a bone filler cage that consists of continuous-fiber reinforced composite medical implant walls (500) that additionally contains perforations (502) to allow tissue and cellular ingrowth into the bone filler material (504) contained within the bone filler cage. The bone filler cage optionally includes a separate door to close the cage (506).

FIG. 35 shows a bioabsorbable cannulated screw (600) that is a medical implant comprised of two parts: a continuous-fiber reinforced bioabsorbable composite cylindrical core (602) and bioabsorbable polymer threading (604) that was subsequently molded or 3D printed on top of the continuous-fiber core. This is an example of a bioabsorbable medical implant where a significant amount or majority of the mechanical strength is provided by a continuous-fiber reinforced part that serves as a mechanical support or structure but where additional implant features are comprised of materials that are not continuous fiber reinforced and yet can be molded or printed directly onto the fiber reinforced composite material.

It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination. It will also be appreciated by persons skilled in the art that the present invention is not limited by what has been particularly shown and described hereinabove. Rather the scope of the invention is defined only by the claims which follow.

What is claimed is:

1. A medical implant comprising a biocomposite; wherein the biocomposite comprises a polymer and a plurality of continuous reinforcement fibers; wherein the fibers are aligned in plurality of fiber bundles; wherein said fibers are uni-directionally aligned within each fiber bundle; wherein said polymer is biodegradable and said implant is bioabsorbable; wherein said continuous fibers are longer than 4 mm; and wherein a distance between adjacent reinforcing fibers within the bundle is in the range of 0.5.50 μm.

2. The implant of claim 1, wherein said continuous fibers are longer than 8 mm, 12 mm, 16 mm or 20 mm.

3. The implant of claim 1, wherein a reinforcing fiber length of at least a portion of said fibers is at least 50% of a longitudinal length of the implant.

4. The implant of claim 3, wherein said reinforcing fiber length of a majority of said fibers is at least 50%, at least 60% or at least 75% of said longitudinal length of the implant.

5. The implant of claim 1, wherein a majority of reinforcement fibers within the composite layer are aligned at an angle to the longitudinal axis, wherein said angle is less than 90°, less than 60°, or less than 45° from the longitudinal axis.

6. The implant of claim 1, wherein a diameter of said fibers is in a range of 0.1-100 μm, 1-20 μm, 4-16 μm, 6-20 μm, 10-18 μm, or 14-16 μm.

7. The implant claim 1, wherein a standard deviation of fiber diameter between fibers is less than 5 μm, less than 3 μm, or less than 1.5 μm.

8. The implant of claim 1, wherein a weight percentage of fibers is in a range of 20-90%, or a range of 40%-70%.

9. The implant of claim 1, wherein a volume percentage of reinforcing fibers within the implant is in a range of 30-90%, or a range of 40%-70%.

10. The implant of claim 1, wherein a density of the biocomposite is between 1 to 2 g/ml, between 1.2 to 1.9 g/ml, or between 1.4 to 1.8 g/ml.

11. The implant of claim 1, wherein the implant has a flexural modulus exceeding 10 GPa and flexural strength exceeding 100 MPa.

12. The implant of claim 11, wherein said implant has flexural strength in a range of 400-800 MPa, or a range of 650-800 MPa.

13. The implant of claim 11, wherein said implant has an elastic modulus in a range of 10-27 GPa, or a range of 16-27 GPa.

14. The implant of claim 1, wherein said biodegradable polymer comprises a homopolymer or a copolymer; wherein said copolymer comprises a random copolymer, block copolymer, or graft copolymer; wherein said polymer comprises a linear polymer, a branched polymer, or a dendrimer, of natural or synthetic origin; and wherein said polymer comprises comprises lactide, glycolide, caprolactone, valerolactone, carbonates (e.g., trimethylene carbonate, tetramethylene carbonate, and the like), dioxanones (e.g., 1,4-dioxanone), δ-valerolactone, 1, dioxepanones) e.g., 1,4-dioxepan-2-one and 1,5-dioxepan-2-one), ethylene glycol, ethylene oxide, esteramides, γ-ydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinoneiminocarbonate, (polyurethanes, polyanhydrides, polymer drugs (e.g., polydiflunisol, polyaspirin, and protein therapeutics), sugars; starch, cellulose and cellulose derivatives, polysaccharides, collagen, chitosan, fibrin, hyaluronic acid, polypeptides, proteins, poly (amino acids), polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetra methylglycolide copolymers, lactide/trimethylene carbonate copolymers, lactide/d-valerolactone copolymers, lactide/E-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/E-caprolactone terpolymers, PLA/polyethylene oxide copolymers; polydepsipeptides; unsymmetrically-3,6-substituted poly-1,4-dioxane-2,5-diones; polyhydroxyalkanoates; such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone-poly-E-capralactone, poly (E-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA): poly-b-alkanbic acids; polycarbonates; polyorthoesters; polyphosphates; poly (ester anhydrides); and mixtures thereof; and derivatives, copolymers and mixtures thereof.

15. The implant of claim 14, wherein said polymer is selected from the group consisting of PLLA, PDLA, PGA, PLGA, PCL, PLLA-PCL and a combination thereof.

16. The implant of claim 15, wherein said PLLA is used in said polymer matrix and said matrix comprises at least 30% PLLA.

17. The implant of claim 15, wherein said PDLA is used in said polymer matrix and said matrix comprises at least at least 5% PDLA, least 10% PDLA, or at least 20% PDLA.

18. The implant of claim 1, wherein said fiber comprises a silica-based mineral compound.

19. The implant of claim 18, wherein said silica-based mineral compound has at least one oxide composition in at least one of the following mol. % ranges:

Na$_2$O: 11.0-19.0 mol. %
CaO: 9.0-14.0 mol. %
MgO: 1.5-8.0 mol. %
B$_2$O$_3$: 0.5-3.0 mol. %
Al$_2$O$_3$: 0-0.8 mol. % and
P$_2$O$_3$: 0.1-0.8 mol. %.

20. The implant of claim 19, wherein said silica-based mineral compound has at least one oxide composition in at least one of the following mol. % ranges:

Na$_2$O: 12.0-13.0 mol. %
CaO: 9.0-10.0 mol. %
MgO: 7.0-8.0 mol. %
B$_2$O$_3$: 1.4-2.0 mol. %
P$_2$O$_3$: 0.5-0.8 mol. % and
SiO$_2$: 68-70 mol. %.

21. A method of treatment for an orthopedic application in a subject in need of treatment thereof, comprising implanting to the subject the medical implant of claim 1.

22. A medical implant comprising a biocomposite; wherein the biocomposite comprises a polymer and a plurality of continuous reinforcement fibers; wherein the fibers are aligned in plurality of fiber bundles; wherein said fibers are uni-directionally aligned within each fiber bundle; wherein said polymer is biodegradable and said implant is bioabsorbable; wherein said continuous fibers are longer than 4 mm; and wherein a distance between adjacent reinforcing fibers within the bundle is in the range of 0.5-50 μm; and wherein a density of the biocomposite is between 1 to 2 g/ml, between 1.2 to 1.9 g/ml, or between 1.4 to 1.8 g/ml.

23. A medical implant comprising a biocomposite; wherein the biocomposite comprises a polymer and a plurality of continuous reinforcement fibers; wherein the fibers are aligned in plurality of fiber bundles; wherein said fibers are uni-directionally aligned within each fiber bundle; wherein said polymer is biodegradable and said implant is bioabsorbable; wherein said continuous fibers are longer than 4 mm; and wherein a distance between adjacent reinforcing fibers within the bundle is in the range of 0.5-50 μm; and wherein a weight percentage of fibers in the implant is in a range of 20-90%, or a range of 40%-70%.

24. A medical implant comprising a biocomposite; wherein the biocomposite comprises a polymer and a plurality of continuous reinforcement fibers; wherein the fibers are aligned in plurality of fiber bundles; wherein said fibers are uni-directionally aligned within each fiber bundle; wherein said polymer is biodegradable and said implant is bioabsorbable; wherein said continuous fibers are longer than 4 mm; and wherein a distance between adjacent reinforcing fibers within the bundle is in the range of 0.5-50 μm; and wherein said implant has flexural strength in a range of 400-800 MPa, or a range of 650-800 MPa.

* * * * *